(12) United States Patent
Scharenberg

(10) Patent No.: US 10,407,672 B2
(45) Date of Patent: Sep. 10, 2019

(54) COMPOSITIONS AND METHODS COMPRISING THE USE OF CELL SURFACE DISPLAYED HOMING ENDONUCLEASES

(75) Inventor: Andrew M. Scharenberg, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 784 days.

(21) Appl. No.: 12/295,201

(22) PCT Filed: Mar. 27, 2007

(86) PCT No.: PCT/US2007/007637
§ 371 (c)(1),
(2), (4) Date: Sep. 29, 2008

(87) PCT Pub. No.: WO2007/123636
PCT Pub. Date: Nov. 1, 2007

(65) Prior Publication Data
US 2009/0162937 A1  Jun. 25, 2009

Related U.S. Application Data

(60) Provisional application No. 60/786,255, filed on Mar. 27, 2006.

(51) Int. Cl.
*C12N 9/22* (2006.01)
*C12N 15/10* (2006.01)

(52) U.S. Cl.
CPC ............ *C12N 9/22* (2013.01); *C12N 15/1037* (2013.01)

(58) Field of Classification Search
None
See application file for complete search history.

(56) References Cited

U.S. PATENT DOCUMENTS

| | | | |
|---|---|---|---|
| 5,801,030 | A | 9/1998 | McVey |
| 7,238,360 | B2 | 7/2007 | Shirwan |
| 2003/0039990 | A1* | 2/2003 | Schuur ............................. 435/6 |
| 2003/0073109 | A1 | 4/2003 | Pan |
| 2005/0266565 | A1 | 12/2005 | Yee |
| 2006/0153826 | A1 | 7/2006 | Arnould |
| 2006/0183159 | A1* | 8/2006 | Zhao et al. ..................... 435/7.1 |
| 2006/0206949 | A1 | 9/2006 | Arnould |

FOREIGN PATENT DOCUMENTS

| WO | WO 2004/067736 | 8/2004 |
|---|---|---|
| WO | WO 2007/123636 | 11/2007 |

OTHER PUBLICATIONS

Chames et al., 2005, In vivo selection of engineered homing endonucleases using double-strand break induced homologous recombination, Nucleic Acids Research, 33(20): 10 pages.*
Stahl et al., 1997, Bacterial surface display: trends and progress, TIBTECH, 15: 185-192.*
Kondo et al., 2004, Yeast cell-surface display—applications of molecular display, Appl. Microbiol. Biotechnol., 64: 28-40.*
Geese et al., 2003, In vitro analysis of the relationship between endonuclease and maturase activities in the bi-functional group I intron-encoded protein, I-Anil, Eur. J. Biochem., 270: 1543-1554.*
Belfort et al., 1997, Homing endonucleases: keeping the house in order, Nucleic Acids Research, 25(17): 3379-3388.*
pYD1 Yeast Display Vector Kit, Dec. 10, 2002, Invitrogen, Version D, 26 pages.*
Lee et al Jan. 2003 Trends in Biotechnology 21: 45-52.*
Arnould et al., "Engineering of Large Numbers of Highly Specific Homing Endonucleases that Induce Recombination on Novel DNA Targets," Journal of Molecular Biology, 2006, pp. 443-458, vol. 355.
Bilikova et al., "Enhancing Gene Targeting with designed Zinc Finger Nucleases," Science, 2003, p. 764, vol. 300.
Bilikova et al., "Stimulation of Homologous Recombination through Targeted Cleavage by Chimeric Nucleases," Molecular and Cellular Biology, 2001, pp. 289-297, vol. 21.
Bolduc et al., "Structural and biochemical analyses of DNA and RNA binding by a bifunctional homing endonuclease and group I intron splicing factor," Genes & Development, 2003, pp. 2875-2888, vol. 17.
Bonetta, "Getting Proteins Into Cells," The Scientist, 2002, pp. 38-40, vol. 16.
U.S. Appl. No. 60/786,255, filed Mar. 27, 2006, Scharenberg.
Burt et al., "Homing endonuclease genes: the rise and fall and rise again of a selfish element," Current Opinion in Genetics & Development, 2004, pp. 609-615, vol. 14.
Chames et al., "In vivo selection of engineered homing endonucleases using double-strand break induced homologous recombination," Nucleic Acids Research, 2005, pp. e178, vol. 33 (10 pages).

(Continued)

*Primary Examiner* — Paul J Holland
(74) *Attorney, Agent, or Firm* — Cooley LLP

(57) ABSTRACT

According to particular exemplary aspects, DNA target site binding and cleavage properties of native, variant or modified homing endonucleases (HE) (e.g., LAGLIDAG (LHE), HNH, His-Cys Box, GIY-YIG, I-SspI-type, and fusions, muteins or variants thereof) in solution are recapitulated on the cell surface (e.g., as assessed by flow cytometric analysis) to provide for novel cells expressing one or more cell surface HEs (e.g., expressing one or more HE binding and/or cleavage specificities), novel cell libraries, and high-throughput methods for assessing target site binding, target site cleavage. The rapid analysis of HE and LHE-DNA interactions on the cell surface with concurrent sorting options provides for high-throughput library screening affording rapid identification, analysis and isolation of novel HEs or LHEs having novel sequence specificities. Such novel sequence specificities, obtained by said methods provide novel methods for introducing targeted DNA-strand cleavage events, and novel chromatin immunoprecipitation methods (CHIP methods).

12 Claims, 16 Drawing Sheets

Specification includes a Sequence Listing.

(56) References Cited

OTHER PUBLICATIONS

Chao et al., "Isolating and engineering human antibodies using yeast surface display," Nature Protocols, 2006, pp. 755-768, vol. 1.
Chen et al., "A highly sensitive selection method for directed evolution of homing endonucleases," Nucleic Acids Research, 2005, p. e154, vol. 33 (7 pages).
Chevalier et al., "Design, Activity, and Structure of a Highly Specific Artificial Endonuclease," Molecular and Cellular Biology, 2002, pp. 895-905, vol. 10.
Chevalier et al., "The homing endonuclease I-CreI uses three metals, one of which is shared between the two active sites," Nature Structural Biology, 2001, pp. 312-316, vol. 8.
Chevalier et al., "Homing endonucleases: structural and functional insight into the catalysts of intron/intein mobility," Nucleic Acids Research, 2001, pp. 3757-3774, vol. 29.
Chevalier et al., "Metal-Dependent DNA Cleavage Mechanism of the I-CreI LAGLIDADG Homing Endonuclease," Biochemistry, 2004, pp. 14015-14026, vol. 43.
Chou et al., "Expression of Chimeric Monomer and Dimer Proteins on the Plasma Membrane of Mammalian Cells," Biotechnology and Bioengineering, 1999, pp. 160-169, vol. 65.
Doyon et al., "Directed Evolution and Substrate Specificity Profile of Homing Endonuclease I-SceI," The Journal of the American Chemical Society, 2006, pp. 2477-2484, vol. 128.
Duan et al., "Crystal Structure of PI-SceI, a Homing Endonuclease with protein Splicing Activity," Cell, 1997, pp. 555-564, vol. 89.
Elnitski et al., "Locating mammalian transcription factor binding sites: A survey of computational and experimental techniques," Genome Research, 2006, pp. 1455-1464, vol. 16.
Epinat et al., "A novel engineered meganuclease induces homologous recombination in yeast and mammalian cells," Nucleic Acids Research, 2003, pp. 2952-2962, vol. 31.
Ford et al., "Protein transduction: an alternative to genetic intervention?" Gene Therapy, 2001, pp. 1-4, vol. 8.
Gimble et al., "Assessing the Plasticity of DNA Target Site Recognition of the PI-SceI Homing Endonuclease Using a Bacterial Two-hybrid Selection System," 2003, pp. 993-1008, vol. 334.
Gruen et al., "An in vivo selection system for homing endonuclease activity," Nucleic Acids Research, 2002, p. e29, vol. 30 (6 pages).
Heath et al., "The structure of I-CreI, a Group I intron-encoded homing endonuclease," Nature Structural Biology, 1997, pp. 468-476, vol. 4.
Hu et al., "Probing the Structure of the PI-SceI-DNA Complex by Affinity Cleavage and Affinity Photocross-linking," Journal of Biological Chemistry, 2000, pp. 2705-2712, vol. 275.
Ichiyanagi et al., "Crystal Structure of an Archaeal Intein-encoded Homing Endonuclease PI-PfuI," Journal of Molecular Biology, 2000, pp. 889-901, vol. 300.
Jurica et al., "DNA Recognition and Cleavage by the LAGLIDADG Homing Endonuclease I-CreI," Molecular and Cellular Biology, 1998, pp. 469-476, vol. 2.
Liao et al., "Design of Transgenes for Efficient Expression of Active Chimeric Proteins on Mammalian Cells," Biotechnology and Bioengineering, 2001, pp. 313-323, vol. 73.
Miller et al., "Human Gene Targeting by Adeno-Associated Virus Vectors Is Enhanced by DNA Double-Strand Breaks," Molecular and Cellular Biology, 2003, pp. 3550-3557, vol. 23.
Mohler et al., "Membrane-Bound Neomycin Phosphotransferase Confers Drug-Resistance in Mammalian Cells: A Marker for High-Efficiency Targeting of Genes Encoding Secreted and Cell-Surface Proteins," Somatic Cell and Molecular Genetics, 1994, pp. 153-162, vol. 20.
Nightingale et al., "Transient Gene Expression by Nonintegrating Lentiviral Vectors," Molecular Therapy, 2006, pp. 1121-1132, vol. 13.
Perez et al., "Factors affecting double-strang break-induced homologous recombination in mammalian cells," BioTechniques, 2005, pp. 1-7, vol. 39.
Poland et al., "Structural Insights into the Protein Splicing Mechanism of PI-SceI," Journal of Biological Chemistry, 2000, pp. 16408-16413, vol. 275.
Sato et al., "Targeting of Chrolamphenicol Acetyltransferase to Human Immunodificiency Virus Particles via Vpr and Vpx," Microbiology andImmunology, 1995, pp. 1015-1019, vol. 39.
Seligman et al., "Mutations altering the cleavage specificity of a homing endonuclease," Nucleic Acids Research, 2002, pp. 3870-3879, vol. 30.
Silva et al., "Analysis of the LAGLIDADG interface of the monomeric homing endonuclease I-DmoI," Nucleic Acids Research, 2004, pp. 3156-3168, vol. 32.
Silva et al., "Crystal Structure of the Thermostable Archaeal Intron-encoded Endonuclease I-DmoI," Journal of Molecular Biology, 1999, pp. 1123-1136, vol. 286.
Steuer et al., "Chimeras of the Homing Endonuclease PI-SceI and the Homologous Candida tropicalis Intein: A Study to Explore the Possibility of Exchanging DNA-Binding Modules to Obtain Highly Specific Endonucleases with Altered Specificity," Chembiochem, 2004, pp. 206-213, vol. 5.
Stoddard, "Homing endonuclease structure and function," Quarterly Reviews of Biophysics, 2005, pp. 1-47.
Storici et al., "Chromosomal site-specific double-strand breaks are efficiently targeted for repair by oligonucleotides in yeast," The Proceedings of the National Academy of Sciences, 2003, pp. 14994-14999, vol. 100.
Sussman et al., "Isolation and Characterization of New Homing Endonuclease Specificities at Individual Target Site Positions," Journal of Molecular Biology, 2004, pp. 31-41, vol. 342.
Tzfira et al., "Site-Specific Integration of Agrobacterium tumefaciens T-DNA via Double-Stranded Intermediates," Plant Physiology, 2003, pp. 1011-1023, vol. 133.
Urnov et al., "Highly efficient endogenous human gene correction using designed zinc-finger nucleases," Nature, 2005, pp. 1-6.
Volna et al., "Flow cytometric analysis of DNA binding and cleavage by cell surface-displayed homing endonucleases," Nucleic Acids Research, 2007, pp. 2748-2758, vol. 35.
Wadia et al., "Protein transduction technology," Current Opinion in Biotechnology, 2002, pp. 52-56, vol. 13.
Ward et al., "Characterization of Humanized Antibodies Secreted by Aspergillus niger," Applied and Einvironmental Microbiology, 2004, pp. 2567-2576, vol. 70.
Weinmann, "Novel ChIP-based strategies to uncover transcription factor target genes in the immune system," Nature Reviews Immunology, 2004, pp. 381-386, vol. 4.
Wu et al., "Targeting Foreign Proteins to Human Immunodeficiency Virus Particles via Fusion with Vpr and Vpx," Journal of Virology, 1995, pp. 3389-3398, vol. 69.
McNutt, M. C. et al., "Catalytic Activity Is Not Required for Secreted PCSK9 to Reduce Low Density Lipoprotein Receptors in HepG2 Cells," The Journal of Biological Chemistry vol. 282, No. 29, pp. 20799-20803, Jul. 20, 2007.
Kozlov, I. A. et al., "Efficient Strategies for the Conjugation of Oligonucleotides to Antibodies Enabling Highly Sensitive Protein Detection," Biopolymers, vol. 73, 621-630 (2004).
Sano, T. et al., "Immuno-PCR: Very Sensitive Antigen Detection by Means of Specific Antibody-DNA Conjugates," Science, vol. 258(5079), Oct. 1992, pp. 120-122.
Keefe. A. D. et al., "One-Step Purification of Recombinant Proteins Using a Nanomolar-Affinity Streptavidin-Binding Peptide, the SBP-Tag," Protein Expression and Purification 23, 440-446 (2001).
Takeda, S. et al., "Site-specific conjugation of oligonucleotides to the C-terminus of recombinant protein by expressed protein ligation," Bioorganic & Medicinal Chemistry Letters 14 (2004) 2407-2410.
Kuijpers, W. H. A. et al., "Specific Recognition of Antibody-Oligonucleotide Conjugates by Radiolabeled Antisense Nucleotides: A Novel Approach for Two-Step Radioimmunotherapy of Cancer," Bioconjugate Chem. 1993, 4, 94-102.

\* cited by examiner

SEQUENCE LISTING

```
<160> NUMBER OF SEQ ID NOS: 26

<210> SEQ ID NO 1
<211> LENGTH: 35
<212> TYPE: DNA
<213> ORGANISM: Artificial Sequence
<220> FEATURE:
<223> OTHER INFORMATION: Primer - I-AniI For SfiI

<400> SEQUENCE: 1
ggcccagccg gccatgggca gcagccatca tcatc                               35

<210> SEQ ID NO 2
<211> LENGTH: 35
<212> TYPE: DNA
<213> ORGANISM: Artificial Sequence
<220> FEATURE:
<223> OTHER INFORMATION: Primer - I-AniI Rev SalI

<400> SEQUENCE: 2
gtcgacataa tttgaaggta tttttatttt ttctg                               35

<210> SEQ ID NO 3
<211> LENGTH: 34
<212> TYPE: DNA
<213> ORGANISM: Artificial Sequence
<220> FEATURE:
<223> OTHER INFORMATION: Primer - H-DreI For SfiI

<400> SEQUENCE: 3
ggcccagccg gccatgcata ataatgagaa tgtt                                34

<210> SEQ ID NO 4
<211> LENGTH: 30
<212> TYPE: DNA
<213> ORGANISM: Artificial Sequence
<220> FEATURE:
```

<223> OTHER INFORMATION: Primer - H-DreI Rev SalI

<400> SEQUENCE: 4
gtcgaccggg gacgatttct tttttttcact                              30

<210> SEQ ID NO 5
<211> LENGTH: 34
<212> TYPE: DNA
<213> ORGANISM: Artificial Sequence
<220> FEATURE:
<223> OTHER INFORMATION: Primer - CD80-NeoR For

<400> SEQUENCE: 5
cagaccgtct tccttggatc ggccattgaa caag                          34

<210> SEQ ID NO 6
<211> LENGTH: 31
<212> TYPE: DNA
<213> ORGANISM: Artificial Sequence
<220> FEATURE:
<223> OTHER INFORMATION: Primer - NeoR Rev ClaI

<400> SEQUENCE: 6
atcgatgaac aaacgaccca acacccgtgc g                             31

<210> SEQ ID NO 7
<211> LENGTH: 34
<212> TYPE: DNA
<213> ORGANISM: Artificial Sequence
<220> FEATURE:
<223> OTHER INFORMATION: Primer - SP For Hind3

<400> SEQUENCE: 7
aagcttatgg agacagacac actcctgcta tggg                          34

<210> SEQ ID NO 8
<211> LENGTH: 34
<212> TYPE: DNA
<213> ORGANISM: Artificial Sequence
<220> FEATURE:
<223> OTHER INFORMATION: Primer - CD80-NeoR Rev

<400> SEQUENCE: 8
cttgttcaat ggccgatcca aggaagacgg tctg                          34

<210> SEQ ID NO 9
<211> LENGTH: 49
<212> TYPE: DNA
<213> ORGANISM: Artificial Sequence
<220> FEATURE:
<223> OTHER INFORMATION: Primer - I-AniI K21 T27 SDM

<400> SEQUENCE: 9
cagcatcacc aacaagggta agtacctaca gtatgagctg ggtatcgag           49

<210> SEQ ID NO 10
<211> LENGTH: 49
<212> TYPE: DNA
<213> ORGANISM: Artificial Sequence
<220> FEATURE:
<223> OTHER INFORMATION: Primer - I-AniI K21 T27 SDM Rev

<400> SEQUENCE: 10
ctcgataccc agctcatact gtaggtactt acccttgttg gtgatgctg           49

<210> SEQ ID NO 11
<211> LENGTH: 30
<212> TYPE: DNA
<213> ORGANISM: Artificial Sequence
<220> FEATURE:
<223> OTHER INFORMATION: Oligonucleotide - double stranded Ani1 -9A
      (plus strand)

<400> SEQUENCE: 11 cccccctaagg aggtttctct gtaaaccccc                                     30

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide - double stranded Ani1 -6A
      (plus strand)

<400> SEQUENCE: 12 cccccctgaga aggtttctct gtaaaccccc                                     30

<210> SEQ ID NO 13
<211> LENGTH: 26
<212> TYPE: DNA
<213> ORGANISM: Artificial Sequence
<220> FEATURE:
<223> OTHER INFORMATION: Oligonucleotide - double stranded Dre4 6T (plus
      strand)

<400> SEQUENCE: 13
accaaactgt ctcaagttac ggcgcg                                          26

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide - double stranded Dre4 10T
      (plus strand)

<400> SEQUENCE: 14
accaaactgt ctcaagttcc ggagcg                                          26

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide - double stranded Ani2 (plus
      strand)

<400> SEQUENCE: 15 cccccctgagg aggttactct gtataccccc                                     30

<210> SEQ ID NO 16
<211> LENGTH: 252
<212> TYPE: PRT
<213> ORGANISM: Emericella nidulans

<400> SEQUENCE: 16

Asp Leu Thr Tyr Ala Tyr Leu Val Gly Leu Phe Glu Gly Asp Gly Tyr
1               5                   10                  15

Phe Ser Ile Thr Lys Lys Gly Lys Tyr Leu Thr Tyr Glu Leu Gly Ile
            20                  25                  30

Glu Leu Ser Ile Lys Asp Val Gln Leu Ile Tyr Lys Ile Lys Lys Ile

```
            35                  40                  45
Leu Gly Ile Gly Ile Val Ser Phe Arg Lys Arg Asn Glu Ile Glu Met
 50                  55                  60

Val Ala Leu Arg Ile Arg Asp Lys Asn His Leu Lys Ser Phe Ile Leu
 65                  70                  75                  80

Pro Ile Phe Glu Lys Tyr Pro Met Phe Ser Asn Lys Gln Tyr Asp Tyr
                 85                  90                  95

Leu Arg Phe Arg Asn Ala Leu Leu Ser Gly Ile Ile Ser Leu Glu Asp
            100                 105                 110

Leu Pro Asp Tyr Thr Arg Ser Asp Glu Pro Leu Asn Ser Ile Glu Ser
        115                 120                 125

Ile Ile Asn Thr Ser Tyr Phe Ser Ala Trp Leu Val Gly Phe Ile Glu
130                 135                 140

Ala Glu Gly Cys Phe Ser Val Tyr Lys Leu Asn Lys Asp Asp Asp Tyr
145                 150                 155                 160

Leu Ile Ala Ser Phe Asp Ile Ala Gln Arg Asp Gly Asp Ile Leu Ile
                165                 170                 175

Ser Ala Ile Arg Lys Tyr Leu Ser Phe Thr Thr Lys Val Tyr Leu Asp
            180                 185                 190

Lys Thr Asn Cys Ser Lys Leu Lys Val Thr Ser Val Arg Ser Val Glu
        195                 200                 205

Asn Ile Ile Lys Phe Leu Gln Asn Ala Pro Val Lys Leu Leu Gly Asn
210                 215                 220

Lys Lys Leu Gln Tyr Leu Leu Trp Leu Lys Gln Leu Arg Lys Ile Ser
225                 230                 235                 240

Arg Tyr Ser Glu Lys Ile Lys Ile Pro Ser Asn Tyr
                245                 250

<210> SEQ ID NO 17
<211> LENGTH: 194
<212> TYPE: PRT
<213> ORGANISM: Desulfurococcus mobilis

<400> SEQUENCE: 17

Met His Asn Asn Glu Asn Val Ser Gly Ile Ser Ala Tyr Leu Leu Gly
 1               5                  10                  15

Leu Ile Ile Gly Asp Gly Gly Leu Tyr Lys Leu Lys Tyr Lys Gly Asn
             20                  25                  30

Arg Ser Glu Tyr Arg Val Val Ile Thr Gln Lys Ser Glu Asn Leu Ile
         35                  40                  45

Lys Gln His Ile Ala Pro Leu Met Gln Phe Leu Ile Asp Glu Leu Asn
 50                  55                  60

Val Lys Ser Lys Ile Gln Ile Val Lys Gly Asp Thr Arg Tyr Glu Leu
 65                  70                  75                  80

Arg Val Ser Ser Lys Lys Leu Tyr Tyr Phe Ala Asn Met Leu Glu
                 85                  90                  95

Arg Ile Arg Leu Phe Asn Met Arg Glu Gln Ile Ala Phe Ile Lys Gly
            100                 105                 110

Leu Tyr Val Ala Glu Gly Asp Lys Thr Leu Lys Arg Leu Arg Ile Trp
        115                 120                 125

Asn Lys Asn Lys Ala Leu Leu Glu Ile Val Ser Arg Trp Leu Asn Asn
130                 135                 140

Leu Gly Val Arg Asn Thr Ile His Leu Asp Asp His Arg His Gly Val
145                 150                 155                 160
```

Tyr Val Leu Asn Ile Ser Leu Arg Asp Arg Ile Lys Phe Val His Thr
            165                 170                 175

Ile Leu Ser Ser His Leu Asn Pro Leu Pro Pro Glu Arg Ala Gly Gly
            180                 185                 190

Tyr Thr

<210> SEQ ID NO 18
<211> LENGTH: 260
<212> TYPE: PRT
<213> ORGANISM: Artificial Sequence
<220> FEATURE:
<223> OTHER INFORMATION: Desulfurococcus Mobilis/Chlamydomonas
      Reinhardtii construct

<400> SEQUENCE: 18

Met His Asn Asn Glu Asn Val Ser Gly Ile Ser Ala Tyr Leu Leu Gly
1               5                   10                  15

Leu Ile Trp Gly Asp Gly Gly Leu Tyr Lys Leu Lys Tyr Lys Gly Asn
            20                  25                  30

Arg Ser Glu Tyr Arg Val Val Ile Thr Gln Lys Ser Glu Asn Leu Ile
        35                  40                  45

Lys Gln Phe Ile Ala Pro Arg Met Gln Phe Leu Ile Asp Glu Leu Asn
    50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Tyr Phe Ala Asn Met Leu Glu
                85                  90                  95

Arg Ile Arg Leu Phe Asn Gly Asn Arg Phe Leu Ala Tyr Leu Ala Gly
            100                 105                 110

Ile Val Asp Gly Asp Gly Ser Ile Ile Ala Gln Ile Lys Pro Asn Gln
        115                 120                 125

Ser Tyr Lys Phe Lys His Gln Leu Ser Leu Thr Phe Gln Val Thr Gln
    130                 135                 140

Lys Thr Gln Arg Arg Trp Phe Leu Asp Lys Leu Val Asp Glu Ile Gly
145                 150                 155                 160

Val Gly Tyr Val Arg Asp Arg Gly Ser Val Ser Asp Tyr Ile Leu Ser
                165                 170                 175

Glu Ile Lys Pro Leu His Asn Phe Leu Thr Gln Leu Gln Pro Phe Leu
            180                 185                 190

Asn Phe Lys Gln Lys Gln Ala Asn Leu Val Leu Lys Ile Ile Glu Gln
        195                 200                 205

Leu Pro Ser Ala Lys Glu Ser Pro Asp Lys Phe Leu Glu Val Cys Thr
    210                 215                 220

Trp Val Asp Gln Ile Ala Ala Leu Asn Asp Ser Lys Thr Arg Lys Thr
225                 230                 235                 240

Thr Ser Glu Thr Val Arg Ala Val Leu Asp Ser Leu Ser Glu Lys Lys
                245                 250                 255

Lys Ser Ser Pro
            260

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide - double stranded Ani1 (plus
      strand)

<400> SEQUENCE: 19
tgaggaggtt tctctgtaa                                                        19

<210> SEQ ID NO 20
<211> LENGTH: 163
<212> TYPE: PRT
<213> ORGANISM: Chlamydomonas reinhardtii

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 21
<211> LENGTH: 1701
<212> TYPE: DNA
<213> ORGANISM: Mus musculus

<400> SEQUENCE: 21 gagtttttata cctcaataga ctcttactag tttctctttt tcaggttgtg aaactcaacc         60
ttcaaagaca ctctgttcca tttctgtgga ctaataggat catctttagc atctgccggg        120
tggatgccat ccaggcttct ttttctacat ctctgtttct cgattttgt gagcctagga         180 ggtgcctaag ctccattggc tctagattcc tggctttccc catcatgttc tccaaagcat        240
ctgaagctat ggcttgcaat tgtcagttga tgcaggatac accactcctc aagtttccat        300
gtccaaggct cattcttctc tttgtgctgc tgattcgtct ttcacaagtg tcttcagatg        360
ttgatgaaca actgtccaag tcagtgaaag ataaggtatt gctgccttgc cgttacaact        420
ctcctcatga agatgagtct gaagaccgaa tctactggca aaaacatgac aaagtggtgc        480
tgtctgtcat tgctgggaaa ctaaaagtgt ggcccgagta taagaaccgg actttatatg        540
acaacactac ctactctctt atcatcctgg gcctggtcct ttcagaccgg gcacataca         600 gctgtgtcgt tcaaaagaag gaagaggaa cgtatgaagt taaacacttg gctttagtaa        660
agttgtccat caaagctgac ttctctaccc ccaacataac tgagtctgga aacccatctg        720
cagacactaa aaggattacc tgctttgctt ccggggggttt cccaaagcct cgcttctctt        780
ggttggaaaa tggaagagaa ttacctggca tcaatacgac aatttcccag gatcctgaat        840

-continued

```
ctgaattgta caccattagt agccaactag atttcaatac gactcgcaac cacaccatta     900
agtgtctcat taaatatgga gatgctcacg tgtcagagga cttcacctgg gaaaaacccc     960
cagaagaccc tcctgatagc aagaacacac ttgtgctctt tggggcagga ttcggcgcag    1020
taataacagt cgtcgtcatc gttgtcatca tcaaatgctt ctgtaagcac agaagctgtt    1080
tcagaagaaa tgaggcaagc agagaaacaa acaacagcct taccttcggg cctgaagaag    1140
cattagctga acagaccgtc ttcctttagt tcttctctgt ccatgtggga tacatggtat    1200
tatgtggctc atgaggtaca atctttcttt cagcaccgtg ctagctgatc tttcggacaa    1260
cttgacacaa gatagagtta actgggaaga gaaagccttg aatgaggatt tctttccatc    1320
aggaagccta cgggcaagtt tgctgggcct tgattgcttg atgactgaa gtggaaaggc     1380 tgagcccact gtgggtggtg ctagcccctgg gcaggggcag gtgaccctgg gtggtataag    1440
aaaaagagct gtcactaaaa ggagaggtgc ctagtcttac tgcaacttga tatgtcatgt    1500
ttggttggtg tctgtgggag gcctgccctt ttctgaagag aagtggtggg agagtggatg    1560
gggtgggggc agaggaaaag tgggggagag ggcctgggag gagaggaggg aggggggacgg   1620 ggtgggggtg gggaaaacta tggttgggat gtaaaaacga taataatata aatattaaat    1680
aaaaagagag tattgagcaa a                                              1701
```

<210> SEQ ID NO 22
<211> LENGTH: 306
<212> TYPE: PRT
<213> ORGANISM: Mus musculus

<400> SEQUENCE: 22

```
Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
```

```
                210              215              220
Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
                260                 265                 270

Lys His Arg Ser Cys Phe Arg Arg Asn Glu Ala Ser Arg Glu Thr Asn
                275                 280                 285

Asn Ser Leu Thr Phe Gly Pro Glu Glu Ala Leu Ala Glu Gln Thr Val
                290                 295                 300

Phe Leu
305

<210> SEQ ID NO 23
<211> LENGTH: 26
<212> TYPE: DNA
<213> ORGANISM: Artificial Sequence
<220> FEATURE:
<223> OTHER INFORMATION: oligonucleotide-double stranded H-DreI
      recognition site (dsDre4) (plus strand)

<400> SEQUENCE: 23
accaaactgt ctcaagttcc ggcgcg                                        26

<210> SEQ ID NO 24
<211> LENGTH: 30
<212> TYPE: DNA
<213> ORGANISM: Artificial Sequence
<220> FEATURE:
<223> OTHER INFORMATION: oligonucleotide-double stranded I-Ani1
      recognition site (dsAni1) (plus strand)

<400> SEQUENCE: 24
ccccctgagg aggtttctct gtaaacccc                                     30

<210> SEQ ID NO 25
<211> LENGTH: 9
<212> TYPE: PRT
<213> ORGANISM: Artificial Sequence
<220> FEATURE:
<223> OTHER INFORMATION: LAGLIDADG homing endonuclease sequene motif

<400> SEQUENCE: 25

Leu Ala Gly Leu Ile Asp Ala Asp Gly
1               5

<210> SEQ ID NO 26
<211> LENGTH: 6
<212> TYPE: PRT
<213> ORGANISM: Artificial Sequence
<220> FEATURE:
<223> OTHER INFORMATION: GIY-YIG homing endonuclease sequene motif

<400> SEQUENCE: 26

Gly Ile Tyr Tyr Ile Gly
1               5
```

COMPOSITIONS AND METHODS COMPRISING THE USE OF CELL SURFACE DISPLAYED HOMING ENDONUCLEASES

CROSS-REFERENCE TO RELATED APPLICATIONS

This application claims the benefit of priority to U.S. Provisional Patent Application Ser. No. 60/782,255, filed on Mar. 27, 2006 and entitled "Method For Isolation of Homing Endonucleases (HE) With Novel DNA Cutting Site Specificities," which is incorporated by reference herein in its entirety.

STATEMENT REGARDING FEDERALLY-SPONSORED RESEARCH

This work was funded at least in part under grant number R21AI064581 from the National Institutes of Health, and the United States Government may therefore have certain rights.

FIELD OF THE INVENTION

Aspects of the present invention relate generally to novel site-specific DNA cutting enzymes, and more particularly to homing endonucleases (HE) (e.g., LAGLIDAG, HNH, His-Cys Box, GIY-YIG, I-SspI-type) with novel or altered DNA binding and/or cutting specificities, to novel methods of generation, selection and isolation of same comprising the use of cell-surface HE display, to novel compositions (e.g., HEs, HE-encoding nucleic acids, cells, cell libratires, etc.) and novel uses comprising same including for example, generation of targeted double-strand breaks in target viral or cellular genomes, and specific chromatin immunoprecipitation.

SEQUENCE LISTING

A Sequence Listing comprising SEQ ID NOS:1-26 is incorporated by reference herein in its entirety as part of this application.

BACKGROUND

Homing.

'Homing' is a widespread process involving the transfer of an intervening sequence (e.g., introns (e.g., group I or group II introns) or inteins) to a homologous allele that lacks the sequence, leading to gene conversion and dominant transmission and inheritance of the mobile element. Intervening sequences capable of homing are found in all brances of life (e.g., phage, Eubacteria, Archaea, and eukaryotes), and within eukaryotes for example are found within nuclear, mitochondrial and chloroplast genomes. Homing is initiated by an endonuclease (homing endonuclease; HE), encoded within the intervening sequence or intein, which recognizes a DNA target site and generates a single- or double-strand break. HEs are normally expressed in the cytosol and targeted to DNA-containing organelles posttranslationally.

Group I and group II introns are distinguished based on their respective transfer mechanisms. Transfer of group I introns is completed by cellular mechanisms that repair the stand breaks via homologous recombination. Homing of group II introns involves a more complex process comprising strand cleavage, reverse splicing to generate a DNA-RNA hybrid intermediate, and reverse transcription using the inserted RNA as template, where the sequential activities are encoded by within the intron on a single multifunctional polypeptide chain. The homing mechanism of inteins is similar to that of group I introns, but the system comprises functional fusion (in-frame) of the endonuclease with the intein host to provide a polypeptide chain harboring activities of the homing endonuclease, the intein peptide ligase and the host protein, and wherein the portions of the intein's surface participate in DNA recognition and binding by the endonuclease. In all cases, the homing endoculease gene is duplicated into the target site (e.g., non-disruptive sites such as introns and inteins, etc.).

Homing Endonucleases and Classes Thereof.

Homing endonucleases are highly specific DNA cutting enzymes and recognize DNA target sites ranging from about 14 to about 40 base pairs. While being highly specific to promote precise transfer of introns or inteins and avoid genomic toxicity, the homing endoculeases must retain sufficient site recognition flexibility (sufficient infidelity) to permit lateral transfer in the face of sequence variation in diverging targets and host. There are five known families of homing endonucleases (LAGLIDAG, HNH, His-Cys Box, GIY-YIG and I-SspI-type) that differ in their conserved nuclease active-site core motifs and catalytic mechanism.

LAGILDADG motif (SEQ ID NO:25) homing endonucleases (LHE) are the largest family of homing endonucleases, and are typically encoded within introns (as free-standing enzymes) or inteins (as in-frame fusion proteins) of mintochondrial or chloroplast genomes in single-cell eukaryotes (e.g., yeast). LHE homing endonucleases were first defined in the early 1990s with the discovery that the "homing" property of a mobile intron to intron-less alleles of S. Cerevesiae involved the induction of a specific double-strand break in intronless alleles of the gene, the break being generated by a nuclease protein encoded by the mobile intron. The created double-strand break catalyzes homologous recombination between the intron containing and non-containing alleles, resulting in the copying of the intron into the intron-less allele. The intron-encoded protein, I-SceI, and related proteins, were subsequently designated as "homing" endonucleases. Because of a recognizable motif present in two central alpha helixes of I-SceI, this homing endonuclease family, including I-SceI, became known as the LAGLIDADG motif (SEQ ID NO:25) homing endonuclease (LHE) family. LHE proteins are formed as homodimers or pseudosymmetric monomers that generally recognize DNA sequences 18-24 base-pairs in length (Chevalier & Stoddard, *Nucleic Acids Res*, 29:3757-3774, 2001). Homodimers recognize consensus DNA targets that are constrained to paladromic or near palindromic symmetry, whereas monomeric enzymes having two copies of the consensus LAGLIDADG motif (SEQ ID NO:25) possesses a pair of structurally similar nuclease domains on a single polypeptide chain, and are not constrained to symmetric DNA targets. Generally, the molecular structures are built around two conserved alpha-helices that contain the LAGLIDADG motif (SEQ ID NO:25), and which forms the center of the interface between enzyme subunits or domains as the case may be (Heath, et al., *Nat Struct Biol*, 4:468-476, 1997). The final acidic residues from the central alpha helix helices form part of each domain's active site that cleaves one strand of the double-stranded DNA target sequence. The DNA binding interface of each domain is made up of a four-stranded antiparallel beta-sheet that is supported by a series of framework alpha-helices which form the core of the domain. Unlike art-recognized 'restriction endonucleases,' which form densely packed and almost completely saturated DNA-protein interfaces, the DNA binding interface of LHEs make fewer hydrogen bonds per target sequence base pair (Galburt & Stoddard, *Biochemistry,* 41:13851-13860, 2002). These structural properties account for the ability of LHEs to withstand moderate variability in target sequence recognition (e.g., see Jurica, et al., *Mol Cell,* 2:469-476, 1998; Chevalier, et al., *J Mol Biol,* 329:253-26, 2003; Moure, et al., *J Mol Biol,* 334:685-695, 2003; and Moure, et al., *Nat Struct Biol,* 9:764-77, 2002), a characteristic that has been essential in maintaining their genetic mobility and horizontal proliferation (Burt & Koufopanou, *Curr Opin Genet Dev,* 14:609-615, 2004) and which make LHEs ideal substrates for engineering altered DNA binding interfaces with novel endonucleolytic specificities (Duan, et al., 89:555-56, 1997; Chevalier, et al., *Mol Cell,* 10:895-905, 2002; Epinat, et al., *Nucleic Acids Res,* 31:2952-2962, 2003; Arnould, et al., *J Mol Biol,* 355:443-458, 2006; and Steuer, et al., *Chembiochem,* 5:206-213, 2004). The combination of high target sequence specificity and adaptable DNA binding interfaces make LHEs attractive tools for genome engineering applications which require the introduction of a double-stranded break at a precise genomic location (Steuer, et al., *Chembiochem,* 5:206-213, 2004; Storici, F., Durham, et al., *Proc Natl Acad Sci USA,* 100:14994-14999, 2003; Tzfira, et al., *Plant Physiol,* 133:1011-1023, 2003; and Miller, et al., *Mol Cell Biol,* 23:3550-3557, 2003). DNA binding by intein-associated LHEs (e.g., PI-Scep involves recruitment of adjacent protein domains (adjacent intein domains). For example, the PI-SceI endonuclease intein combination binds a 31 bp site, and the majority of the energetic contribution to binding is derived from interactions with the intein peptide splicing domain; the endonuclease domain contains the active sites, but exhibits relatively weak, non-specific DNA binding.

Despite little primary sequence homology among the LHEs outside of the LAGLIDADG motif (SEQ ID NO:25) itself, the topologies among the endonuclease domains and the shape of their DNA-bound β-sheets, are remarkably similar, and the structure of the central core of β-sheets is well conserved. These positions correspond to residues that make contacts to base pairs in each DNA half-site. Alignments of intein-associated endonuclease domains indicate a somewhat more diverged structure of the β-sheet motifs. In particular instances, the core fold of LHE enzymes can be tethered to additional functional domains (e.g., NUMODS; nuclear associated modular DNA binding domains) involved in DNA binding.

Like most nucleases, LHEs require divalent cations for activity. Two metals (calcium and copper) fail to support cleavage, two (nickel and zinc) display reduced cleavage, and three (magnesium, cobalt and manganese) display full activity under all tested conditions. The use of manganese in place of magnesium allows recognition and cleavage of a broader repertoire of DNA target sequences than observed with magnesium.

The HNH and His-Cys box homing endonucelases appear to be derived from a common ancestor built around a consensus nuclease active site architecture known as a 'ββα-metal' motif. The HNH homing endonuclease family if generally found in page introns, and possess a long monmeric extended, modular monomeric structure, in which the relatively non-specific nuclease domain at the N-terminus is tethered to additional structural motifs that confer and restrict DNA binding specificity. Prototypical members (e.g., I-Hmul) recognize asymmetric DNA sites of about 24 bp or longer. In contrast, the His-Cys box homing endonucleases are generally encoded in nucleolar introns within rDNA host genes, have compact homodimeric structures, recognize shoiter symmetric DNA target sites with higher overall homing in a manner similar to the LHE systems.

The GIY-YIG motif (SEQ ID NO:26) endonuclease family members are also encoded within phage introns and possess modular structures similar to the HNH endocleases. The GIY-YIG motif (SEQ ID NO:26) endonuclease catalytic domain is quite non-specific in its inherent cleavage activity, again (as for the HNH family) being restricted to target sites that are dictated by the appended DNA-binding modules.

The fifth family, represented by the prototypical enzyme I-SspI found in *Synechocystis,* is responsible for the presence and persistence of introns in cyanobacterial tRNA genes. I-SspI displays limited homology to known nuclease superfamilies, and is currently represented by only a limited number of indentified open reading frames.

Molecular Biology and Genome Engineering Applications.

Because of their relatively long recognition sequences, homing endonucleases (e.g., LHEs) induce a very low frequency of cleavage, even in large vertebrate genomes, and homing endonucleases are therefore regarded as having possible utility as rare-cutter endonucleases for use in molecular biology and genome engineering applications, particularly those applications which mimic their well known natural function of catalyzing homologous recombination via induction of a DNA double strand break, such as those related to targeted recombination, gene repair and gene conversion.

Engineering and Directed Evolution of Alternative Systems.

Some efforts have been directed to tethering non-specific nuclease domains to sequence-specific DNA binding modules such as zinc fingers (resulting in so called zinc finger nucleases, or ZFNs) for in vivo use in stimulating homologous recombination (Bilikova et al., 2001, 2003) and to drive sequence correction of a disease-causing allele associated with a severe genetic disorder (Urnow et al., 2005). However, despite the ease of designing such highly specific ZFN reagents, comparison of their properties to those of homing endonucleases indicates that both are worthy of development. For example, the nuclease domains of ZFN constructs appear to display significant non-specific DNA nicking and cleaving activity in the engineered chimeras, and these constructs can generate multiple adjacent phosphate cleavage events within a single bound DNA target site, which may enhance non-conservative break repair outcomes. By contrast, LHE cleavage is tightly coupled to cognate site binding, and the enzyme action, by virtue of tight product binding properties, appears to strongly enhance the ratio of homologous recombination relative to undesirable, non-conservative double-strand break repair events such as non-homologous end-joining. Additionally, ZFN chimeras have the disadvantage that they require expression of two separate chains to generate double-strand breaks, and more total coding sequence to generate the active enzyme. Efforts have been made to increase or alter the specificity of type II restriction endonucleases, but have been generally unsuccessful. Group II homing endonucleases are promising for targeted gene disruptions because they are easily engineered for novel specificities by altering the cognate intron sequences (DNA specificity being dictated by base pairing with the RNA component of the intron-protein complex, rather than by only the protein contacts to DNA). However, these systems are more appropriate for gene disruption by insertion of a mobile element than for gene conversion, and require the presence of packaging of significant amounts of genetic information, including a large multifunctional reading frame (RT, endonuclease and maturase) and the cognate intron sequence for the generation of reactive RNP for reverse splicing and gene insertion.

Engineering and Directed Evolution of Homing Endonucleases.

One strategy in the art to alter homing endonuclease specificity for intein-associated enzymes has been to exchange entire intein-binding domains or portions thereof. Experiments of this type have shown, for example, that the PI-SceI protein splicing domain can be used as a site-specific DNA-binding module in chimeric protein constructs (domain swapping between the PI-SceI and a homolog from *Candida tropicalis* (PI-CtrIP) was constructed) (Steuer et al, 2004).

Additionally, several studies have demonstrated that domains from unrelated free-standing LAGLIDADG enzymes can be structurally fused to create fully active, chimeric homing endonucleases that recognize corresponding chimeric target sites (Chevalier et al., 2002, Epinat et al., 2003; Steurer et al., 2004). For example, using computational redesign, an artificial highly specific chimeric endonuclease H-DreI was generated by fusing domains of homing endonucleases I-DmoI and I-CreI. H-DreI binds a long chimeric DNA target site with nanomolar affinity. A related experiment showed that a single-chain monomeric endonuclease can be generated from a homodimer predecessor by generating a fusion of genes that encoded each subunit connected with an artificial linker (Epinat et al., 2003). Specifically, a linker from I-DmoI was used to join two copies of the I-CreI gene to generate a pseudo-symmetric single-chain enzyme that cleaves DNA with the same specificity as native I-CreI, and was shown to initiate homologous recombination in both yeast and mammalian cells.

Moreover, the role and mutability of interfacial residues between LAGLIDADG (SEQ ID NO:25) helices has been examined by grafting side-chains from the homodimeric I-CreI into the corresponding positions in the monomeric I-DmoI enzyme resulting in enzymes with novel nicking activities and oligomeric properties (Silva & Belfort, 2004).

Additionally, several methods have been used to alter homing endonuclease specificity primarily at the level of individual base-pair alterations in the cognate target site, and these methods are divided into (i) those select or screen for DNA binding activity, and (ii) those that select or screen for cleavage. For example, an adaptation of a bacterial two-hybrid strategy was used to select for variants of the intein-encoded PI-SceI endonuclease (Gimble et al., 2003), and the selected DNA binding specificities ranged from relaxed (cleaves WT and mutant targets equally) to being dramatically shifted to preferring the selection targets, but none of the variants displayed the same degree of specificity as WT PI-SceI.

A strategy for isolating I-CreI derivative with increased affinities for altered target sites has been described (Seligman et al., 2002); Sussman et al., 2004). Endonuclease mutants with single amino acid substitutions at positions predicted to make base-specific DNA contacts were assayed against DNA target site mutants in an *E. coli* based system where cleavage of target sites results in cell being converted from lac$^+$ to Lac$^-$, and where undesirable activity (cleavage of original WT site) can be suppressed through a secondary 'negative screen for elimination of an essential reporter (e.g., antibiotic resistance marker). Using these methods, enzyme variants with shifted, rather than completely altered specificity proteins were obtained (see also Gruen et al., 2002).

Finally, an assay system designed to report on the generation of double-strand break induced homologous recombination in eukaryotic cells has been described (Perez et al 2005; see also US 2006/0206949 and US2006/0153826 to Arnould et al; both incorporated by reference herein in their entirety).

However, such prior art based screening methods whether based on domain swapping, domain fusion, enzyme fusion, grafting of side-chains, base-pair alterations in the cognate target site (whether based on selecting or screening for DNA binding activity, or selecting or screening for cleavage activity) are fundamentally limited or compromised in their screening throughput by the fact that they require the generation of combinatorial endonuclease mutant libraries and the variant endonucleases must be well tolerated by the host's genomic DNA; that is, these prior art methods all require intracellular expression of the generated homing endonuclease during the screening or selection, and thereby preclude the effective expression, selection and identification of any variant endonuclease specificities associated with genomic toxicity (e.g., those that cut in and mediate alteration of essential genomic positions). An additional limitation of the prior art is that the intracellular cleavage system must be redesigned and generated for each sequence targeted for selection.

Furthermore, while 'phage display' methods (Chames, et al., Nucleic Acids Research 33:e178, pages 1-10), 2005) have been described for selecting variants of a homodimeric I-CreI enzyme, this system has several fundamental disadvantages. First, such phage display systems have not been demonstrated to provide for display of a single-chain monomeric I-CreI enzyme form, most likely because expression of an active single chain monomeric I-CreI is either toxic to the host bacteria (e.g., using bacterial hosts, phage display of a whole monomeric enzyme would not segregate the active enzyme from the bacterial host cell DNA, as bacteria do not have a sequestered protein secretion pathway), or is disruptive of phage assembly (presumably, the use of a monomer of the homodimeric form generates an inactive fusion protein inside the cell, which would avoid toxicity, and/or was small enough to allow for phage assembly). In any case, no full-length single-chain monomeric active HEs or LHEs have been surface displayed using phage display, or any other type of display including cell surface display. Moreover, additional disadvantages of phage display systems are that phage are relatively small (e.g., compared to cells), and are too small to sort by some methods. Furthermore, in many instances it may not be possible to phage display enough molecules to achieve an adequate signal strength (e.g., depending on the protein, there may be only a few molecules per phage), so separation methods are limited to those comprising matrix/panning approaches, which substantially limits utility screening throughput.

Pronounced Need in the Art.

There is, therefore, a pronounced need in the art for novel site-specific DNA binding and cutting enzymes, and more particularly for novel homing endonucleases (HE) with novel DNA binding and cutting specificities, for novel methods of generation, selection and isolation of same, for novel compositions and uses comprising same, and for novel nucleic acid molecules encoding same. There is a pronounced need for novel LHE with novel DNA binding and cutting specificities, for novel methods of generation, selection and isolation of same, for novel compositions and uses comprising same, and for novel nucleic acid molecules encoding same. There is a pronounced need for methods of variant homing endonuclease expression, selection, screening and identification that are not limited to intracellular expression of the generated homing endonuclease during the screening or selection to allow for generation and identification of a more diverse set of homing endonuclease binding and cleavage specificities.

SUMMARY OF THE INVENTION

According to particular aspects of the present invention, DNA target site binding and cleavage properties of native homing endonucleases (HE) in solution are recapitulated on the cell surface (e.g., as assessed by flow cytometric analysis of both the binding and cleavage of fluorescently conjugated double-stranded oligonucleotides (dsOligos)) to provide for novel cells expressing one or more cell surface HEs (e.g., expressing one or more HE binding and/or cleavage specificities), novel libraries of such cells, and high-throughput methods for assessing target site binding, target site cleavage. Additionally, the rapid analysis of HE or LHE-DNA interactions on the cell surface with concurrent sorting options provides for high-throughput library screening affording rapid identification, analysis and isolation of novel HEs or LHEs having novel sequence specificities. Such novel sequence specificities, obtained by said methods provide a novel method of introducing a DNA-strand cleavage event in a target cell.

Particular aspects of the present invention provide novel methods for the cell surface display of functional homing endonucleases (HE) (e.g., LAGLIDAG, HNH, His-Cys Box, GIY-YIG and I-SspI-type) or of variants, muteins or derivatives thereof. In particular aspects, one or more LAGILDADG homing endonucleases (LHEs), or variants, muteins or derivatives thereof, are expressed as membrane-anchored recombinant proteins and thereby functionally displayed on the surface of the expressing cells (e.g., expressed on the plasma membrane of lymphocyte cell lines by targeting the expression of an LHE-CD80 fusion protein to the secretory pathway). In particular embodiments, only a single HE or LHE is expressed and displayed on a given cell. In alternate embodiments, a plurality of HEs or LHEs are expressed and displayed on a given cell. In particular embodiments, novel cells (e.g., eukaryotic cells, vertebrate, mammalian or other metaozoan cells, yeast or other unicellular eukaryotic cells, bacterial or other prokaryotic cells etc. expressing such cell surface displayed HEs or LHEs are provided.

Additional aspects provide novel cell-based libraries of such cell surface-displayed HEs or LHEs, or of variants, muteins or derivatives thereof. The cells of such libraries may express a single cell surface-displayed HE or LHE or variant, mutein or derivative thereof, or may express a plurality of cell surface-displayed HEs or LHEs, or of variants, muteins or derivatives thereof.

Yet additional aspects provide novel methods for assessing HE or LHE target site binding (e.g., DNA binding) or variant target site binding, comprising assessing the target site binding properties of one or more cell surface displayed functional homing endonucleases, or of variants, muteins or derivatives thereof. In particular embodiments, cells expressing one or more surface LHEs are stained with fluorescently conjugated double-stranded oligonucleotides (dsOligos) containing respective and/or prospective LHE target sequences (or variant target sequences), to provide for analysis of their DNA binding by flow cytometry. In certain embodiments, the detected signal is highly or completely sequence specific and relatively undetectable or undetectable with dsOligos carrying one or more base substitutions (e.g., carrying a single base pair substitution). In particular embodiments, cell surface binding of the target sequence or variant target sequence to HE or LHE-expressing cells is affected under conditions precluding cleavage of the target sequence or variant target sequence.

Further aspects provide novel methods for assessing HE or LHE target site cleavage (e.g., DNA binding and cleavage) or variant target site cleavage, comprising assessing the target site cleaving properties of one or more cell surface displayed functional homing endonucleases, or of variants, muteins or derivatives thereof. In particular embodiments, cells expressing one or more surface LHEs are stained with fluorescently conjugated double-stranded oligonucleotides (dsOligos) containing respective and/or prospective appropriately labeled (e.g., unique fluorophores at opposite termini) LHE target sequences or variant target sequences, to provide for analysis of their DNA cleavage (e.g., DNA binding and cleavage) by flow cytometry. In certain embodiments, the detected signal is highly or completely sequence specific and relatively undetectable or undetectable with dsOligos carrying one or more base substitutions (e.g., carrying a single base pair substitution). In particular embodiments, the HE or LHE target site cleavage assays comprise cell surface tethering of the appropriately labeled target sequence or variant target sequence prior to cleavage. In particular embodiments, binding and cleavage assays are uncoupled by affecting cell surface binding or tethering of the target sequence or variant target sequence to HE or LHE-expressing cells under conditions precluding cleavage, and subsequently and optionally adjusting the conditions to support cleavage, and assaying for such cleavage if present. Additional aspects comprise novel HE or LHE target nucleic acids comprising unique fluorophores at opposite termini, and the use thereof in flow cytometry-based cleavage assays.

Additional aspects provide methods, comprising the use of sequence specific cell surface displayed HE or LHE interactions with dsOligos under conditions which prohibit substrate cleavage to allow for physical isolation of the displaying cells by multiple cell separation methods. Particular embodiments provide methods comprising use of cell-surface displayed HE or LHE-dsOligo interactions to provide for rapid enrichment and/or viable recovery of rare HE LHE expressing cells by FACS and/or MACS. In certain aspects, such methods comprise use of both FACS and MACS.

Further aspects provide methods for high-throughput screening of cell-based libraries of cell surface-displayed HEs or LHEs, or of variants, muteins or derivatives thereof to provide for rapid identification, analysis and isolation of novel HEs or LHEs with novel sequence specificities (e.g., target DNA specificities).

Yet further aspects provide a novel method of introducing a DNA-strand cleavage event in a cell, comprising: identifying and/or isolating, using at least one of the above-described novel compositions or methods, an HE or LHE having an altered target site specificity; and introduction of the HE or LHE into a target cell having the respective DNA target, wherein target site specific cleavage is, at least in part, afforded. In particular embodiments the HE comprises an LHE, and the DNA stand cleavage comprises sequence specific double-strand cleavage. In other particular embodiments the LHE is introduced with an additional DNA sequence capable of homologously recombining with genomic DNA sequences nearby the LHE-induced double strand break.

Yet further aspects provide a novel method of isolating desired genomic DNA fragments from a cell intact with their endogenously bound regulatory proteins, comprising: identifying and/or isolating, using at least one of the above-described novel compositions or methods, an HE or LHE having an altered target site binding specificity. The HE or LHE is then optionally mutated so as to eliminate its enzymatic activity but leave intact or largely intact its sequence specific DNA binding activity. The HE or LHE or 'inactive' HE or LHE is introduced into a target cell having the respective DNA target, wherein target site specific binding is, at least in part, afforded. Art recognized chromatin immunoprecipitation methods, and targeted at the HE or LHE or inactive LE or LHE, are then used to isolate the HE or LHE or inactive HE or LHE-bound DNA fragments, the high DNA binding specificity of the inactive HE or LHE having allowed it to bind to only one or a small number of DNA sites in the target genome.

DETAILED DESCRIPTION OF THE INVENTION

Definitions

Figure 1A:
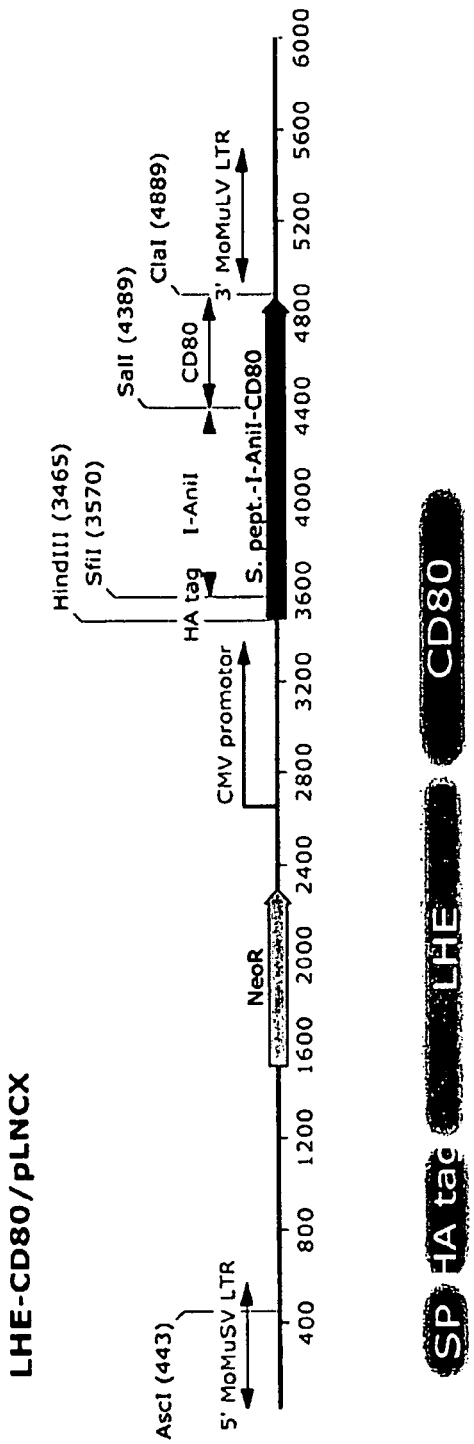
FIGS. 1a-1d show, according to particular exemplary aspects, vector schematics and validation of efficient LHE fusion protein expression in DT40 chicken B-cells.

The term "cell" as referred to herein encompasses a living organism capable of self replication, and preferably is of size sufficient to allow for separation from cells with similar properties by flow cytometry or another suitable separation technology. In particular cell embodiments (e.g., eukaryotic cells), cells contain genomic DNA in a subcellular organelle (e.g., a nucleus). In other embodiments, genomic DNA is not be contained in a nucleus (e.g., prokaryotic cells). Cells encompassed by the claimed methods include, but are not limited to culturable cells capable of cell-surface protein presentation or display, such as vertebrate or mammalian or other metazoan cells, yeast or other unicellular eukaryotic cells, bacterial or other prokaryotic cells, etc.

The term "homing endonuclease" or "HE" as used herein not only refers to art recognized HE including but not limited to known LAGLIDAG, HNH, His-Cys Box, GIY-YIG, and I-SspI-type homing endonucleases, but also to functional (sequence specific binding and/or cleaving) fusions, muteins or variants thereof. Preferably, the HEs and methods of the present invention relate to LAGLIDAG homing endonucleases. In particular aspects, the single chain LAGILDADG homing endonucleases_I-AniI (SEQ ID NO:16), H-DreI (SEQ ID NO:17; (Chain J, E-Drei (gi|27065708|pdb|1MOW|J[27065708]); Chain G, E-Drei (gi|27065705|pdb|1MOW|G[27065705]); Chain D, E-Drei (gi|27065702|pdb|1MOW|D[27065702]); Chain A, E-Drei (gi|27065699|pdb|1MOW|A[27065699]))), I-DmoI (SEQ ID N018) HEs, I-CreI (P05725; SEQ ID NO:20), and fusions, muteins or variants thereof are preferred. Homing endonucleases are proteins with enzymatic activity able to cleave a double-stranded DNA molecule, and having a polynucleotide recognition site of 14-40 bp. In preferred aspects, homing endonucleases are of the LAGLIDADG family.

"New homing endonuclease" or "homing endonuclease of altered specificity" is defined as a homing endonuclease (e.g., LAGILDADG homing endonucleases) derived from an initial homing endonuclease presenting a different or altered binding/recognition and/or cleavage specificity or activity from that of the initial one.

"Altered recognition and/or cleavage sequence" as used herein refers to a new or altered homing endonuclease binding or cleaving a double stranded DNA sequence with an altered specificity and/or efficiency (e.g., an altered efficacy of at least 2-fold, at least 5-fold, at least 10-fold more than the natural homing endonuclease, preferably at least 50-fold, more preferably at least 100-fold. The initial homing endonuclease can be a natural homing endonuclease or a modified one (e.g., derived by mutagenesis). In this context, "natural" refers to objects found in nature. For example, a homing endonuclease that is found to be naturally present in an organism, that can be isolated from a source in nature and which has not been intentionally modified by man in the laboratory.

The term "cell-surface presentation or display" of at least one HE, or fusion, mutein or variant thereof refers to display or presentation of an expressed HE, or fusion, mutein or variant thereof such that it is accessible to contact by one or more target nucleic acid molecules and/or specific binding agent (e.g., HE-specific antibodies, antigen tag-specific antibodies, etc.). Preferably, such displayed HEs are functional for sequence specific target sequence binding and/or cleavage.

The term "recombinant homing endonuclease (HE) expression system" refers to any suitable expression system that provide for cell-surface presentation or display of at least one HE, or fusion, mutein or variant thereof. Exemplary expression systems include expression vectors suitable for respective cell types, and include recombinant expressing chromosomal sites/sequences (HE sequences inserted (e.g., by homologous recombination or otherwise) into a chromosomal site to provide for HE sequence expression). For example, insertion of a HE coding sequence within an immunoglobulin light or heavy chain genomic locus is encompassed by the present conception.

"Homologous DNA sequences" are those with sufficient identity to another one to lead to a homologous recombination, having at least 95% identity, preferably 97%, and more preferably 99% identity.

"Vector" as used herein refers to a nucleic acid or composite protein/nucleic acid assembly which is capable of transporting a nucleic acid into a bacterial or eukaryotic cell. Vectors include a number of distinct types. Some types of vectors are capable of autonomous replication of nucleic acids to which they are linked. One type of preferred such vector is a "plasmid", a double stranded circular nucleic acid capable of extra-chromosomal replication in bacteria. Other types of preferred vector are viruses, protein/nucleic acid assemblages found in nature which are able to introduce their nucleic acid into prokaryotic or eukaryotic cells, and then able to replicate themselves within the cell. Derived from viruses found in nature are virus-like particles (VLP's), which are nucleic acid/protein assemblages which are able to transfer their nucleic acid, but the nucleic acid no longer includes sequences required for self replication within a cell. A number of viral vectors are described in McVey et al., U.S. Pat. No. 5,801,030, the teachings of which are incorporated herein by reference. Vectors capable of directing the expression of genes to which they are operatively linked are referred to as "expression vectors". Large numbers of suitable vectors of many types are known to those of skill in the art and are commercially available. Vectors typically include a selectable marker gene, such as neomycin phosphotransferase for eukaryotic cell culture; TRP1 for *S. cerevisiae*; and tetracycline, rifampicin or ampicillin resistance in *E. coli*.

The phrases "target site", as used within this application, is defined as referring to a distinct DNA sequence to be bound or cleaved by a homing endonuclease.

Additional embodiments, "fusion, mutein or variants", include functional (e.g., target sequence-binding and/or cleavage) variants (including conservative amino acid sequence variants as described herein, and also non-conservative amino acid sequence variants), fragments, muteins, derivatives and fusion proteins thereof. Mutant HEs and LHEs refers to amino acid variants of HEs and LHEs that have altered target sequence binding and/or cleavage activity (specificity and/or strength of binding, and/or specificity and/or cleavage activity), and includes functional (e.g., target sequence binding but non-cleaving) variants (including conservative and non-conservative amino acid sequence variants as described herein), fragments, muteins, derivatives and fusion proteins thereof. Representative, HEs and LHEs are provided herein.

Biologically Active Variants. Variants of HEs and LHEs have substantial utility in various aspects of the present invention. Variants can be naturally or non-naturally occurring. Naturally occurring variants are found in various unicellular eukaryotic, archael, and prokaryotic organisms, as well as some bacterial viruses (e.g. phage), and comprise amino acid sequences which are substantially identical to the exemplary HE and LHE amino acid sequences shown herein, and include natural sequence polymorphisms. Species homologs of the proteins can be obtained using subgenomic polynucleotides of the invention, as described below, to make suitable probes or primers for screening cDNA expression libraries from other species of the organism from which the HE or LHE was originally isolated, identifying cDNAs which encode homologs of the protein, and expressing the cDNAs as is known in the art.

Non-naturally occurring variants which retain substantially the same or altered biological activities as naturally occurring protein variants, are also included here. Preferably, naturally or non-naturally occurring variants have amino acid sequences which are at least 85%, 90%, or 95% identical to the exemplary amino acid sequences shown herein. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243:3552-59 (1969) and adopted at 37 C.F.R. §§. 1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxyl-terminal group such as COOH.

Guidance in determining which amino acid residues can be substituted, inserted, or deleted without abolishing biological or immunological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

Such substitutions may be made in accordance with those set forth in TABLE 2 as follows:

TABLE 2

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

Variants of the HEs or LHEs disclosed herein also include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins (Mark et al., U.S. Pat. No. 4,959,314).

Preferably, amino acid changes in the HE or LHE variants are conservative or non-conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect, depending upon the location of the replacement, that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of HE or LHE protein or polypeptide variants are of the same type as a protein comprising the amino acid sequence encoded by the exemplary sequences shown herein, although the properties and functions of variants can differ in degree or specificity (e.g., binding and/or cleavage).

It will be recognized in the art that some amino acid sequences of the HE and LHE polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to target nucleic acids. Thus, the HE or LHE polypeptides of the present invention may include one or more amino acid substitutions, deletions or additions, either from natural mutations or human manipulation (e.g., mutagenesis).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic (Pinckard et al., *Clin. Exp. Immunol.* 2:331-340, 1967; Robbins et al., *Diabetes* 36:838-845, 1987; Cleland et al., *Crit. Rev. Therapeutic Drug Carrier Systems* 10:307-377, 1993).

Amino acids in the HE or LHE polypeptides of the present invention that are essential for function can be identified by methods known in the art, such as site-directed mutagenesis or alanine-scanning mutagenesis (Cunningham and Wells, *Science* 244:1081-1085, 1989). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904, 1992 and de Vos et al. *Science* 255:306-312, 1992).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given HE or LHE will not be more than 50, 40, 30, 25, 20, 15, 10, 5, 3, 2 or 1. In addition, pegylation of HE or LHE polypeptides and/or muteins is expected to provide such improved properties as increased half-life, solubility, and protease resistance. Pegylation is well known in the art.

Fusion Proteins.

Fusion proteins comprising proteins or polypeptide fragments of HE or LHE polypeptide can also be constructed. Fusion proteins are useful for, inter alia, generating antibodies against amino acid sequences and for use in various targeting, expression and assay systems. For example, fusion proteins can be used to identify He or LHE proteins which interact with a target sequence of the invention or which interfere or alter HE or LHE biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the exemplary amino acid sequence shown herein or can be prepared from biologically active variants thereof. The first protein segment can include of a full-length He or LHE. Other first protein segments can consist of a limited number of contiguous amino acids.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP 16 protein fusions. CD80 fusions are a preferred fusion as disclosed herein.

These fusions can be made, for example, by covalently linking two protein segments or by standard procedures in the art of molecular biology. Recombinant DNA methods can be used to prepare fusion proteins, for example, by making a DNA construct which comprises a coding region for the exemplary protein sequences shown herein in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

The term "target" specificity as used herein refers to homing endonclease target sequence, and includes HE target sequence binding specificity and/or HE targe sequence cleavage specificity.

The term "labeled target nucleic acid sequence" refers to target nucleic acids labeled with one more labels suitable for monitoring binding or cleavage events. Such labels include, but are not limited to fluorescent labels (PE, Alexa Fluor 647, and other art-recognized labels used in FACS or MACS based separations, etc.), eptitope tags, biotin, streptavidin, radiolabels, FRET labels, etc. Labeled target nucleic acid sequences include bifluorescent double stranded sequences, examples of which are described herein.

The term "selecting" as used herein refers to any method suitable for separating cells based on cell-surface presentation or display of HEs. Exemplary methods include, but are not limited to magnetic activated cells sorting (MACS), fluorescence activated cell sorting (FACS), or combinations thereof (e.g., using labeled target nucleic acids).

Figure 5A:
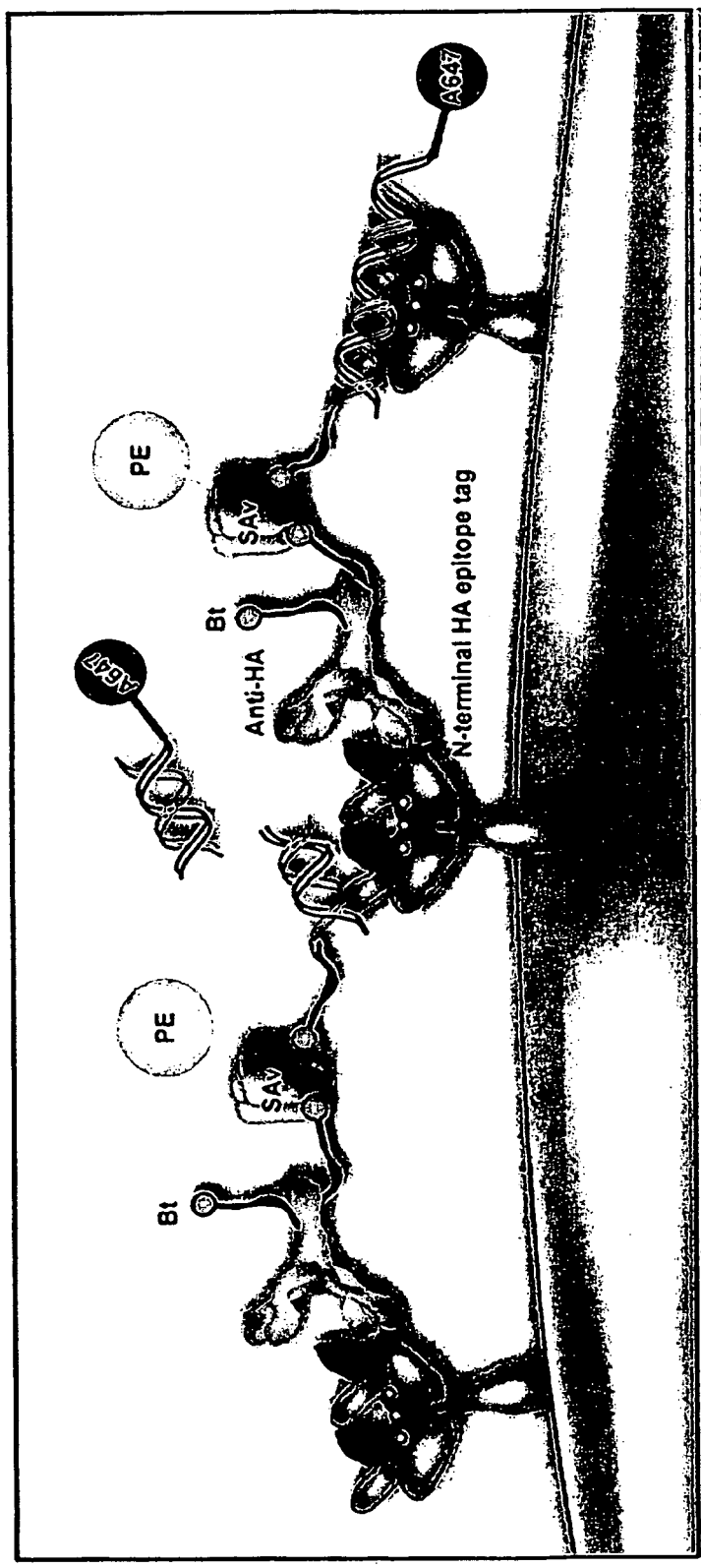
FIGS. 5a-5e show, according to particular exemplary aspects, data confirming sequence-specific, LHE-mediated cleavage of cell surface-tethered dsOligo substrates conjugated with distinct fluorophores at opposite termini.

The term "tethered target sequence" as used herein refers to binding of one or more target sequences to the cell surface by means other than binding to the cell surface expressed HE target sequence binding site, to provide for subsequent binding and/or cleavage by the HE target sequence binding and/or cleavage site. In particular aspects of the methods, one end of the labeled target sequence is tethered to the cell surface, and the other end of the target sequence comprises a label which is releasable upon subsequent homing endonuclease-mediated cleavage of the tethered target sequence. For example, as described herein, cells may first labeled with a biotin-conjugated anti-HA monoclonal antibody (α-HA-BT) followed by the addition of pre-formed 647-dsAni1-BT:SAv-PE complexes which contain an average of three remaining BT-binding sites per SAv tetramer, and this exemplary staining protocol serves to tether the 647-dsAni1-BT:SAv-PE to the cell surface independent of any specific LHE-dsOligo interaction, yet still placing the dsOligo within the LHE's immediate environment (FIG. 5a). Thus, according to particular exemplary aspects, cleavage events can be followed using an α-HA-BT tethered dually-fluorescent labeled dsOligos and the release of Alexa Fluor 647 following addition of $Mg^{2+}$ (to provide for cleavage conditions). Therefore, the presently disclosed inventive aspects encompass the conception that where the tethered double labeled oligos can be cleaved by the surface LHE, the cells would lose the fluorescence signal contribution from one label (e.g., Alexa Fluor 647) yet retain signal from the other label (e.g., a tightly bound bridging SAv-PE).

Preferred Exemplary Embodiments

Cells and Cell Libraries Comprising Cell-Surface Presentation or Display of at Least One HE:

Particular embodiments of the present invention provide a cell, comprising at least one recombinant homing endonuclease (HE) expression system suitable to provide for cell-surface presentation or display of at least one HE, or fusion, mutein or variant thereof on the cell. In certain aspects, the cell expresses a single homing endonuclease (HE), or fusion, mutein or variant thereof on the cell surface. In additional aspects, the cell expresses a plurality of different homing endonuclease (HE), or fusions, muteins or variants thereof on the cell surface.

Also provided, is a library of cells, comprising a plurality of cells, wherein each cell comprises at least one recombinant homing endonuclease (HE) expression system suitable to provide for cell-surface presentation or display of at least one HE, or fusion, mutein or variant thereof on the cell, and wherein a plurality of different homing endonuclease (HE), or fusions, muteins or variants thereof are represented between and among the cells of the library. Preferably, in the inventive cells and libraries thereof, the homing endonuclease is functional for at least one of binding of nucleic acid target sequence, and cleaving of a nucleic acid target sequence.

In particular aspects of the cell or library thereof, the homing endonuclease (HE) is expressed as a fusion protein suitable to provide for cell-surface presentation or display of the at least one HE, or fusion, mutein or variant thereof. In certain embodiments, the fusion protein comprises at least one of a signal peptide, an epitope tag, a membrane-anchoring moiety or polypeptide, and combinations thereof. In certain embodiments, the signal peptide is an immunoglobulin signal peptide, and the membrane anchoring polypeptide comprises murine CD80 or a membrane anchoring portion thereof. In additional embodiments, the signal peptide is an immunoglobulin signal peptide, and the membrane anchoring polypeptide comprises a mature immunoglobulin light or heavy chain polypeptide or a membrane-anchoring portion thereof.

In particular aspects of the cell or library thereof, the recombinant expression comprises expression from at least one recombinant expression vector, or from at least one recombinant genomic locus. In particular embodiments, recombinant expression of the homing endonuclease (HE), comprises insertion of a HE coding sequence within an immunoglobulin light or heavy chain genomic locus. In particular aspects of the cell or library thereof, the one or more cells comprise at least one cell selected from the group consisting of a eukaryotic cell, a culturable metazoan cell capable of cell-surface protein presentation or display, mammalian cell, yeast cell and bacterial cell.

In particular aspects of the cell or library thereof, the homing endonuclease comprises at least one selected from the group consisting of LAGLIDAG, HNH, His-Cys Box, GIY-YIG, I-SspI-type, and fusions, muteins or variants thereof. Preferably, the homing endonuclease comprises or consists of a LAGLIDAG homing endonuclease, or a fusion, mutein or variant thereof. In particular embodiments, the homing endonuclease comprises or consists of at least one selected from the group consisting of I-AniI, H-DreI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, and fusions, muteins or variants thereof. In certain aspects, the homing endonuclease comprises or consists of I-AniI, or a fusion, mutein or variant thereof. In additional aspects, the homing endonuclease comprises or consists of H-DreI, or a fusion, mutein or variant thereof.

Methods for Identifying a Homing Endonuclease with a Desired Target Specificity:

Binding.

Additional embodiments provide a method for identifying a homing endonuclease with a desired target specificity, comprising: expressing, using a suitable recombinant expression system, at least one homing endonuclease (HE) in one or more cells, the recombinant expression and the one or more cells suitable to provide for cell-surface to presentation or display of the at least one HE; contacting the one or more expressing cells with at least one labeled target nucleic acid sequence under conditions suitable to allow for target sequence binding to the at least one cell-surface HE; and selecting, based on the presence of cell-bound label, one or more cells expressing at least one cell surface HE having a target sequence binding specificity. In particular aspects of the above methods, the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented.

Binding and/or Cleavage.

Further embodiments provide a method for identifying a homing endonuclease with a desired target specificity, comprising: expressing, using a suitable recombinant expression system, at least one homing endonuclease (HE) in one or more cells, the recombinant expression and the one or more cells suitable to provide for cell-surface presentation or display of the at least one HE; contacting the one or more expressing cells with at least one labeled target nucleic acid sequence under conditions suitable to allow for target sequence binding to the at least one cell-surface HE; adjusting the conditions to allow for homing endonuclease-mediated cleavage of the target sequence; and selecting, based on a decrease of cell-bound label, one or more cells expressing at least one cell surface HE having a target sequence cleaving specificity. In certain aspects of the above methods, the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented. In particular aspects of the methods, contacting comprises tethering one end of the labeled target sequence to the cell surface, and wherein the other end of the target sequence comprises a label which is releasable upon subsequent homing endonuclease-mediated cleavage of the tethered target sequence. In particular embodiments, the conditions suitable to allow for target sequence binding do not allow for target sequence cleavage by the homing endonuclease (HE). In certain embodiments, the conditions comprise concentrations of calcium and/or copper ions sufficient to allow for target sequence binding, but lack a concentration of at least one of magnesium, cobalt, manganese, nickel and zinc ions sufficient to allow for target sequence cleavage. In particular aspects, conditions that allow for homing endonuclease-mediated cleavage of the target sequence comprise a concentration of at least one of magnesium, cobalt, manganese, nickel and zinc ions sufficient to allow for target sequence cleavage, and a concentration of calcium and/or copper ions below a level that significantly inhibits target sequence cleavage.

In particular embodiments of the above methods, the homing endonuclease (HE) is expressed as a fusion protein suitable to provide for cell-surface presentation or display of the at least one HE, or fusion, mutein or variant thereof. In certain aspects of the methods, the fusion protein comprises at least one of a signal peptide, an epitope tag, a membrane-anchoring moiety or polypeptide, and combinations thereof. In certain aspects, the signal peptide is an immunoglobulin signal peptide, and the membrane anchoring polypeptide comprises murine CD80 (e.g., SEQ ID NOS:21, 22) or a membrane anchoring portion thereof. In additional aspects, the signal peptide is an immunoglobulin signal peptide, and the membrane anchoring polypeptide comprises a mature immunoglobulin light or heavy chain polypeptide or a membrane-anchoring portion thereof.

In particular embodiments of the methods, the recombinant expression comprises expression from at least one recombinant expression vector, or from at least one recombinant genomic locus. In certain aspects, recombinant expression of the homing endonuclease (HE), comprises insertion of a HE coding sequence within an immunoglobulin light or heavy chain genomic locus.

In particular embodiments of the methods, the one or more cells comprise at least one cell selected from the group consisting of a eukaryotic cell, a culturable metazoan cell capable of cell-surface protein presentation or display, mammalian cell, yeast cell and bacterial cell. In particular embodiments of the methods, each one of the one or more cells expresses a single homing endonuclease (HE) sequence. In additional embodiments, at least one of the one or more cells expresses a plurality of different homing endonuclease (HE) sequences.

In particular embodiments of the methods, selecting comprises the use of magnetic activated cells sorting (MACS), fluorescence activated cell sorting (FACS), or combinations thereof.

In certain embodiments, the target sequence comprises a known or putative homing endonuclease (HE) binding sequence. In additional embodiments, the target sequence comprises a known or putative homing endonuclease (HE) and a known or putative homing endonuclease cleavage sequence.

In particular embodiments of the methods, the homing endonuclease comprises at least one selected from the group consisting of LAGLIDAG, HNH, His-Cys Box, GIY-YIG, I-SspI-type, and fusions, muteins or variants thereof. Preferably, the homing endonuclease comprises or consists of a LAGLIDAG homing endonuclease, or a fusion, mutein or variant thereof. In certain aspects, the homing endonuclease comprises or consists of at least one selected from the group consisting of I-AniI, H-DreI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, and fusions, muteins or variants thereof. In particular aspects, the homing endonuclease comprises or consists of I-AniI, or a fusion, mutein or variant thereof. In additional aspects, the homing endonuclease comprises or consists of H-DreI, or a fusion, mutein or variant thereof.

Methods for Obtaining and Identifying a Variant Homing Endonuclease with an Altered Target Specificity:

Altered Target Binding Specificity.

Further embodiments provide a method for obtaining and identifying a variant homing endonuclease with an altered target specificity, comprising: obtaining a nucleic acid sequence encoding an open reading frame for at least one initial homing endonuclease (HE); expressing, using a suitable recombinant expression system, at least one variant of the nucleic acid sequence in one or more cells, the recombinant expression suitable to provide for cell-surface presentation or display of the at least one HE in the one or more cells, the at least one variant sequence having been derived by mutagenesis from the nucleic acid sequence encoding the initial homing endonuclease (HE); contacting the one or more expressing cells with at least one labeled target nucleic acid sequence under conditions suitable to allow for target sequence binding to the at least one cell-surface HE; and selecting, based on the presence of cell-bound label, one or more cells expressing at least one cell surface variant HE having a target sequence binding specificity. In certain aspects of the methods, the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented.

Altered Target Cleavage Specificity.

Yet additional embodiments provide a method for obtaining and identifying a variant homing endonuclease with an altered target specificity, comprising: obtaining a nucleic acid sequence encoding an open reading frame for at least one initial homing endonuclease (HE); expressing, using a suitable recombinant expression system, at least one variant of the nucleic acid sequence in one or more cells, the recombinant expression suitable to provide for cell-surface presentation or display of the at least one HE in the one or more cells, the at least one variant sequence having been derived by mutagenesis from the nucleic acid sequence encoding the initial homing endonuclease (HE); contacting the one or more expressing cells with at least one labeled target nucleic acid sequence under conditions suitable to allow for target sequence binding to the at least one cell-surface HE; adjusting the conditions to allow for homing endonuclease-mediated cleavage of the target sequence; and selecting, based on a decrease of cell-bound label, one or more cells expressing at least one cell surface HE having a target sequence cleaving specificity. In certain aspects of the methods, the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented. In certain embodiments, contacting comprises tethering one end of the labeled target sequence to the cell surface, and wherein the other end of the target sequence comprises a label which is releasable upon subsequent homing endonuclease-mediated cleavage of the tethered target sequence. In particular embodiments, the conditions suitable to allow for target sequence binding do not allow for target sequence cleavage by the homing endonuclease (HE). In certain aspects, the conditions comprise concentrations of calcium and/or copper ions sufficient to allow for target sequence binding, but lack a concentration of at least one of magnesium, cobalt, manganese, nickel and zinc ions sufficient to allow for target sequence cleavage. In particular aspects, conditions that allow for homing endonuclease-mediated cleavage of the target sequence comprise a concentration of at least one of magnesium, cobalt, manganese, nickel and zinc ions sufficient to allow for target sequence cleavage, and a concentration of calcium and/or copper ions below a level that significantly inhibits target sequence cleavage.

In certain embodiments of the above methods, the homing endonuclease (HE) is expressed as a fusion protein suitable to provide for cell-surface presentation or display of the at least one HE, or fusion, mutein or variant thereof. In particular aspects, the fusion protein comprises at least one of a signal peptide, an epitope tag, a membrane-anchoring moiety or polypeptide, and combinations thereof. In certain embodiments, the signal peptide is an immunoglobulin signal peptide, and the membrane anchoring polypeptide comprises murine CD80 (e.g., SEQ ID NOS:21, 22) or a membrane anchoring portion thereof. In other embodiments, the signal peptide is an immunoglobulin signal peptide, and the membrane anchoring polypeptide comprises a mature immunoglobulin light or heavy chain polypeptide or a membrane-anchoring portion thereof.

In particular implementations, the recombinant expression comprises expression from at least one recombinant expression vector, or from at least one recombinant genomic locus. In certain aspects, recombinant expression of the homing endonuclease (HE) comprises insertion of a HE coding sequence within an immunoglobulin light or heavy chain genomic locus.

In particular embodiments of the methods, the one or more cells comprise at least one cell selected from the group consisting of a eukaryotic cell, a culturable metazoan cell capable of cell-surface protein presentation or display, mammalian cell, yeast cell and bacterial cell. In certain aspects, each one of the one or more cells expresses a single homing endonuclease (HE) sequence. In additional aspects, at least one of the one or more cells expresses a plurality of different homing endonuclease (HE) sequences.

In certain implementations, selecting comprises the use of magnetic activated cells sorting (MACS), fluorescence activated cell sorting (FACS), or combinations thereof.

In certain embodiments, the target sequence comprises a known or putative homing endonuclease (HE) binding sequence. In additional aspects, the target sequence comprises a known or putative homing endonuclease (HE) and a known or putative homing endonuclease cleavage sequence.

In various aspects, the homing endonuclease comprises at least one selected from the group consisting of LAGLIDAG, HNH, His-Cys Box, GIY-YIG, I-SspI-type, and fusions, muteins or variants thereof. Preferably, the homing endonuclease comprises or consists of a LAGLIDAG homing endonuclease, or a fusion, mutein or variant thereof. In certain aspects, the homing endonuclease comprises or consists of at least one selected from the group consisting of I-AniI, H-DreI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-MfI I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, and fusions, muteins or variants thereof. In particular embodiments, the homing endonuclease comprises or consists of I-AniI, or a fusion, mutein or variant thereof. In additional embodiments, the homing endonuclease comprises or consists of H-DreI, or a fusion, mutein or variant thereof.

Methods for Introducing a Targeted Double-Strand Break in the Genome of a Virus or of a Living Cell:

Particular aspects provide a method for introducing a targeted double-strand break in the genome of a virus or of a living cell, comprising: obtaining a homing endonuclease selected using at least one cell, cell library or method comprising cell-surface presentation or display of at least one homing endonuclease (HE), or fusion, mutein or variant thereof on the cell or libraries to provide a homing endonuclease having a specific, desired DNA target cleavage specificity within a target viral or cellular genome; and introducing the homing endonuclease into a cell harboring the respective target viral or cellular genome, wherein the homing endonuclease introduces a targeted double-strand break in the viral or cellular genome.

Methods for Chromatin Immunoprecipitation (CHIP):

Additional aspects provide a method for chromatin immunoprecipitation (CHIP), comprising: obtaining a homing endonuclease selected using at least one cell, cell library or method comprising cell-surface presentation or display of at least one homing endonuclease (HE), or fusion, mutein or variant thereof on the cell or libraries to provide a homing endonuclease having a specific, desired DNA target cleavage specificity within a target viral or cellular genome; and introducing into a cell the homing endonuclease or an epitope-tagged version thereof to provide for specific homing endonuclease complexes within a target viral or cellular genome. In certain aspects, the methods additionally comprise: crosslinking of the genomic DNA and associated proteins to provide for crosslinking of the homing endonuclease to its cognate bound target site; shearing of the crosslinked genomic DNA; and immunoprecipitating the homing endonuclease and its bound DNA fragment using antibodies to the homing endonuclease or to the epitope tag thereof.

In particular aspects of the above methods, introducing the homing endonuclease comprises introducing the homing endonuclease as a polypeptide linked to one or more subcellular localization peptides necessary or sufficient to target the LHE to an appropriate organellar compartment. In additional embodiments, introducing the homing endonuclease comprises introducing the homing endonuclease in the context of a suitable expression vector under the control of appropriate transcriptional regulatory elements. In yet additional aspects, introducing the homing endonuclease comprises introducing the homing endonuclease or a sequence or vector encoding the homing endonuclease, along with an appropriate vehicle, carrier or DNA fragment. In additional implementations, introducing the homing endonuclease comprises incorporating the homing endonuclease or a sequence encoding the homing endonuclease into one or more viral particles. Preferably the virus does not integrate into the host cell genome. Preferably, the virus particle is an integrase-deficient lentiviral particle, or an HIV-1 derived lentiviral particle.

Use of CD80 for Cell Surface Expression of HE Fusion Proteins:

Particular aspects provide the use of a CD80 nucleic acid or protein sequence, or a portion thereof for cell surface expression of homing endonucleases (HEs) or LAGLIDAG homing endonuclease (LHEs) (see working Examples described herein).

Use of DT40 Cell Lines. Chicken Tumor Cell Lines or Lymphocyte Cell Lines for Cell Surface Expression of HE Fusion Proteins:

Use of a DT40 cell line specifically, suitable chicken tumor cell line or a lymphocyte cell line for cell surface expression of homing endonucleases (HEs) or LAGLIDAG homing endonuclease (LHEs) (see working Examples described herein). In particular embodiments, B-lymphocyte cell lines are used so as to allow the HEs to be subject to the endogenous hypermutation mechanism of B-lymphocytes.

Generation of Homing Endonuclease Variants:

Particular aspects of the present invention provide a method for identifying a homing endonuclease (e.g., HE or LHE) specific to a targeted DNA sequence from a library of homing endonucleases of various specificities. These may be generated from an initial homing endonuclease which is a natural homing endonuclease. Alternatively, the initial HE or LAGLIDADG homing endonuclease is not a natural one. In preferred embodiments, said LAGLIDADG homing endonucleases are used (e.g., I-AniI or E-DreI). The methods comprises placing a library of homing endonuclease variants on the surface of a cell, and selection and/or screening of the variants able to bind and/or cleave a desired target DNA sequence or part thereof.

In particular aspects, the homing endonucleases are expressed on the surface of cells through fusion with one of several surface-bound cell proteins known to those skilled in the art. Said protein may be a yeast protein, as described as a general approach for yeast protein surface expression (this general method is reviewed in Chao et al, Nature Protocols, 2006, 1(2):755-768), murine CD80, as described as a method for expressing antibody fragments (Chou et al, Biotechnol Bioeng, 1999, 65:1690-169; also Liao et al, Biotechnol Bioengin, 2001, 73:313-323), or an immunoglobulin heavy or light chain, as described for glucoamylase as a means for directing soluble immunoglobulin proteins to a secretory pathway in *Aspergillus nigrans* (Ward et al, Applied and Environmental Microbiology, 2004, 70(5): 2567-2576), but readily modifiable for surface expression of a fusion protein via fusion to surface expressed forms of immunoglobulins.

In certain embodiments, the cell based library of surface expressed homing endonuclease variants is then exposed to a fluorescent labeled oligonucleotide under conditions in which binding of the oligonucleotide (e.g., target sequence), and optionally subjected to a cell sorting protocol based on target sequence binding.

Generation of the library of homing endonuclease (HE) (e.g., homing endonuclease) of different target specificities can be performed by any of various art recognized methods, including DNA shuffling, error-prone PCR and expression of the homing endonuclease in a cell line in which the gene is susceptible to mutation. Preferably, the diversity is introduced by targeted mutagenesis (e.g., cassette mutagenesis, oligonucleotide directed codon mutagenesis, targeted random mutagenesis), by random mutagenesis (e.g., mutator strains, *Neurospora crassa* system (U.S. Pat. No. 6,232,112; WO01/70946, error-prone PCR), by DNA shuffling, by directed mutation or a combination of these technologies (See Current Protocols in Molecular Biology, Chapter 8 "Mutagenesis in cloned DNA", Eds Ausubel et al., John Wiley and Sons). The HE variants are preferably prepared by the targeted mutagenesis of an initial HE. The diversity is optimally introduced at positions of the residues contacting the DNA target or interacting (directly or indirectly) with the DNA target. The diversity is preferably introduced in regions interacting with the DNA target, and more preferably introduced at the positions of the interacting amino acids. In libraries generated by targeted mutagenesis, amino acid residues (e.g., selected from the standard 20 amino acids) can be introduced at the chosen variable positions. Preferably, the amino acids present at the variable positions are the amino acids well-known to be generally involved in protein-DNA interaction. More particularly, these amino acids are generally the hydrophilic amino acids. More preferably, the amino acids present at the variable positions comprise D, E, H, K, N, Q, R, S, T, Y. Optionally, the amino acids present at the variable positions are selected from the group consisting of D, E, H, K, N, Q, R, S, T, Y. Synthetic or modified amino acids may also be used.

One preferred way to generate a directed library is the use of degenerated codons at the positions where diversity has to be introduced. Several types of degenerated codons could be used. A degenerated codon N N K ([ATCG] [ATCG] [TG]) leads to 32 different codons encoding the 20 amino acids and one stop. A degenerated codon N V K ([ATCG] [ACG] [TG]) leads to 24 different codons encoding the 15 amino acids and one stop. A degenerated codon V V K ([ACG] [ACG] [TG]) leads to 18 different codons encoding the 12 amino acids (A, D, E, G, H, K, N, P, Q, R, S, T) and no stop. A degenerated codon R V K ([AG] [ACG] [TG]) leads to 12 different codons encoding the 9 amino acids (A, D, E, G, K, N, R, S, T). Preferably, a degenerated codon V V K ([ACG] [ACG] [TG]) leading to 18 different codons encoding the 12 amino acids (A, D, E, G, H, K, N, P, Q, R, S, T) is used for generating the library. Indeed, the V V K degenerated codon does not contain any stop codon and comprises all the hydrophilic amino acids.

If a directed library is generated, knowledge on amino acids interacting with the DNA target is useful. This knowledge could be provided, for example, by X-ray cristallography, Alanine scanning, or cross-linking experiments. The amino acids interacting with the DNA target can also be deduced by sequence alignment with a homologous protein.

The custom-made or mutagenized and selected HE is derived from any initial HE. Optionally, the initial HE is selected so as its natural recognition and cleavage site is the closest to the targeted DNA site. Preferably, the initial HE is a homing endonuclease, as specified herein. Homing endonucleases fall into 4 families on the basis of well conserved amino acid motifs, namely the LAGLIDADG family, the GIY-YIG family, the His-Cys box family, and the HNH family (Chevalier et al., 2001, N.A.R, 29, 3757-3774). The detailed three-dimensional structures of several homing endonucleases are known, namely I-Dmo I, PI-Sce I, PI-Pfu I, I-Cre I, I-Ppo I, and a hybrid homing endonuclease I-Dmo I/I-Cre I called E-Dre I (Chevalier et al., 2001, Nat Struct Biol, 8, 312-316; Duan et al., 1997, Cell, 89, 555-564; Heath et al., 1997, Nat Struct Biol, 4, 468-476; Hu et al., 2000, J Biol Chem, 275, 2705-2712; Ichiyanagi et al., 2000, J Mol Biol, 300, 889-901; Jurica et al., 1998, Mol Cell, 2, 469-476; Poland et al., 2000, J Biol Chem, 275, 16408-16413; Silva et al., 1999, J Mol Biol, 286, 1123-1136; Chevalier et al., 2002, Molecular Cell, 10, 895-905).

The LAGLIDADG family is the largest family of proteins clustered by their most general conserved sequence motif: one or two copies of a twelve-residue sequence: the di-dodecapeptide, also called LAGLIDADG motif Homing endonucleases with one dodecapeptide (D) are around 20 kDa in molecular mass and act as homodimer. Those with two copies (DD) range from 25 kDa (230 AA) to 50 kDa (HO, 545 AA) with 70 to 150 residues between each motif and act as monomer. Cleavage is inside the recognition site, leaving 4 nt staggered cut with 3'OH overhangs. I-Ceu I, and I-Cre I illustrate the homodimeric homing endonucleases with one Dodecapeptide motif (mono-dodecapeptide). I-Dmo I, I-Sce I, PI-Pfu I and PI-Sce I illustrate monomeric homing endonucleases with two Dodecapeptide motifs.

The initial LAGLIDADG homing endonuclease can be selected from the group consisting of: I-AniI, H-DreI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I; PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Cre I, I-Csm I, PI-Sce I, PI-Pfu I, PI-Tli I, PI-Mtu I, and I-Ceu I. In particular aspects, I-AniI, H-DreI, I-Dmo I, I-Cre I, PI-Sce I, and PI-Pfu I are selected. In additional aspects, I-AniI, H-DreI, I-Cre I are selected. In further aspects, I-AniI and H-DreI are selected.

As reviewed in US 2006/0153826 (incorporated by reference herein in its entirety) (see also Stoddard, Quarterly Reviews of Biophysics, pages 1-47, 2005; Homing endonuclease structure and function; incorporated by reference herein in its entirety), the four structures of LAGLIDADG homing endonucleases, namely those of 1-Dmo I, PI-Sce I, PI-Pfu I, and I-Cre I, reveal the functional significance of the LAGIDADG motif, and the nature of the DNA-binding interface. The core αββαββα fold of the homodimer homing endonuclease is repeated twice in the monomer homing endonuclease and confers upon the monomer a pseudo-dimeric structure. The first α-helix of each domain or subunit contains the defining LAGLIDADG motif. The two LAGLIDADG helices of each protein form a tightly packed dimer or domain interface. The DNA binding interface is formed by the four. β-strands of each domain or subunit that fold into an antiparallel β-sheet. A minimal DNA binding moiety could be defined in the LAGLIDADG homing endonucleases as a β-hairpin (2 β-strands connected by a loop or turn), two such β-hairpins being connected into the 4-stranded β-sheet.

Each domain or subunit interacts with a half recognition site. The external quarter recognition site can be defined by its interaction with only one of the 2 β-hairpins of each domain or subunit. Therefore, HE variants derived from LAGLIDADG homing endonuclease can be fragmented in several directed libraries. This fragmented approach for the evolution of an initial HE allows the introduction of a greater diversity (more amino acids at a position and/or more diversificated positions). In each library, the diversity is optionally introduced only in the region involved in the interaction with a half or a quarter recognition site, the targeted DNA being modified only for the part interacting with the region comprising the introduced diversity. More particularly, if a new half site is searched for, then the diversity is optionally introduced in the 4-stranded β-sheet of one domain or subunit, more preferably at the positions of the DNA interacting amino acids in this structure. If a new quarter site is searched for, then the diversity is introduced in the corresponding β-hairpin, more preferably at the positions of the DNA interacting amino acids of this structure.

In particular aspects, a library or set of libraries covers the entire targeted DNA site. Hence, if the library or libraries comprise diversity only in the region interacting with a half-site, at least two libraries, preferably two, may be used. However, if the initial HE is a dimer, one library may suffice with a half-site approach. If the libraries comprise diversity only in the region interacting with a quarter site, at least four libraries, preferably four, are, may be used. If the initial HE is a dimer, two libraries may suffice with a quarter site approach.

In particular aspects, after the selection or screening of the primary libraries, the selected elements from the primary libraries are fused or combined in a subsequent library for a new cycle of selection. For example, two libraries can be fused by shuffling. A new cycle of selection could be then done on the whole targeted DNA site. Optionally, the new cycle of selection can be done on a half targeted DNA site if the first libraries are based on a quarter site. Subsequently, the results of the selection and/or screening of the half site are combined to give a final library which can be screened for the whole targeted DNA site. Alternatively, the best elements from each libraries are joined together in order to obtain an HE able to bind and cleave the targeted DNA site.

In additional aspects, a library with diversity located only in the region involved in the interaction with a half or a quarter recognition site may be prepared. After selection or screening of this library, the selected elements from the library are modified to introduce diversity in another region involved in the interaction with recognition site, leading to a subsequent library. Libraries are generated until the complete targeted DNA site is bound and cleaved by the selected HE. In particular aspects, for a dimeric homing endonuclease (such as I-Cre I and I-Ceu I), a library can be generated by introducing diversity only in the region interacting with a half-site, a half site corresponding to one monomer of the initial homing endonuclease. This library can be used for selection and/or screening on each half sites of the target DNA sequence. When positive elements from the library have been selected for each half sites, a variant for the first half site and a variant for the other half site are brought together for binding and cleaving the whole target DNA sequence. Alternatively, the positive variants can be introduced in a single chain HE structure. A single chain HE may comprise an enzyme in which the two monomers of an initial dimeric homing endonuclease are covalently bound by a linker. If an approach by a quarter site is chosen from an initial dimer homing endonuclease, at least two libraries are generated by introducing diversity only in the region involved in the interaction with each quarter recognition sites. After the selection or screening of the primary libraries, the selected variants from the primary libraries are fused in a subsequent library for a new cycle of selection on the half site. Alternatively, the best elements from each libraries are joined together to obtain a monomer able to bind the half site. Otherwise, a library with diversity only in the region involved in the interaction with a quarter recognition site is prepared. Then, after selection or screening of this library, the selected elements from the library are modified such as to introduce diversity in the region involved in the interaction with the other quarter site, leading to a subsequent library. The selection and/or screening of this second library leads to the variant monomers able to bind the half site. When positive elements from the library have been selected for each half sites, a variant for the first half site and a variant for the other half site are brought together for binding and cleaving the target DNA sequence. Alternatively, the positive variants can be introduced in a single chain meganuclease structure. Preferably, the custom-made HE which recognizes and cleaves a desired polynucleotide target is derived from the directed evolution of a homing endonuclease. Where the homing endonuclease is a homodimer, the approach is preferably based either on the half recognition site or on the quarter site.

In a preferred embodiment, the homing endonuclease sequence is integrated into a locus (e.g., insertion of a HE coding sequence within an immunoglobulin light or heavy chain genomic locus) in a cultured vertebrate B-lymphocyte cell line which causes it to become subject to the endogenous hypermutation mechanism present in that cell line, allowing a library of homing endonucleases to be created by expansion of the B-cells in tissue culture.

Selection and Screening:

New homing endonucleases can be identified by their capacity to bind the target DNA sequence and/or their ability to cleave it.

In particular embodiments, the method comprises the following steps or combinations, ordered variants or interactions thereof:

one or more selection steps for ability to bind a target DNA sequence;

optionally one or more selection steps for cleavage activity;

optional generation of a new library of homing endonucleases based on the output of the above selection steps; and optional iteration of the one of more above steps or combinations until a homing endonuclease with the desired binding and/or cleavage specificity is obtained.

In particular aspects, selection is performed using a DNA region comprising a double stranded cleavage site. In particular aspects, the targeted sequences comprise at least 15 nucleotides, preferably 18 to 40, more preferably 18 to 30 nucleotides. In case of dimeric HEs, the targeted DNA polynucleotide can be reduced to at least 8 nucleotides for binding only. Preferably, the targeted DNA polynucleotide length is less than 10 kb, preferably less than 3 kb, more preferably less than 1 kb. For the DNA binding assay, the targeted DNA polynucleotide length is preferably less than 500 bp, more preferably less than 200 bp.

Any targeted sequence can be used to screen/select a respective HE able to cleave it. Optionally, the targeted sequence is chosen such as to present the most identity with the original recognition and cleavage site of the initial HE. Therefore, in particular mutagenesis approaches, the DNA region in which a double stranded break has to be introduced is analyzed to choose at least 1, 2, 3 or 5 sequences of at least 15 nucleotides length, preferably 18 to 40, more preferably 18 to 30 nucleotides, having at least 25% identity, preferably 50% identity and more preferably 75% identity with the original recognition and cleavage site of the initial meganuclease.

The targeted DNA sequence is adapted to the type of HE variant library. If the library is based on a half site approach, the targeted DNA sequence used for the selection/screening comprises one half original site and one half site of the desired DNA sequence. If the library is based on a quarter site approach, the targeted DNA sequence used for the selection/screening comprises three quarters of the original site and one quarter site of the desired DNA sequence The HE variants resulting from the selection and/or screening steps could optionally be an input for another cycle of diversity introduction. The positive homing endonuclease variants selected by the selection and/or screening steps are preferably validated using an in vitro and/or ex vivo cleavage assay.

The targeted DNA sequence can be immobilized on a solid support. Said solid support could be a column, paramagnetic beads or a well of a microplate. For example, the polynucleotides comprising the targeted DNA sequence present a ligand (such as a biotin) at one end, said ligand allowing the immobilization on a solid support bearing the target of the ligand (for example, streptavidin if biotin is used).

In particular aspects, selected HE variants are cloned (e.g. subcloned into an expression vector). Optionally, the nucleotide sequences encoding the selected HE variants are determined, thereby identifying of the HE variants able to bind the targeted DNA sequence.

In particular aspects, the selection and screening of homing endonuclease (HE) variants based on target sequence binding capacity is be made under conditions that are not compatible with the HE cleavage activity. For example, as described in more detail elsewhere herein, homing endonucleases typically require manganese or magnesium for cleavage activity. Therefore, according to particular aspect, binding assays for HE and LHE and variants thereof are performed without manganese or magnesium (or with levels of these that do not support cleavage). In particular aspects, manganese or magnesium is replaced by calcium, preferably calcium at a level that does not preclude subsequently adjusting the reaction conditions to promote cleavage (e.g., by subsequently adding manganese or magnesium).

Selection Based on Binding Property of Homing Endonuclease:

The binding selection assay is based on the enrichment of the homing endonuclease variants able to bind the targeted DNA polynucleotide. Therefore, the homing endonuclease variants encoded by the library are incubated with an immobilized targeted DNA polynucleotide so that homing endonuclease variants that bind to the immobilized targeted DNA polynucleotide can be differentially partitioned from those that do not present any binding capacity. The homing endonuclease variants which are bound to the immobilized targeted DNA polynucleotide are then recovered and amplified for a subsequent round of affinity enrichment and amplification. After several rounds of affinity enrichment and amplification, the library members that are thus selected can be isolated. Optionally, the nucleotide sequences encoding the selected homing endonuclease variants are determined, thereby identifying of the homing endonuclease variants able to bind the targeted DNA sequence.

Screening Based on Binding Property of Homing Endonuclease:

In particular embodiments, homing endonuclease variants are tested for their binding capacity, and particular aspects provide a method, comprising: obtaining a nucleic acid sequence encoding an open reading frame for at least one initial homing endonuclease (HE); expressing, using a suitable recombinant expression system, at least one variant of the nucleic acid sequence in one or more cells, the recombinant expression suitable to provide for cell-surface presentation or display of the at least one HE in the one or more cells, the at least one variant sequence having been derived by mutagenesis from the nucleic acid sequence encoding the initial homing endonuclease (HE); contacting the one or more expressing cells with at least one labeled target nucleic acid sequence under conditions suitable to allow for target sequence binding to the at least one cell-surface HE; and selecting, based on the presence of cell-bound label, one or more cells expressing at least one cell surface variant HE having a target sequence binding specificity. In particular library screening embodiments, the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented.

Selection and/or Screening Based on Cleavage Property of the Homing Endonuclease:

In particular embodiments, the selected homing endonuclease variants have to be tested for their cleavage capacity. Therefore, said homing endonuclease variants are incorporated in a cleavage selection and/or screening experiment, preferably an in vivo or an in vitro cleavage assay.

Certain embodiments provide a method for obtaining and identifying a variant homing endonuclease with an altered target specificity, comprising: obtaining a nucleic acid sequence encoding an open reading frame for at least one initial homing endonuclease (HE); expressing, using a suitable recombinant expression system, at least one variant of the nucleic acid sequence in one or more cells, the recombinant expression suitable to provide for cell-surface presentation or display of the at least one HE in the one or more cells, the at least one variant sequence having been derived by mutagenesis from the nucleic acid sequence encoding the initial homing endonuclease (HE); contacting the one or more expressing cells with at least one labeled target nucleic acid sequence under conditions suitable to allow for target sequence binding to the at least one cell-surface HE; adjusting the conditions to allow for homing endonuclease-mediated cleavage of the target sequence; and selecting, based on a decrease of cell-bound label, one or more cells expressing at least one cell surface HE having a target sequence cleaving specificity. In certain library screening implementations, the method of claim 45, wherein the one or more cells comprises a library of cells, the library comprising a plurality of cells, wherein each cell comprises at least one recombinant homing endonuclease (HE) expression system suitable to provide for cell-surface presentation or display of at least one HE, or fusion, mutein or variants thereof on the cell, and wherein a plurality of different homing endonuclease (HE), or fusions, muteins or variants thereof are represented.

Selection and screening of homing endonuclease variants based on the cleavage capacity is performed, at least in part, under conditions compatible with the cleavage activity. The homing endonuclease variants used in the selection and/or screening based on cleavage capacity may be either the initial library of homing endonuclease variants or the homing endonuclease variants selected and/or screened for the binding activity.

If necessary, the selected and/or screened homing endonuclease variants are subcloned in an appropriate expression vector for the in vitro and in vivo cleavage assay. Such subcloning step can be performed in batch or individually. More particularly, if the initial homing endonuclease is a dimer, the subcloning step allows the introduction of the selected library(ies) in a single chain homing endonuclease structure. If two libraries have been selected and/or screened for two half recognition and cleavage sites, the subcloning step allows to bring together the two selected libraries in a single chain homing endonuclease structure.

HE Delivery:

The HEs or LHEs can be used either as a polypeptide or as a polynucleotide construct encoding said polypeptide under the control of appropriate transcription regulatory elements including a promoter, for example a tissue specific and/or inducible promoter. Examples of inducible promoters are: eukaryotic metallothionine promoter which is induced by increased levels of heavy metals, prokaryotic lacZ promoter which is induced in response to isopropyl-.beta.-D-thiogalactopyranoside (IPTG) and eukaryotic heat shock promoter which is induced by increased temperature. Examples of tissue specific promoters are skeletal muscle creatine kinase, prostate-specific antigen (PSA), .alpha.-antitrypsin protease, human surfactant (SP) A and B proteins, .beta.-casein and acidic whey protein genes. It is introduced into somatic cells of an individual, by any convenient mean well-known to those in the art, alone or in association with either at least an appropriate vehicle or carrier and/or with the targeting DNA.

In certain embodiments, the HE (polypeptide) is associated with: liposomes, polyethyleneimine (PEI); in such a case said association is administered and therefore introduced into somatic cells target; membrane translocating peptides (Bonetta, 2002, The Scientist, 16, 38; Ford et al, Gene Ther, 2001, 8, 14; Wadia & Dowdy, 2002, Curr Opin Biotechnol, 13, 52-56); in such a case, there is a fusion with said peptides.

HEs can also be introduced into somatic tissue(s) from an individual according to methods generally known in the art which are appropriate for the particular homing endonuclease and cell type.

In additional embodiments, the HE (polynucleotide encoding said homing endonuclease) and/or the targeting DNA is inserted in a vector. Vectors comprising targeting DNA and/or nucleic acid encoding a homing nuclease can be introduced into a cell by a variety of methods (e.g., injection, direct uptake, projectile bombardment, liposomes). HEs can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). Optionally, it may be preferable to incorporate a nuclear localization signal into the recombinant protein to be sure that it is expressed within the nucleus. Preferably, the sequence encoding the homing endonuclease and the targeting DNA are inserted in the same vector.

Suitable vectors include, but are not limited to, viral particles, a plasmid, a RNA vector or a linear or circular DNA or RNA molecule which may consists of a chromosomal, non chromosomal, semisynthetic or synthetic DNA. Preferred vectors are those capable of autonomous replication (episomal vector) and/or expression of nucleic acids to which they are linked (expression vectors). Large numbers of suitable vectors are known to those of skill in the art and commercially available. Viral particles can be derived from a variety of natural viruses, including retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of viral particles are described, for example, in McVey et al., U.S. Pat. No. 5,801,030, the teachings of which are incorporated herein by reference.

Vectors can also comprise selectable markers (for example, neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracycline, rifampicin or ampicillin resistance in *E. coli*; etc.).

Once in a cell, the homing endonuclease, and if present, the vector comprising targeting DNA and/or nucleic acid encoding a homing endonuclease are imported or translocated by the cell from the cytoplasm to the site of action in the nucleus or other DNA containing organelle, such as mitochondria. Preferably, this would be accomplished by appending a nuclear or mitochondrial localization sequence, respectively, to the LHE, of which many types are know to those of ordinary skill in the art.

It will be appreciated by those skilled in the art having the benefit of this disclosure that particular aspects of this invention provide a method and system of providing cell surface expression of homing endonucleases (HEs) or LAGLIDAG homing endonuclease (LHEs) to provide for novel compositions and methods comprising same. It should be understood that the drawings, detailed description and Examples herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the claimed subject matter. Thus, it is intended that the claims be interpreted to embrace all such further modifications, changes, rearrangements, substitutions, alternatives, design choices, and embodiments.

Example 1

The Following Methods were Used in the Working Examples Herein

Methods:

Plasmid Construction and Generation of Stable LHE Expressing DT40 Clones.

Vectors containing cDNA for both LHEs (I-AniI and H-DreI) were PCR amplified using following primers: I-AniI For SfiI (SEQ ID NO:1) and I-AniI Rev SalI (SEQ ID NO:2); H-DreI For SfiI (SEQ ID NO:3) and H-DreI Rev SalI (SEQ ID NO:4) and cloned into the pLHCX-phOx expression vector (Chou, et al., *Biotechnol Bioeng*, 65:160-169, 1999; Liao, et al., *Biotechnol Bioeng*, 73:313-323, 2001) by SfiI and SalI digestion to replace phOx coding sequence. To place the NeoR gene in frame in the I-AniI construct, the NeoR cDNA including the HSV polyA sequence was amplified using CD80-NeoR For (SEQ ID NO:5) and NeoR Rev ClaI (SEQ ID NO:6), while the existing I-AniI-CD80 expression construct (including the 5' signal peptide and HA epitope) was amplified by primers SP For Hind3 (SEQ ID NO:7) and CD80-NeoR Rev (SEQ ID NO:8). The entire fusion molecule was generated by fusion PCR as described previously (Mohler & Blau, *Somat Cell Mol Genet*, 20:153-162, 1994), and subcloned back into the pLHCX plasmid by HindIII and ClaI digestion. Mutation of residues K21, T27 for I-AniI$^m$ generation was achieved by site-directed mutagenesis (Stratagene QuikChange II, #200523-5) using I-AniI K21 T27 SDM For (SEQ ID NO:9) and I-AniI K21 T27 SDM Rev (SEQ ID NO:10), and the L223 mutation arose by PCR error. For transfection of DT40 cells, 30 µg of linearized plasmid DNA was electroporated into $10^7$ DT40 cells (IgM-negative where indicated) using a Gene Pulser XCell (BioRad) in a final volume of 400 ul of serum-free RPMI media employing the exponential protocol: 550 V, 25 µF, ∞ resistance with a 4 mm cuvette gap. After 24 h of culture in drug-free media, cells were plated by limiting dilution in media containing 2 mg/ml G418 (Invitrogen, #11811-098) for 10-14 days. Wells containing single G418-resistant clones were expanded and screened by flow cytometry for HA surface expression.

Exemplary primers:
I-AniI For SfiI:
(SEQ ID NO: 1)
GGCCCAGCCGGCCATGGGCAGCAGCCATCATCATC;

I-AniI Rev SalI:
(SEQ ID NO: 2)
GTCGACATAATTTGAAGGTATTTTTATTTTTCTG;

H-DreI For SfiI:
(SEQ ID NO: 3)
GGCCCAGCCGGCCATGCATAATAATGAGAATGTT;

H-DreI Rev SalI:
(SEQ ID NO: 4)
GTCGACCGGGGACGATTTCTTTTTTTCACT;

CD80-NeoR For:
(SEQ ID NO: 5)
CAGACCGTCTTCCTTGGATCGGCCATTGAACAAG;

NeoR Rev ClaI:
(SEQ ID NO: 6)
ATCGATGAACAAACGACCCAACACCCGTGCG;

SP For Hind3:
(SEQ ID NO: 7)
AAGCTTATGGAGACAGACACACTCCTGCTATGGG;

CD80-NeoR Rev:
(SEQ ID NO: 8)
CTTGTTCAATGGCCGATCCAAGGAAGACGGTCTG;

I-AniI K21 T27 SDM For:
(SEQ ID NO: 9)
CAGCATCACCAACAAGGGTAAGTACCTACAGTATGAGCTGGGTATCGAG;

and

I-AniI K21 T27 SDM Rev:
(SEQ ID NO: 10)
CTCGATACCCAGCTCATACTGTAGGTACTTACCCTTGTTGGTGATGCTG.

Western Blotting and Glycosylation Analysis by PNGase F Treatment.

Briefly, $7.5 \times 10^6$ cells of the indicated cell lines were washed once in ice-cold PBS containing 0.1% BSA and lysed for 30 min at 4° C. in lysis buffer (25 mM Tris·Cl pH 7.4, 140 mM NaCl, 2 mM EDTA, 1% NP-40, 0.05% sodium deoxycholate, 0.005% SDS, and protease inhibitors). The crude cell lysates were clarified by centrifugation and 50 µg of total protein from post-nuclear cell lysates were used for incubation with PNGase F (New England Biolabs, #P0704S) for 2 hours according to manufacturer's guidelines. Samples were analyzed by western blotting using anti-HA (Cell Signaling Technology, #2367) and anti-β- actin Ab (Sigma-Aldrich, #A1978) followed by HRP-conjugated anti-mouse-IgG (Amersham Biosciences, #NA931V).

Flow Cytometry.

Figure 2:
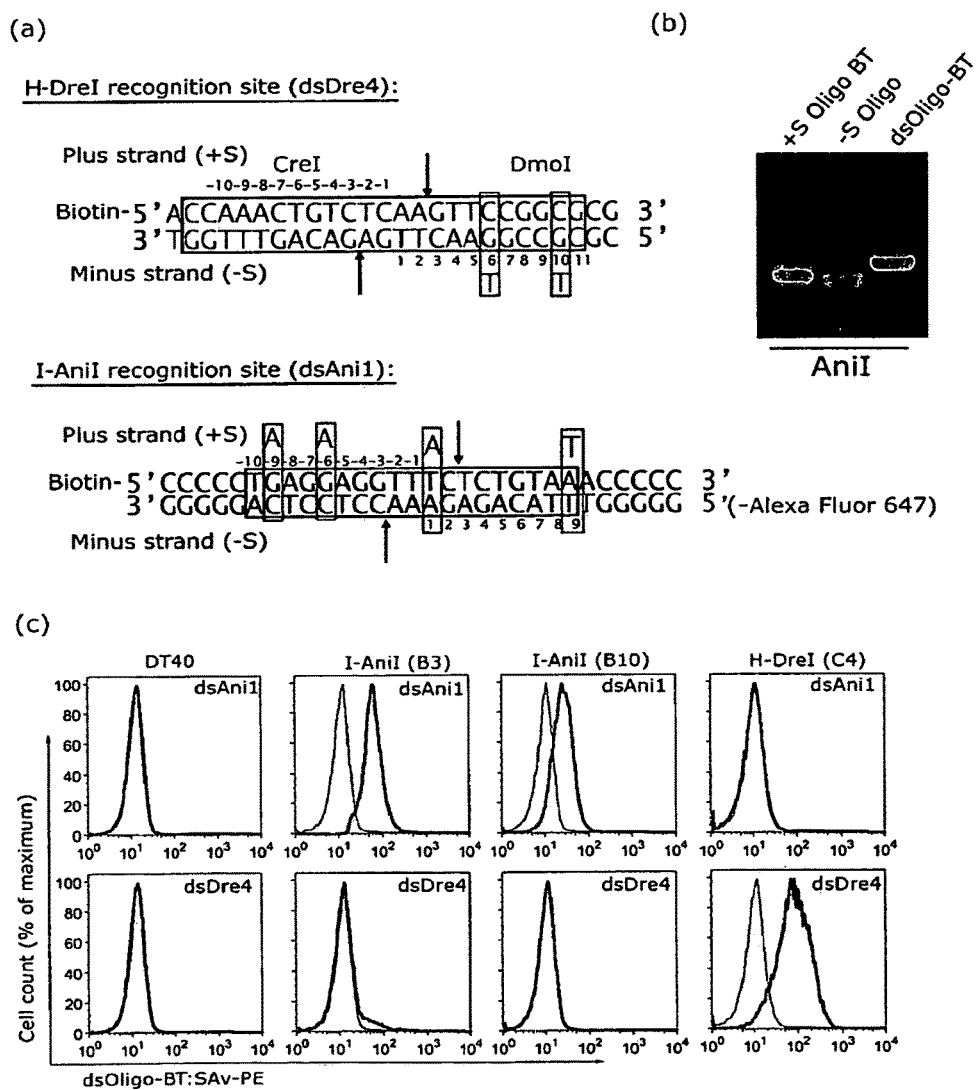
FIGS. 2a-2c show, according to particular exemplary aspects, data confirming that fluorescently conjugated dsOligos (Biotin-5' ACCAAACTGTCTCAAGTTCCGGCGCG 3', SEQ ID NO:23 ("dsDre4"); and Biotin-5' CCCCCT-GAGGAGGTTTCTCTGTAAACCCCC 3' SEQ ID NO:24 ("dsAni1")) bind cell surface LHEs in a manner which is sequence specific and easily resolved by flow cytometry.

Standard antibody staining was done in PBS containing 0.2% BSA using the following antibodies: mouse monoclonal anti-HA (Cell Signaling Technology, #2367) followed by PE-conjugated goat anti-mouse IgG1 (Southern Biotech, #1070-09S); FITC-conjugated anti-chicken IgM (Bethyl Laboratories Inc., #A30-102F). Preparation of dsOligos and subsequent staining was performed as follows: complementary 5'-biotinylated and non-biotinylated DNA oligonucleotides (FIG. 2) were annealed by incubation at 94° C. for 5 minutes and allowed to cool slowly to room temperature, sterilized by ethanol precipitation and resuspended to a stock concentration of 1.6 µM. Cells were first incubated at 4° C. for 30 minutes in a standard dsOligo blocking and staining buffer containing 135 mM NaCl, 5 mM KCl, 10 mM CaCl$_2$, 5.6 mM Glucose, 10 mM HEPES, 0.2% BSA and 1 µg/ml sonicated salmon sperm DNA, pH 7.4. Concurrent with this incubation, annealed dsOligos were complexed with SAv-PE (BD Biosciences, #554061, Mw 300,000) at 1:1 molar ratio in the same buffer. The dsOligo-BT:SAv-PE complexes were used to stain the cells at a final concentration of 10-50 nM for 30-40 minutes at 4° C. Cells were washed twice with ice-cold buffer prior to analysis. Antibody and dsOligo stained cells were analyzed by flow cytometry using the Beckton Dickenson FACSCalibur or LSRII instruments (BD Biosciences). 10,000 to 100,000 live cells were acquired per sample and the resulting raw data were processed using FlowJo software (FlowJo, LLC).

Fluorescence-Activated Cell Sorting (FACS).

Briefly, LHE-expressing clones were mixed at the indicated ratios immediately prior to staining. The cells were stained using the above protocol with the indicated dsOligo complexes (SAv-Q655 from Invitrogen, #Q10121 MP). The PE- or Q655-positive populations of live-gated doublet-excluded cells were sorted using the BD Aria cell sorter. Sorted populations were cultured for 5-7 days and labeled with either dsOligos or anti-IgM for flow cytometry analysis. In particular aspects, the above process was iterated for subsequent rounds of enrichment.

Magnetic Cell Sorting (MACS).

Briefly, cells were mixed at the indicated ratios (approximately 5–10×10$^7$ cells per sample) and labeled for 30 minutes at 4° C. with 100 nM dsAni1 in the same buffer used for flow cytometry. After washing, the mixed population was incubated with 20-50 µl SAv-coated magnetic beads (Miltenyi Biotec, #130-048-101) in a final volume of 0.5-1.0 ml for 20 minutes at 4° C. The samples were washed twice and resuspended at a concentration of 2×10$^7$ cells/ml prior to loading onto the AutoMACS cell separator. The "posselds" double column separation program was run and the positive fraction was washed and placed immediately in culture. Cells were analyzed by staining separately with anti-IgM and dsAni1 as described above.

Flow Cytometry Assay for dsOligo Cleavage.

Complementary 5'-Biotin and 5'-Alexa Fluor647 conjugated (Invitrogen) DNA oligonucleotides were annealed as described above. The buffer used for all steps of the cleavage assay contained 10 mM NaCl, 90 mM KCl, 10 mM HEPES, 5.6 mM Glucose, 0.2% BSA, 1 µg/ml salmon sperm DNA and pH 8.5. Approximately 1×10$^6$ cells were first incubated at 4° C. with biotinylated mouse anti-HA Ab (Abcam, #AB27987-100) at a dilution 1:300 for 3040 minutes. After washing, the cells were stained with 30-50 nM 647-dsOligo-BT:SAv-PE for 30 minutes on ice. For cleavage, 10 mM MgCl$_2$ was added to the buffer and the reaction was carried out at 42° C. for the designated time points. The cells were washed in Mg$^{2+}$-free buffer and analyzed by flow cytometry.

In-Vitro LHE Cleavage Assay and Fluorescence Gel Imaging.

Reaction conditions were identical to those described in the flow cytometry cleavage assay except that 30 nM recombinant I-AniI was used in place of cells for the in vitro assays. For the in vitro assay with bead-complexed oligos, 647-dsOligo-BT:SAv-bead complexes were formed by incubating 50 nM dsOligo with 20 ul SAv-conjugated Dynabeads for 30 minutes at room temperature. The unbound 647-dsOligo-BT was removed by extensive washing in cleavage assay buffer, followed by incubation with 30 nM recombinant I-AniI for 1 hour at 42° C. Oligonucleotide fragments were purified by phenol extraction followed by ethanol precipitation. The purified samples were resuspended in Ficoll-based loading buffer and resolved by PAGE. The gels were scanned using the Typhoon 9410 system (GE Healthcare) with excitation by the 633 nm laser. Images were acquired with detector PMT voltages at both optimal (between 450 and 600 volts) and maximal (between 700 and 850 volts) settings to observe all fluorescent species. Images were processed with Adobe Photoshop using linear adjustments and all detectable bands in each lane are visible.

Example 2

Novel Expression of Homing Endonucleases on the Plasma Membrane Surface was Achieved Example Overview.

LHEs are normally expressed in the cytosol and targeted to DNA-containing organelles posttranslationally. According to particular aspects of the present invention, cell surface display is achieved by cotranslational targeting to the secretory pathway and fusion to an appropriate transmembrane domain. Strategies of this sort have been previously used to support surface display of antibody fragments (e.g., Chou, et al., *Biotechnol Bioeng*, 65:160-169, 1999; and Liao, et al., *Biotechnol Bioeng*, 73:313-323, 2001), but prior to the present inventive aspects, DNA target site binding and cleavage activities of homing endonucleases (HE) were only known to occur in the context of free-standing enzymes in solution and/or intracellularly.

Methods.

For this Example, LAGILDADG homing endonuclease (LHE) genes were inserted between the coding sequences of the N-terminal murine immunoglobulin signal peptide (SP) and the transmembrane region of the murine CD80 molecule (FIG. 1a). In FIG. 1(a), LHE cDNAs were placed in-frame between a murine immunoglobulin-derived N-terminal signal peptide (SP) and the transmembrane spanning region of the murine CD80 molecule at the C-terminus. G418 resistance was conferred by a NeoR gene driven by an independent promoter.

Two different LHE coding sequences were integrated into the CMV promoter-driven surface expression constructs: I-AniI, an endonuclease encoded in the mitochondrial genome of *Aspergillus nidulans* (Bolduc, et al., *Genes Dev*, 17:2875-2888, 2003); and H-DreI (Hybrid-Dmo/CreI, formerly called 'E-DreI'), an engineered endonuclease containing an N-terminal domain derived from I-DmoI LHE (*Desulfurococcus mobilis*) and a C-terminal domain derived from I-CreI (*Chlamydomonas reinhardtii*) (Chevalier, et al., *Mol Cell*, 10:895-905, 2002). These constructs included a hemagglutinin (HA) epitope tag downstream of the SP to facilitate biochemical and flow cytometric detection.

Results.

Figure 1B:
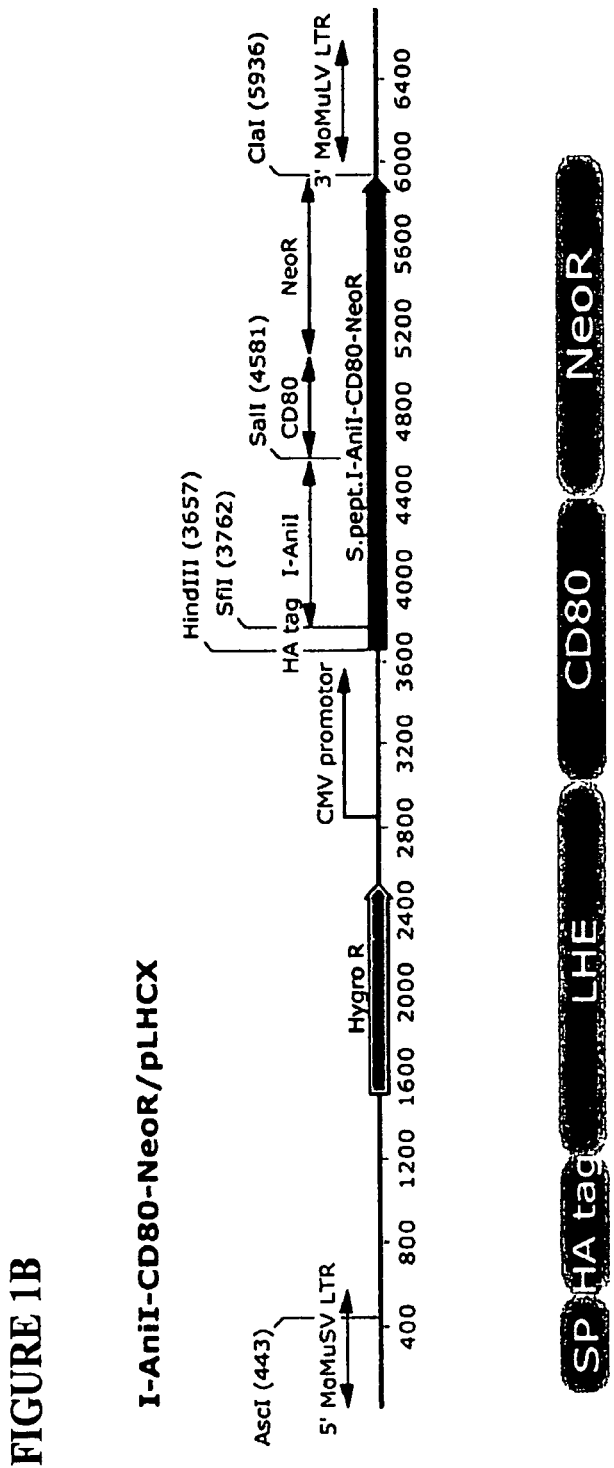
Figure 1C:
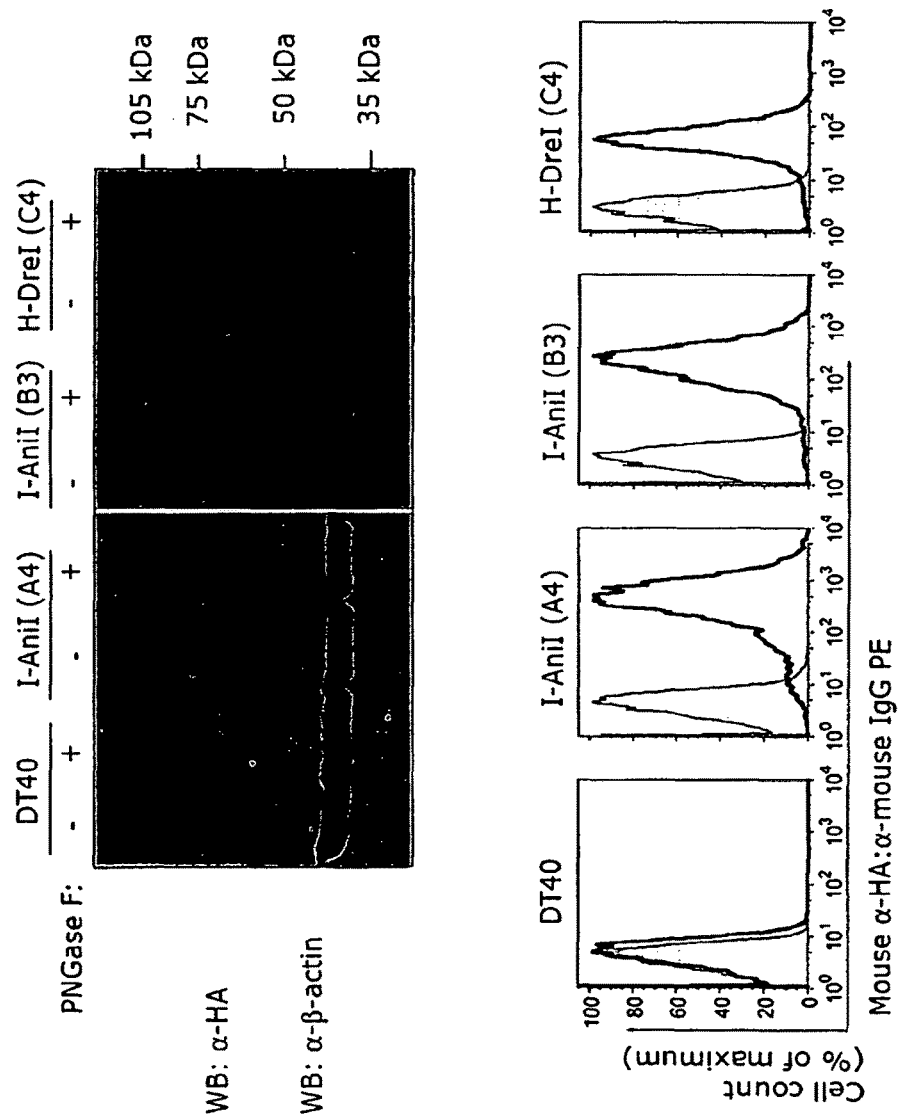

Transfection of the linearized constructs into DT40 cells resulted in the isolation of clonal lines with high levels of I-AniI and H-DreI surface expression (FIG. 1c). FIG. 1(c) shows Western blot and flow cytometry analysis from clones expressing I-AniI (A4 and B3) and H-DreI (C4).

Figure 1D:
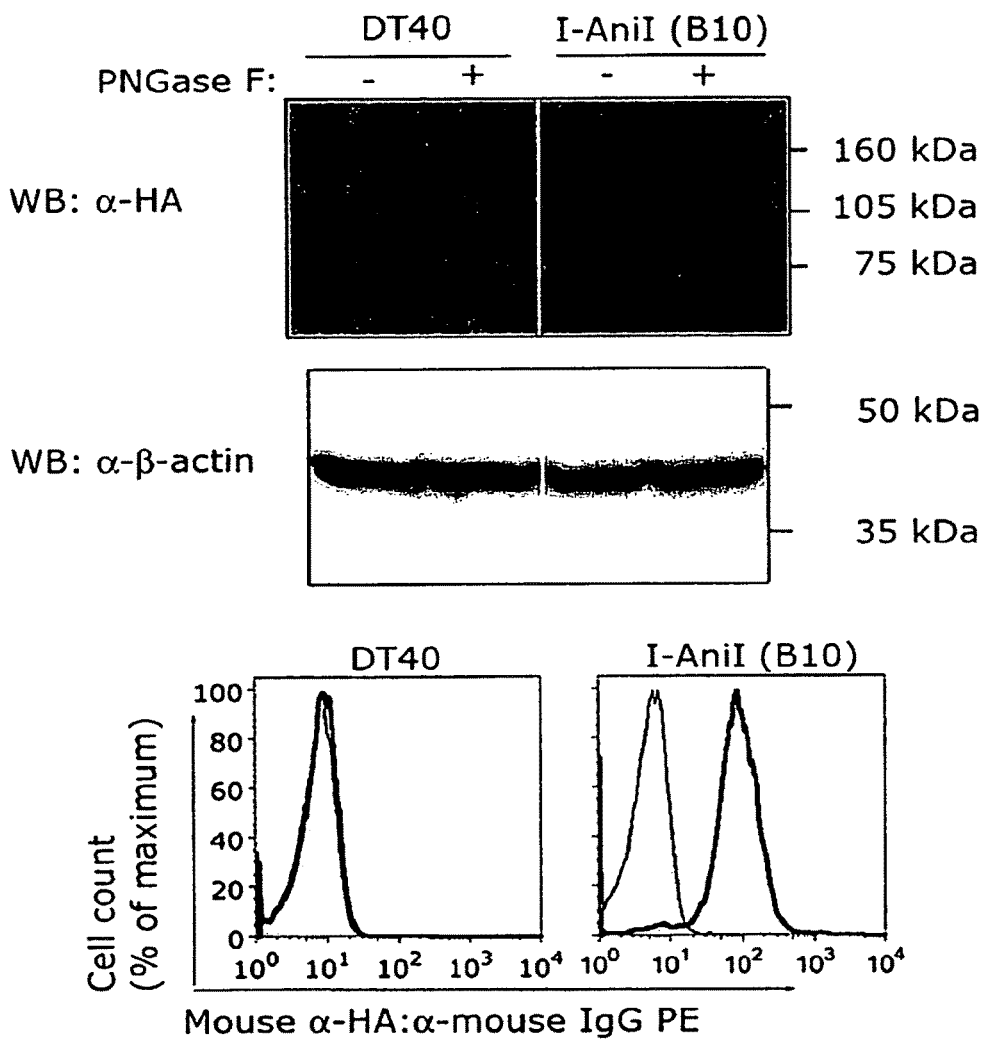

Intracellularly expressed LHEs are not exposed to glycosyltransferase enzymes, however this is an important consideration when their expression is directed to the cell surface. Primary sequence analysis revealed that LHE fusion proteins do contain potential N-glycosylation motifs (N-X-S/T where X≠P or D). Therefore, to evaluate their N-glycosylation status, lysates of LHE-expressing cells were incubated with the enzyme peptide-N-glycosidase F (PNGaseF). The N-glycosylation status was estimated by observing changes in band mobility during electrophoresis, which demonstrated that PNGaseF-treated LHE fusion proteins migrated faster and with less variability compared with the untreated controls (FIGS. 1c and 1d). FIG. 1(d) shows such data from clone B10 expressing I-AniI as a fusion with C-terminal NeoR. The status of treatment with PNGase F is indicated above the lanes. The corresponding clones were analyzed by flow cytometry for surface HA detection.

These results indicate that the membrane-anchored molecules were indeed N-glycosylated, consistent with their surface expression through the secretory pathway.

Particular aspects of the present invention comprise application of cell surface expressed HE's and LHE's in identification of desired HE and LHE variants from large libraries generated by random or targeted mutagenesis. For such aspects, it is preferable to have a tight linkage between surface HE or LHE expression and a selection marker as a means to enrich for variants that are efficiently expressed. In particular embodiments, a strategy involving fusion of a neomycin resistance (NeoR) gene in frame with the C-terminus of the CD80 transmembrane domain is and was used (FIG. 1b) (Mohler & Blau, *Somat Cell Mol Genet*, 20:153-162, 1994) such that the NeoR activity is positioned on the cytosolic face of vesicles and the plasma membrane after expression. FIG. 1(b) illustrates how the SP-HA-LHE-CD80 cassette was placed in-frame with the NeoR gene to allow coupled expression from a single promoter. Both constructs include an HA epitope tag at the N-terminus of the LHE, and transcription is driven by the CMV promoter. According to particular aspects, transfection of LHE-CD80-NeoR constructs and application of neomycin selection allowed the isolation of multiple DT40 clones with stable surface expression of HA immunoreactivity from a single promoter (FIG. 1d, showing data from clone B10 expressing I-AniI as a fusion with C-terminal NeoR).

Example 3

Surface Expressed LHEs were Efficiently Labeled with Fluorescently Conjugated dsOligos and Detected by Flow Cytometry In this Example, the ability of the inventive cell surface displayed LHEs to bind annealed oligonucleotides representing the respective natural target specificities was confirmed using flow cytometry.

Methods.

HEs are enzymatically active in the presence of $Mg^{2+}$ ions, which are present in the active site (Chevalier, et al., *Nat Struct Biol*, 8:312-316, 2001). When $Mg^{2+}$ ions are replaced with $Ca^{2+}$ ions, LHEs retain their DNA binding properties, while the cleavage of target DNA sequence is abolished (Chevalier, et al., *Nat Struct Biol*, 8:312-316, 2001; Chevalier, et al., *Biochemistry*, 43:14015-14026, 2004). While this metal ion specificity was known in the art for free-standing or intracellular enzymes, applicants conceived that this may also be true for cell surface displayed HEs and LHEs. Accordingly, a buffer containing 10 mM $Ca^{2+}$ was used for cell-surface staining of LHE-expressing clones using fluorescently labeled dsOligos. To minimize the effects of variations in dissociation kinetics of different LHEs, a single-step staining protocol with pre-formed complexes of biotinylated dsOligos (dsOligo-BT, FIG. 2b) with phycoerythrin-conjugated streptavidin (SAv-PE) was used. Since streptavidin contains four high affinity biotin-binding subunits, complexes (dsOligo-BT:SAv-PE) were created at a 1:1 molar ratio to maximize the fluorescent signal per target sequence. FIG. 2(b) shows data verifying efficient annealing of the complementary oligonucleotides run on a 3% agarose gel, with individual oligos (+S and −S) run as controls.

Results.

Staining I-AniI and H-DreI expressing clones with dsOligos of their respective natural target sequences generated clearly labeled populations despite their apparent N-glycosylation (FIG. 2c). FIG. 2(c) shows data from flow cytometry analysis of clones stained with fluorescent dsOligos. Staining of I-AniI and H-DreI expressing clones in the presence of 10 mM $Ca^{2+}$ are shown, with shaded and open histograms representing SAv-PE-only controls and dsOligo-BT:SAv-PE stained cells respectively. The dsOligos used for each stain are indicated in the upper right corner of the histograms.

This analysis indicates that surface expressed LHEs were efficiently labeled with fluorescently conjugated dsOligos and detected by flow cytometry, and further indicates that glycosylation does not confound surface analysis of these particular LHEs.

To assess the possibility that the inventive expression and detection system leads to is degenerate DNA substrate recognition, I-AniI and H-DreI expressing clones were stained with dsOligos containing modifications to their respective target sequences. As expected, no detectable staining was observed when dsAni1 or dsDre4 were used to stain non-corresponding LHE-expressing clones (FIG. 2c).

To achieve a precise characterization of staining specificity, dsOligos were designed bearing single base-pair differences from the known target sequence (dsAni1$^{-9A}$(SEQ ID NO:11), dsAni1$^{-6A}$ (SEQ ID NO:12), dsDre4$^{6T}$ (SEQ ID NO:Y13), dsDre4$^{10T}$ (SEQ ID NO:14), FIG. 2a). FIG. 2(a) illustrates that H-DreI is an engineered enzyme composed of domains derived from the I-CreI and I-DmoI LHEs, having a 23-bp recognition site (dsDre4, boxed) that is a complex of the natural target sequences bound by I-CreI (green) and I-DmoI (purple). The 19-bp I-AniI recognition site (SEQ ID NO:19) (dsAni1, boxed) was placed between stretches of five GC base-pairs designed to enhance the formation and stability of the double-stranded complex. Single base-pair changes (dsDre4$^{6T}$(SEQ ID NO:13, dsDre4$^{10T}$ (SEQ ID NO:14), dsAni1$^{-6A}$ (SEQ ID NO:12), and dsAni1$^{-9A}$ (SEQ ID NO:11)) are indicated by red boxes and the cleavage sites by red arrows. The alternative I-AniI target sequence (dsAni2) (SEQ ID NO:15), containing two base-pair changes are shown in blue boxes. Conjugations with biotin at the 5' termini are depicted, and Alexa Fluor 647 conjugated oligonucleotides for dsAni1 and dsAni1$^{-9A}$ were used in the flow cytometry cleavage assay.

Figure 3A:
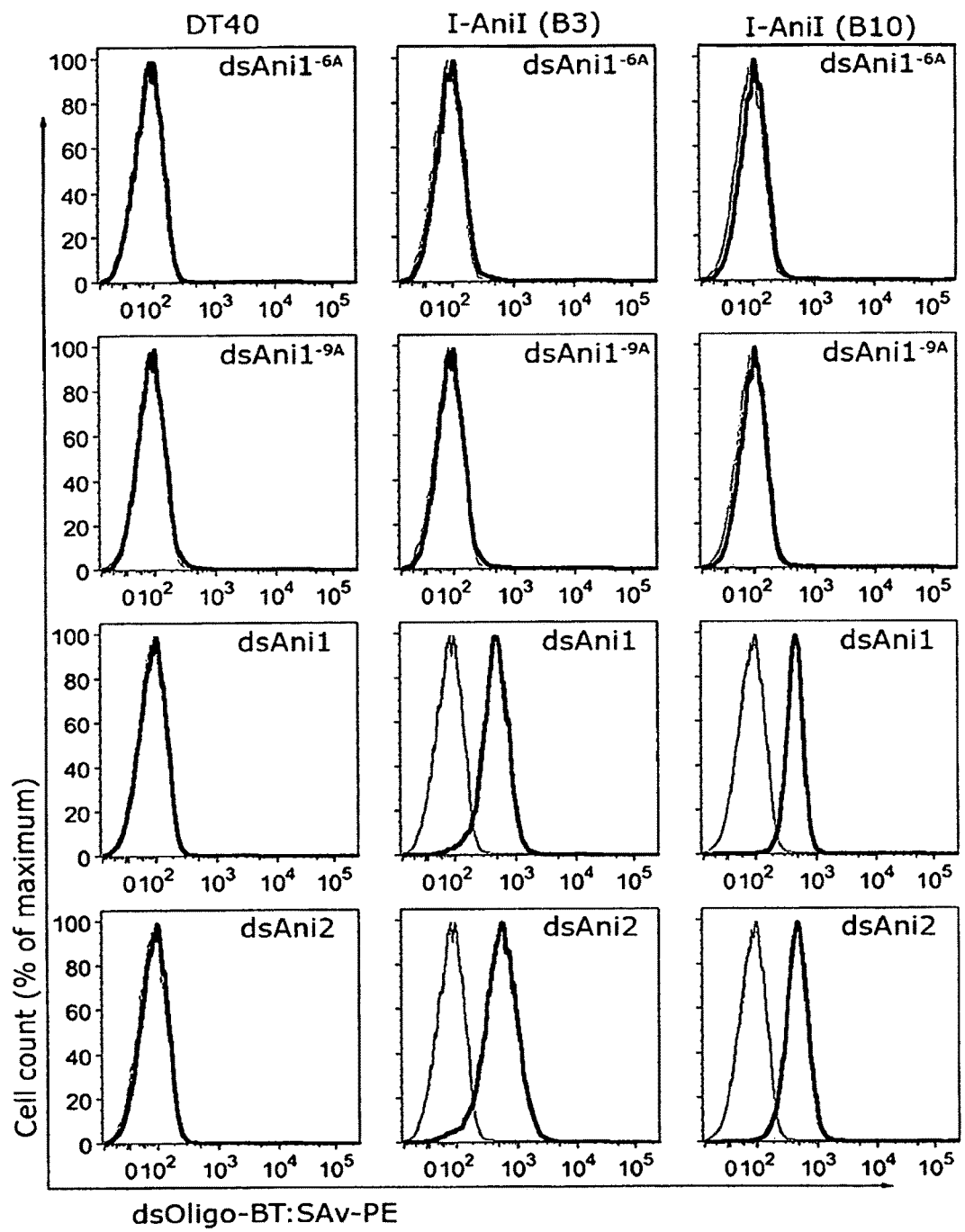
FIGS. 3a and 3b show, according to particular exemplary aspects, that LHEs expressed on the cell surface reliably discriminate dsOligos containing single-base pair differences from their natural target sequences.
Figure 3B:
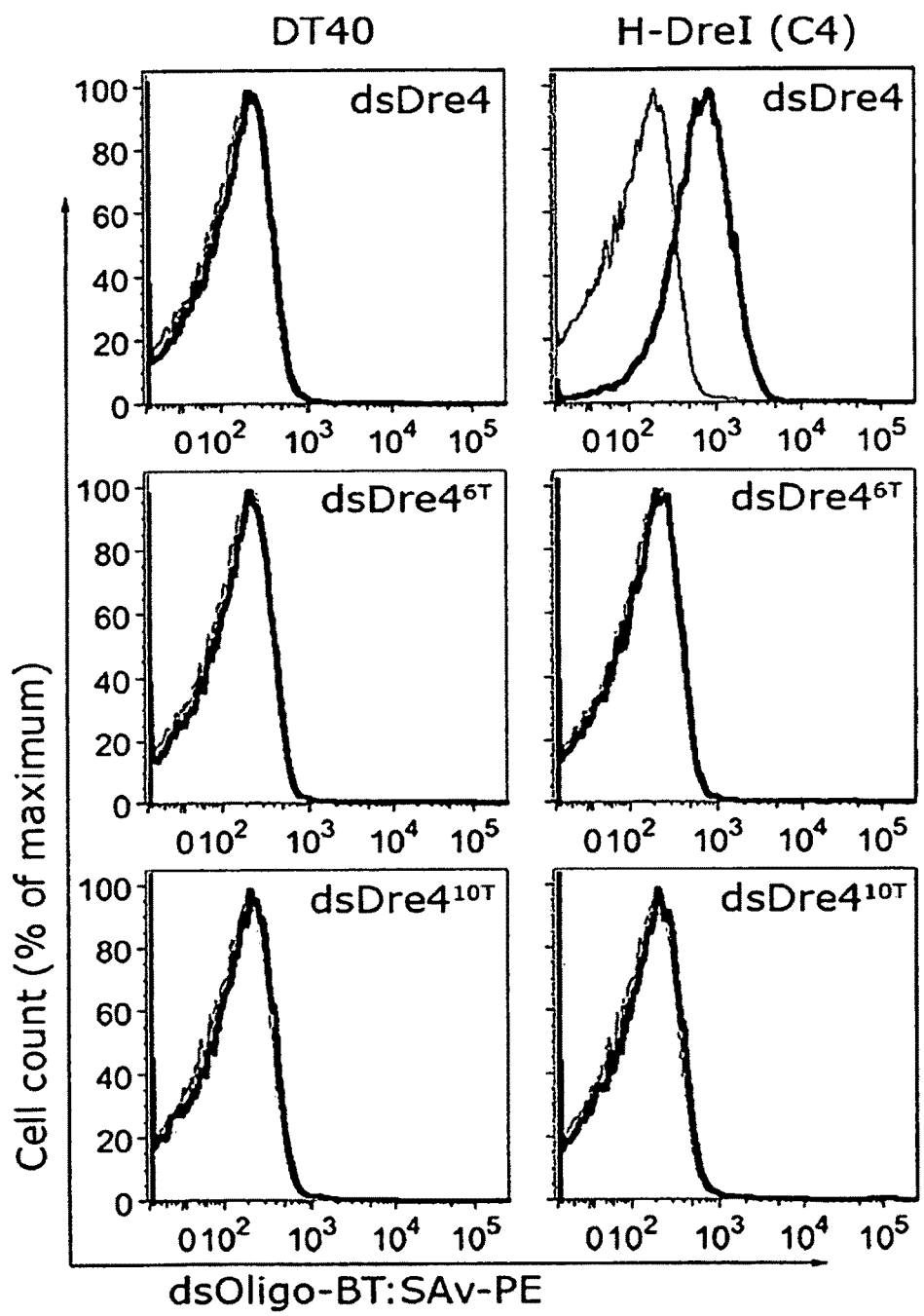

These substitutions were chosen to interrupt direct contacts within the I-AniI and H-DreI DNA-protein interfaces (Chevalier, et al., *Mol Cell,* 10:895-905, 2002; Bolduc, et al., *Genes Dev,* 17:2875-2888, 2003). Remarkably, these single base-pair changes resulted in little or no detectable staining above non-specific background levels (FIG. 3), consistent with the predicted destabilization of the binding interactions with their respective LHEs. FIGS. 3a and 3b show, according to particular exemplary aspects, that LHEs expressed on the cell surface reliably discriminate dsOligos containing single-base pair differences from their natural target sequences. FIG. 3(*a*) and FIG. 3(*b*) show data corresponding to I-AniI and H-DreI expressing clones, respectively, that were stained with dsOligo-BT:SAv-PE complexes containing the natural target sequences (dsAni1 and dsDre4) or containing single base-pair changes (dsAni1$^{-6A}$ and dsAni1$^-$$_{9A}$; dsDre4$^{6T}$ and dsDre4$^{10T}$). Known target sequence degeneracy for I-AniI was thereby also shown herein to be recapitulated by dsOligo staining and analysis by flow cytometry. The cells expressing I-AniI were efficiently stained with dsAni2 corresponding to an alternative I-AniI target sequence known to be cleaved with an efficiency that is similar to the natural target sequence.

Figure 4A:
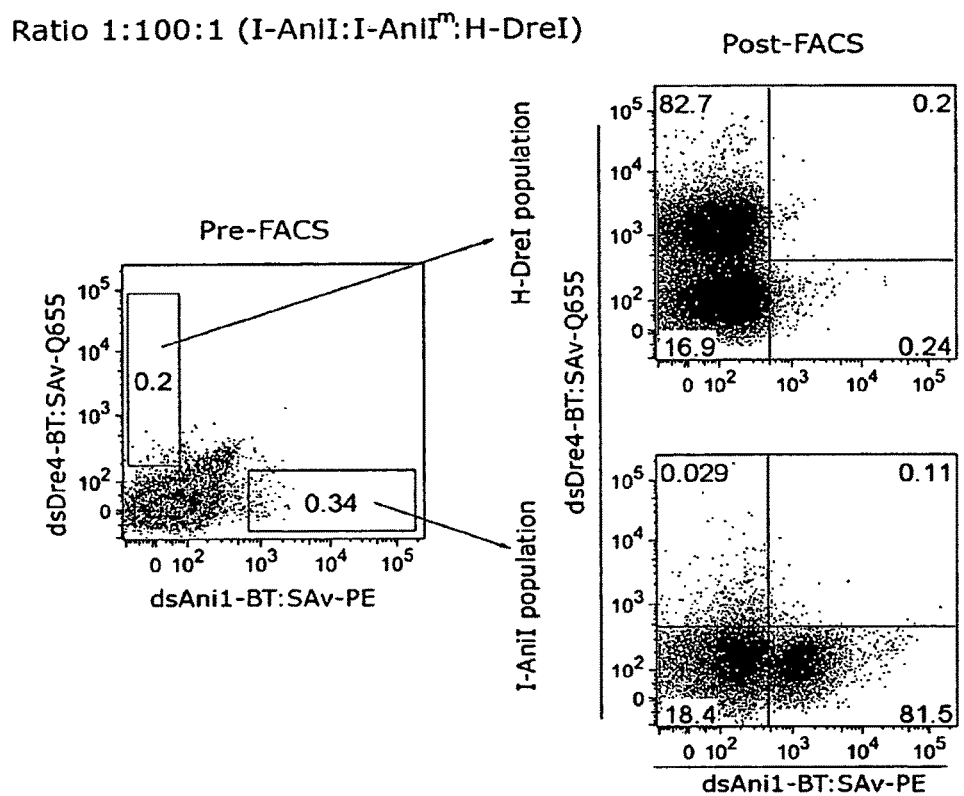
FIGS. 4a and 4b show, according to particular exemplary aspects, that fluorescent and/or magnetic strategies facilitate target sequence-specific sorting of cells expressing surface LHEs.
Figure 4B:
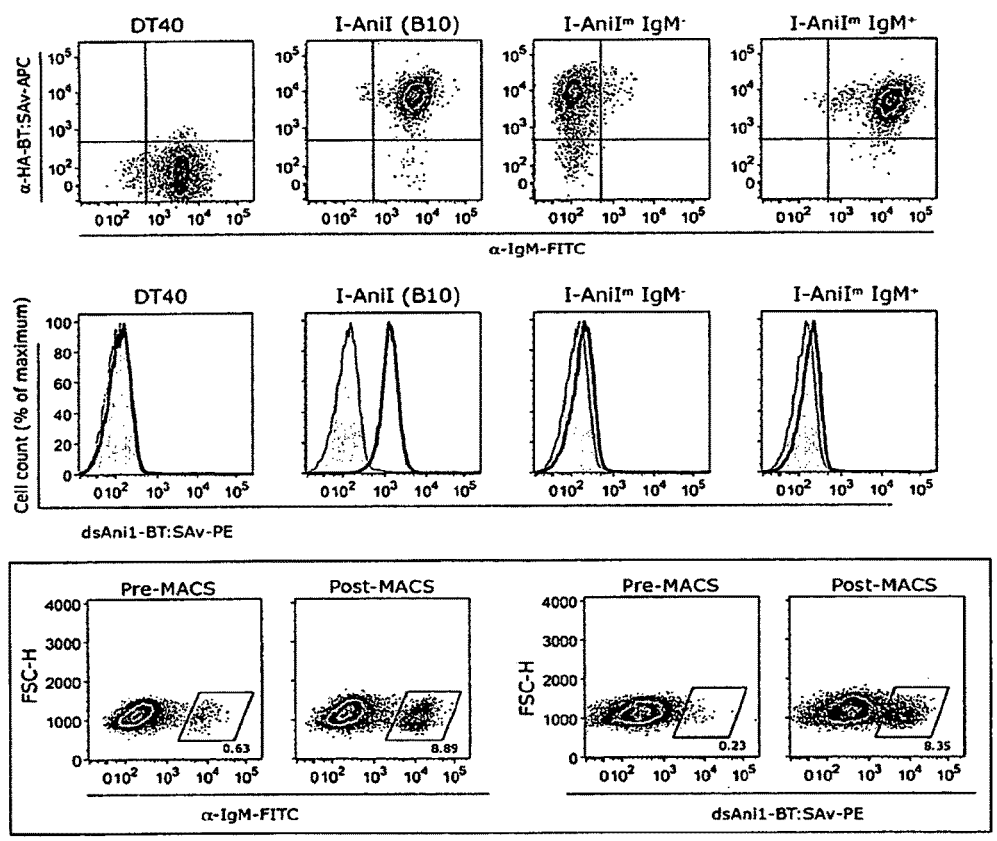

Conversely, we have generated NeoR-linked clones with mutant I-AniI enzymes (generally denoted as I-AniI$^m$) expressed stably on the cell surface (FIG. 4b). FIGS. 4a and 4b show, according to particular exemplary aspects, that fluorescent and/or magnetic strategies facilitate target sequence-specific sorting of cells expressing surface LHEs. FIG. 4a shows data from three populations of cells expressing different LHEs (I-AniI, I-AniI$^m$ and H-DreI) that were mixed at a 1:100:1 ratio and double stained with dsAni1-BT:SAv-PE and dsDre4-BT:SAv-Q655, followed by FACS. The resulting sorted populations were cultured for 5-7 days prior to analysis and subsequent rounds of sorting. In post-sort analyses, cells stained with dsAni1 and dsDre4 are shown in red and blue, respectively. FIG. 4(*b*) shows data from enrichment of low frequency dsOligo binding cells by MACS. IgM-negative DT40 cells expressing I-AniI$^m$ (top row, third panel) were used as a background population into which IgM-positive B10 cells were added at a frequency of 0.1%. IgM-positive I-AniI$^m$ cells were included at 0.5% to control for potential background dsOligo binding caused by surface immunoglobulin expression, leading to a total of 0.6% IgM-positive cells in the input population, the majority of which do not stain with dsAni1. This mixed population was stained and sorted using AutoMACS (see Methods under "Example 1" herein for details). The positive fraction was grown out and analyzed for IgM expression. Staining with dsAni1 confirmed that the enriched IgM-positive population primarily expressed wild-type I-AniI.

Two I-AniI$^m$ clones were used in the experiments of this Example, and were predicted to have either core structural changes or designed to have lost specific contacts at the DNA-binding interface. Though the structural consequences of these mutations were not validated, the failure of the mutant enzymes to bind dsAni1 indicates that structural alterations which do not inhibit LHE expression have DNA binding consequences that are resolvable by the inventive approach. The analysis was further extended to a unique target sequence variation against which wild-type I-AniI is known to maintain its cleavage activity (dsAni2, unpublished data, FIG. 2*a*). This second I-AniI target sequence readily stained clones expressing I-AniI, further supporting the correlation of dsOligo-based interrogation of LHEs on the cell surface with biochemical cleavage data (FIG. 3*a*, bottom panels).

These data therefore indicate, according to particular inventive aspects, that surface expressed LHEs reliably discriminate closely related dsOligo sequences in a manner which both parallels their reported target sequence cleavage specificities and is sensitive to mutations in the DNA binding and core regions of the enzyme.

Example 4

Cells Labeled with dsOligos were Subjected to Multi-Parameter Fluorescence Activated Cell Sorting (FACS) for Effective Enrichment In the Example, the inventive labeling method was assessed for utility and suitability for sequence dependent physical separation of LHE expressing cells by flow cytometry.

Methods.

Three DT40 clones expressing different LHEs were used: clone B3 expressing I-AniI; clone C4 expressing H-DreI; and an I-AniI$^m$ clone carrying a mutation proximal to the LAGLIDADG dimerization alpha-helix was utilized as the background population. The cells were mixed at a ratio of 1:100:1 for B3:I-AniI$^m$:C4 clones respectively, and the mixed population was then stained with dsAni1-BT:SAv-PE and a quantum dot-conjugated dsDre4-BT:SAv-Q655

Results.

Figure 6:
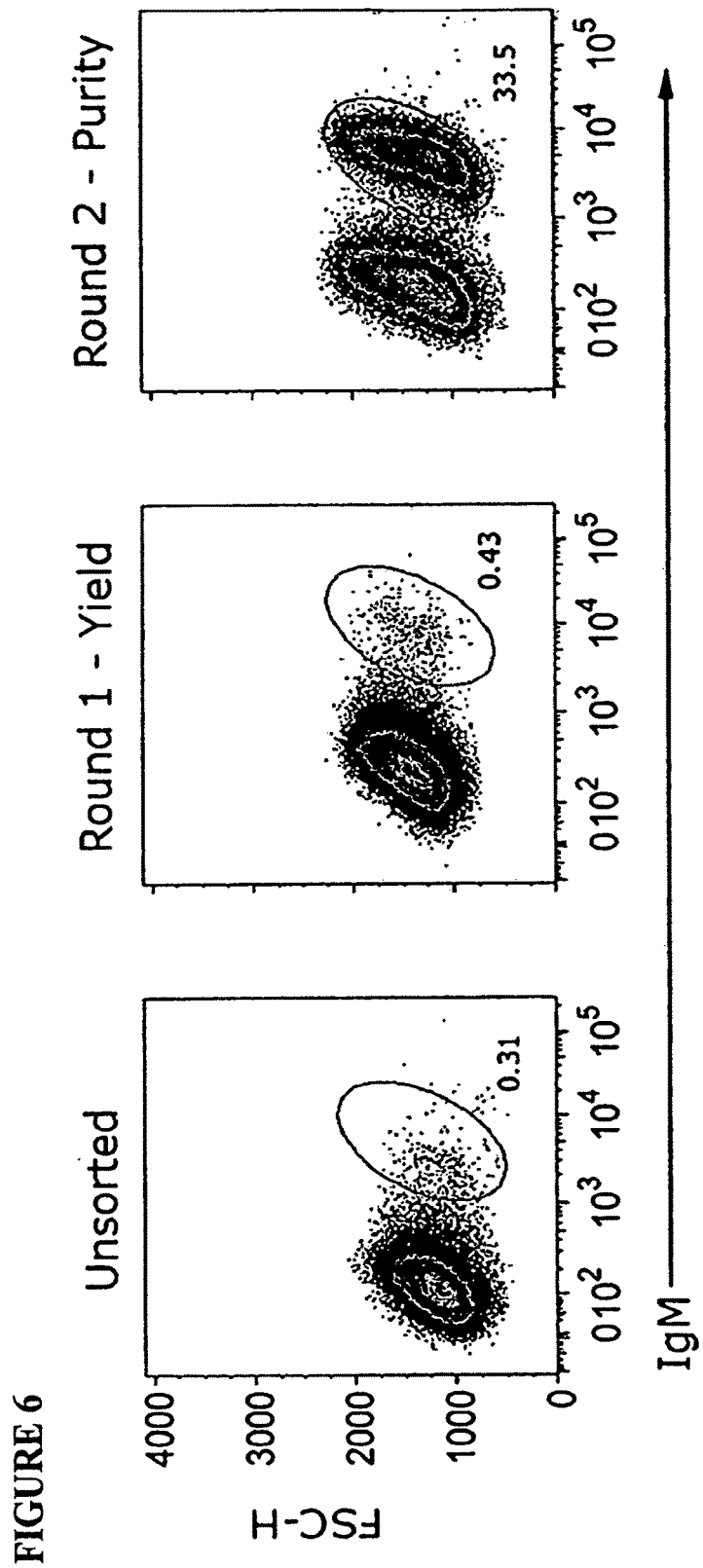
FIG. 6 shows, according to particular exemplary aspects, efficient enrichment of rare dsOligo binding cell populations by FACS. Approximately $5 \times 10^3$ IgM$^+$ DT40 cells expressing I-AniI (clone B10) were mixed with $5 \times 10^7$ of IgM DT40 cells expressing a non-binding mutant I-AniI$^m$ (for a final ratio of 1:10$^4$, or 0.01%) followed by staining with dsAni1-BT:SAv-PE. For the first round of cell sorting, the instrument precision was set for high yield and approximately 10$^5$ cells of the top 0.2% PE-positive population were collected. This population was grown up for 5-7 days, analyzed by staining with FITC-conjugated anti-IgM, and then re-sorted with the instrument precision set for high purity.
Figure 7:
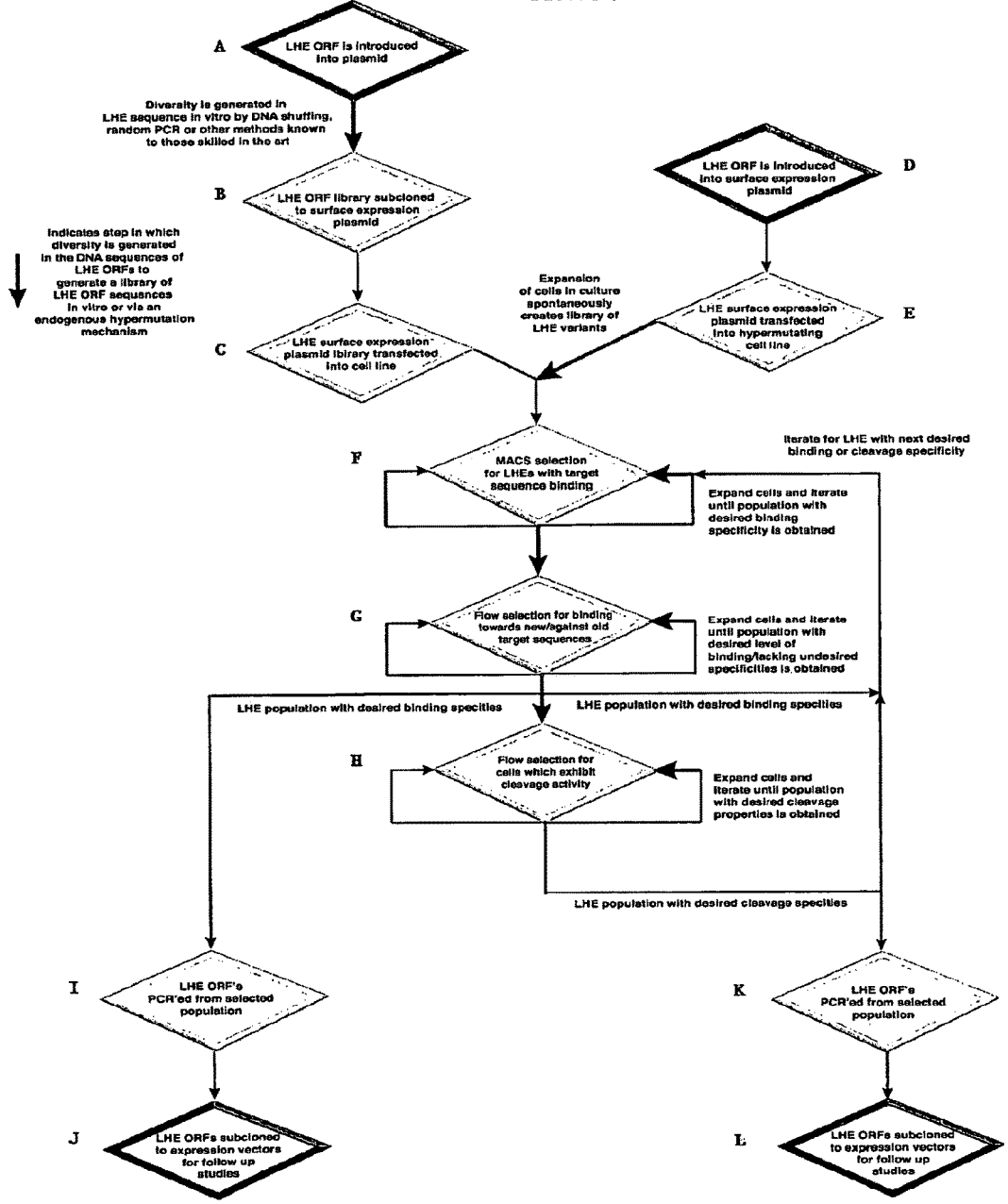
FIG. 7 shows, according to particular exemplary aspects, a flow diagram illustrating exemplary means to generate and use surface displayed HEs (LAGLIDADG endonucleases) for identification of new homing endonucleases with novel binding and/or cleavage specificities.

The dsAni1-specific and dsDre4-specific populations were isolated concurrently using FACS and analyzed for their relative target specificities (FIG. 4*a*). A significant enrichment of both I-AniI and H-DreI positive populations to 80% was achieved after the first round of sorting, and essentially no cross-contamination of the purified I-AniI or H-DreI populations was detected. The capacity of dsOligo-dependent cell sorting was further explored by assessing the enrichment of low frequency I-AniI expressing cells from a background of I-AniI$^m$ expressing cells, for which two iterative rounds of FACS sorting enriched an initial 0.01% population to 33% (FIG. 6). FIG. 6 shows, according to particular exemplary aspects, efficient enrichment of rare dsOligo binding cell populations by FACS. Approximately $5 \times 10^3$ IgM$^+$ DT40 cells expressing I-AniI (clone B10) were mixed with $5 \times 10^7$ of IgM$^-$ DT40 cells expressing a non-binding mutant I-AniI$^m$ (for a final ratio of 1:10$^4$, or 0.01%) followed by staining with dsAni1-BT:SAv-PE. For the first round of cell sorting, the instrument precision was set for high yield and approximately $10^5$ cells of the top 0.2% PE-positive population were collected. This population was grown up for 5-7 days, analyzed by staining with FITC-conjugated anti-IgM, and then re-sorted with the instrument precision set for high purity.

These data demonstrate, according to particular inventive aspects, that FACS sorting using fluorescently conjugated dsOligos is a highly effective method for the viable recovery of LHE expressing cells based on their DNA target specificity, and that rare clones with desired specificities may be effectively isolated and enriched from large background populations.

Example 5

Magnetic Cell Sorting (MACS) was Used to Rapidly Isolate LHE Expressing Cells Labeled with Biotin-Conjugated dsOligos According to additionally aspects of the present invention, various methods can be used for the enrichment and/or isolation of low-frequency HE or LHE expressing cells.

In particular embodiments, the utility and suitability of magnetic cell sorting (MACS) was assessed and confirmed for isolation of low-frequency LHE expressing cells (FIG. 4b). A principle advantage of MACS is its ability to process extremely large sample sizes in short time periods (screening rates greater than $10^5$ cells per second were routinely used in Applicant's protocols), thereby providing a convenient mechanism to sample large libraries of LHE clones. In certain aspects, an IgM-negative background population expressing high levels of an I-AniI$^m$ clone containing a mutated DNA binding interface that was designed to eliminate direct contacts with one side of the asymmetric wild-type target sequence was employed. Consistent low level staining with dsAni1 indicated that low affinity interactions with the wild-type target sequence are retained (FIG. 4b, middle panels). The IgM-positive B10 clone expressing wild type I-AniI was added at a frequency of 0.1%. According to particular aspects, the use of IgM as a surrogate marker for wild-type I-AniI expression allows for more accurate discrimination of low-percentage populations after dsOligo dependent sorting due to a higher signal to noise ratio compared with dsOligo staining. To control for potential low affinity interactions of dsOligos with IgM on the cell surface, IgM-positive cells expressing I-AniI$^m$ were included in the initial sample at a frequency of approximately 0.5%. The mixed population was labeled with dsAni1-BT in the presence 10 mM $Ca^{2+}$, followed by incubation with SAv-coated magnetic beads. Binding and non-binding fractions were isolated using a double-column positive selection protocol on an AutoMACS cell sorter. Initial experiments indicated that 0.1% starting populations can be consistently enriched to by two orders of magnitude after a single round of MACS with sample sizes as large as $10^8$ cells, despite residual low affinity interactions with the bulk of cells expressing a mutated enzyme. Importantly, the enriched IgM-positive population was entirely composed of dsAni1-binding cells expressing wild-type I-AniI and not the IgM-positive fraction expressing I-AniI$^m$ (FIG. 4b, lower panels). Significantly, these results additionally establish that high level expression of surface molecules with the potential for both spurious (IgM) and specific (I-AniI$^m$) low affinity interactions with DNA substrates do not compromise the specificity of dsOligo dependent enrichment by MACS.

Example 6

Cell Surface-Expressed LHEs were Successfully Employed for Flow Cytometry-Based Cleavage Assays The Example confirms that cell surface-expressed LHEs retained sequence specific endonuclease activity, and provides for applications of the inventive subject matter in cell sorting based cleavage assays (e.g., flow cytometry-based cleavage assays).

Methods.

To evaluate whether surface LHEs retained sequence specific endonuclease activity, novel LHE target sequences were designed with two distinct fluorophores at opposite termini. In particular exemplary aspects, each oligo was modified at its 5' terminus with either Alexa Fluor 647 or biotin during synthesis and were annealed to obtain dually-conjugated dsOligos (647-dsOligo-BT, FIG. 2a) which were mixed with SAv-PE at a 1:1 molar ratio to obtain a bifluorescent 647-dsAni1-BT:SAv-PE staining reagent. Cells were first labeled with a biotin-conjugated anti-HA monoclonal antibody ($\alpha$-HA-BT) followed by the addition of pre-formed 647-dsAni1-BT:SAv-PE complexes which should contain an average of three remaining BT-binding sites per SAv tetramer. This staining protocol serves to tether the 647-dsAni1-BT:SAv-PE to the cell surface independent of any specific LHE-dsOligo interaction, yet still placing the dsOligo within the LHE's immediate environment (FIG. 5a).

Results.

FIGS. 5a-5e show, according to particular exemplary aspects, data confirming sequence-specific, LHE-mediated cleavage of cell surface-tethered dsOligo substrates conjugated with distinct fluorophores at opposite termini. FIG. 5(a) shows a schematic diagram of an inventive embodiment for assaying surface LHE cleavage of $\alpha$-HA-BT tethered dually-fluorescent labeled dsOligos and the release of Alexa Fluor 647 following addition of $Mg^{2+}$ (red dots). Therefore, the presently disclosed inventive aspects encompass the conception that if the tethered 647-dsOligo-BT can be cleaved by the surface LHE, the cells would lose the fluorescence signal contribution from Alexa Fluor 647 yet retain signal from the tightly bound bridging SAv-PE.

Figure 5B:
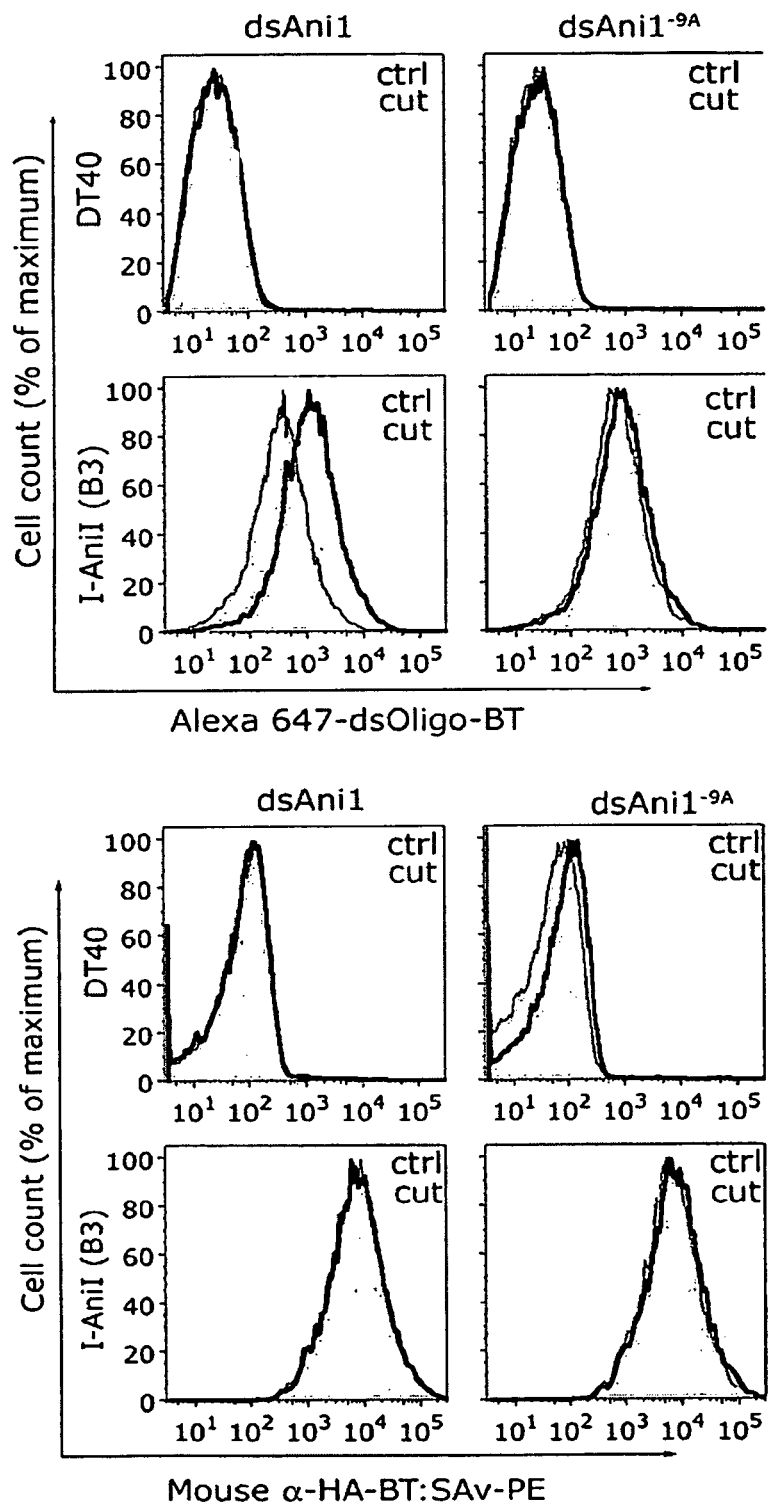

Additionally, it was conceived that because both antibody binding and SAv:BT interactions are independent of divalent cation contribution, a $Ca^{2+}$ and $Mg^{2+}$-free buffer might be used to stain I-AniI expressing cells with $\alpha$-HA-BT followed by 647-dsAni1-BT:SAv-PE. Prior to the present conception and disclosure, the $Ca^{2+}$ and $Mg^{2+}$ specificity on DNA target site cleavage activities of homing endonucleases (HE) were only known to occur in the context of free-standing enzymes in solution and/or intracellularly. The cells were then spiked with 10 mM $Mg^{2+}$ and placed at 42° C. in order to restore optimal cleavage conditions (Geese, et al., Eur J Biochem, 270:1543-1554, 2003) (without $Mg^{2+}$ for control samples). Using bifluorescent dsAni1 it was possible to readily assay sequence specific endonuclease activity by clones expressing wild-type I-AniI by monitoring changes in the fluorescence signals from each fluorophore (FIG. 5b). FIG. 5(b) shows DT40 and B3 cells that were stained with A-HA-BT followed by 647-dsOligo-BT:SAv-PE pre-formed complexes to tether the dsOligos to the surface LHE via the HA epitope. Cells with surface tethered dsAni1 or dsAni1$^{-9.4}$ substrates were incubated at 42° C. for 20 min with (filled histograms) or without (open histograms) $Mg^{2+}$ and analyzed by flow cytometry. Though the fluorescence data was collected simultaneously, the fluorescence from Alexa Fluor 647 and PE are represented separately in the upper and lower panel sets, respectively, to demonstrate specific loss of the untethered fluorophore signal.

Figure 5C:
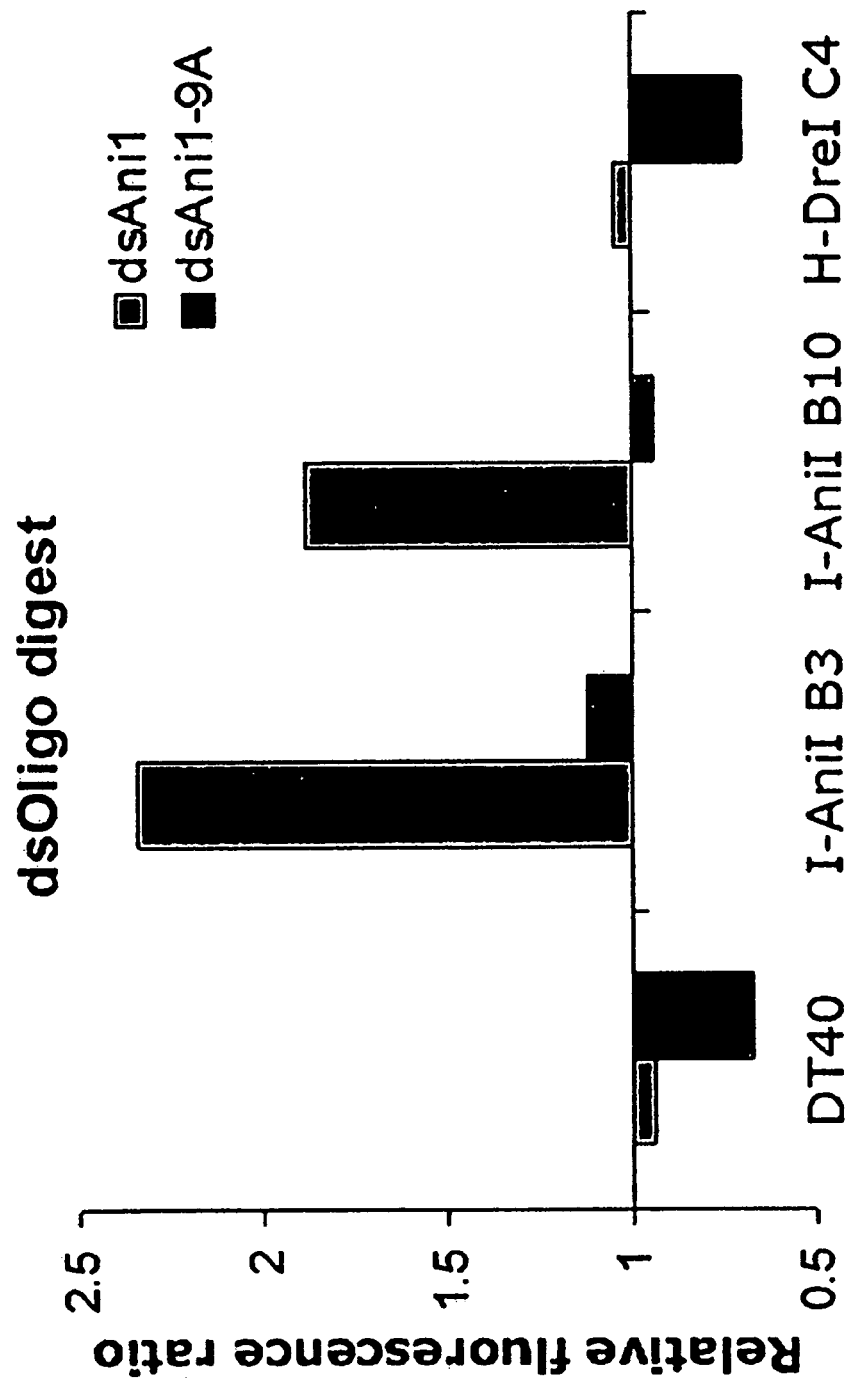

Time-course experiments were performed to observe the relative disappearance of Alexa Fluor 647 fluorescence, which indicated that the signal progressively decreased during the first twenty minutes of incubation. Given the data demonstrating the strict sequence specificity of the surface expressed LHE DNA-binding interaction, bifluorescent dsAni1$^{-9.4}$ was used as a stringent control for the specificity of the cleavage reaction. Consistent with the clear differences in the binding data for these dsOligos, no relative fluorescent signal changes were observed for dsAni1$^{-9.4}$ under optimal cleavage conditions, confirming that dsAni1$^{-9.4}$ was not cleaved by the surface LHEs. The PE:647 fluorescence ratios and their relative changes with each dsOligo species was calculated as an indicator of the relative substrate cleavage. This quantification clearly demonstrates a substantial increase in the PE:647 ratio only where the bifluorescent dsOligo matched the natural target sequence for I-AniI (FIG. 5c). FIG. 5(c) shows quantification of the extent of dsOligo cleavage by I-AniI by calculating a ratio of the mean PE to Alexa Fluor 647 fluorescence intensities.

Blue columns indicate changes in the PE:647 fluorescence ratio for dsAniI cleavage whereas purple columns show relative ratio shifts for the dsAriI$^{-9.4}$ substrate.

Figure 5D:
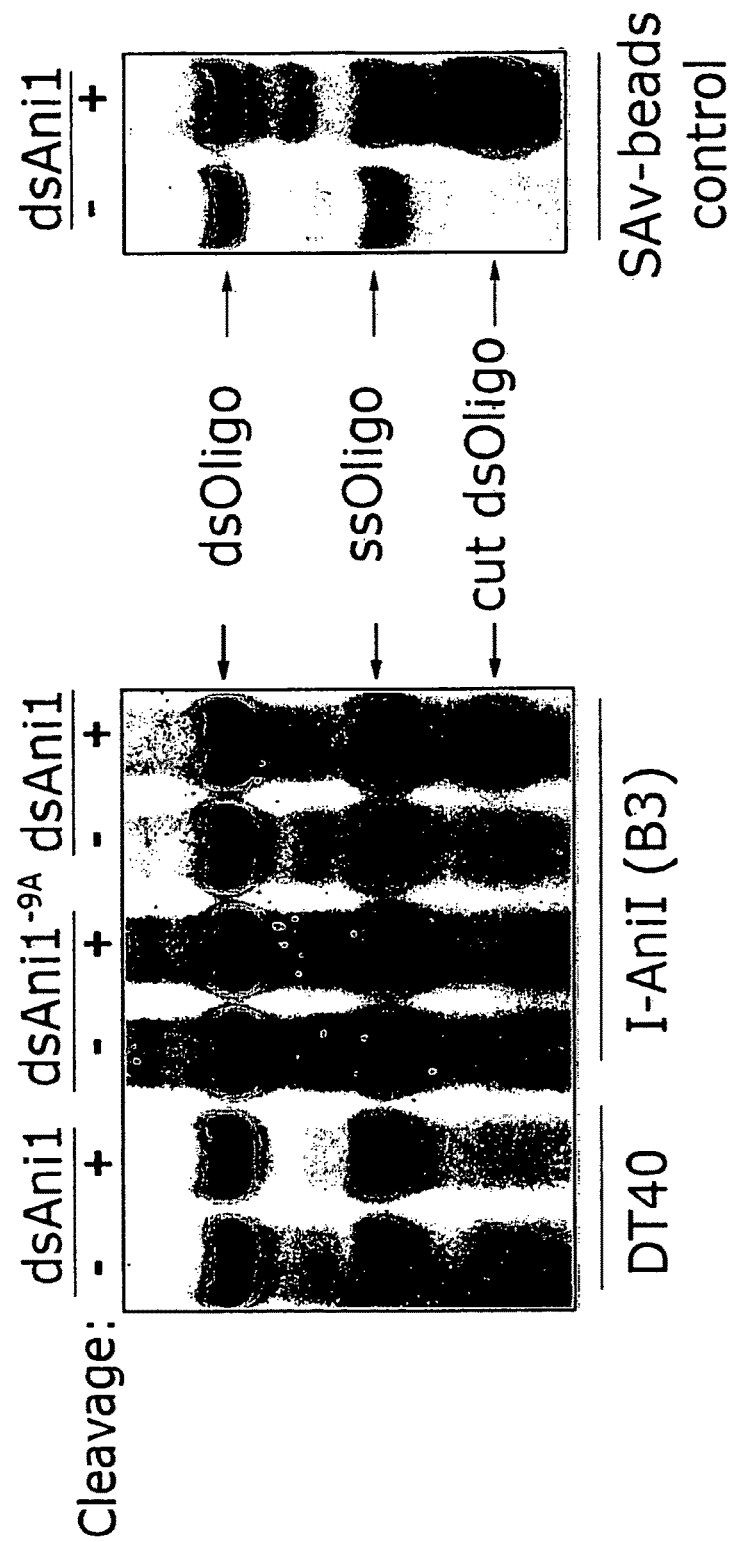

One possible interpretation of this result is that the sequence-specific reduction of the Alexa Fluor 647 signal was due to fluorophore quenching following LHE-binding and not necessarily from cleavage and release of the fragment. The presence of the cleaved fragment in the supernatants of cleavage experiments was therefore verified (FIG. 5d). FIG. 5(d), left panel, shows PAGE/fluorescence imaging data from DT40 cells and I-AniI expressing cells (B3) that were stained as described in FIG. 5(b) and incubated at 42° C. for 30 min in the presence (+) or absence (−) of Mg$^{2+}$. FIG. 5(d), right panel, shows PAGE/fluorescence imaging data from 647-dsOligos-BT were bound to SAv-conjugated magnetic beads and incubated with recombinant I-AniI for 1 hour at 42° C. In both instances, DNA fragments were purified from supernatants and analyzed by PAGE followed by fluorescence imaging (see Methods under Example 1 herein).

Significantly, the cells used for the cleavage reactions were analyzed by flow cytometry to confirm specific loss of the Alexa Fluor 647 signal (as in FIG. 5b). Control cleavage assays were performed in vitro using recombinant I-AniI to confirm that 647-dsAni1-BT alone or complexed with SAv-coated beads was readily accessible and efficiently cleaved by the purified enzyme. In both experiments co-migrating fluorescent fragments of smaller molecular weight were identified compared to full-length double-stranded and residual single-stranded oligonucleotides. Smaller fragments were not detected in controls with dsAni1$^{-9.4}$ or where the cleavage reaction was performed in the absence of either Mg$^{2+}$ or I-AniI.

Figure 5E:
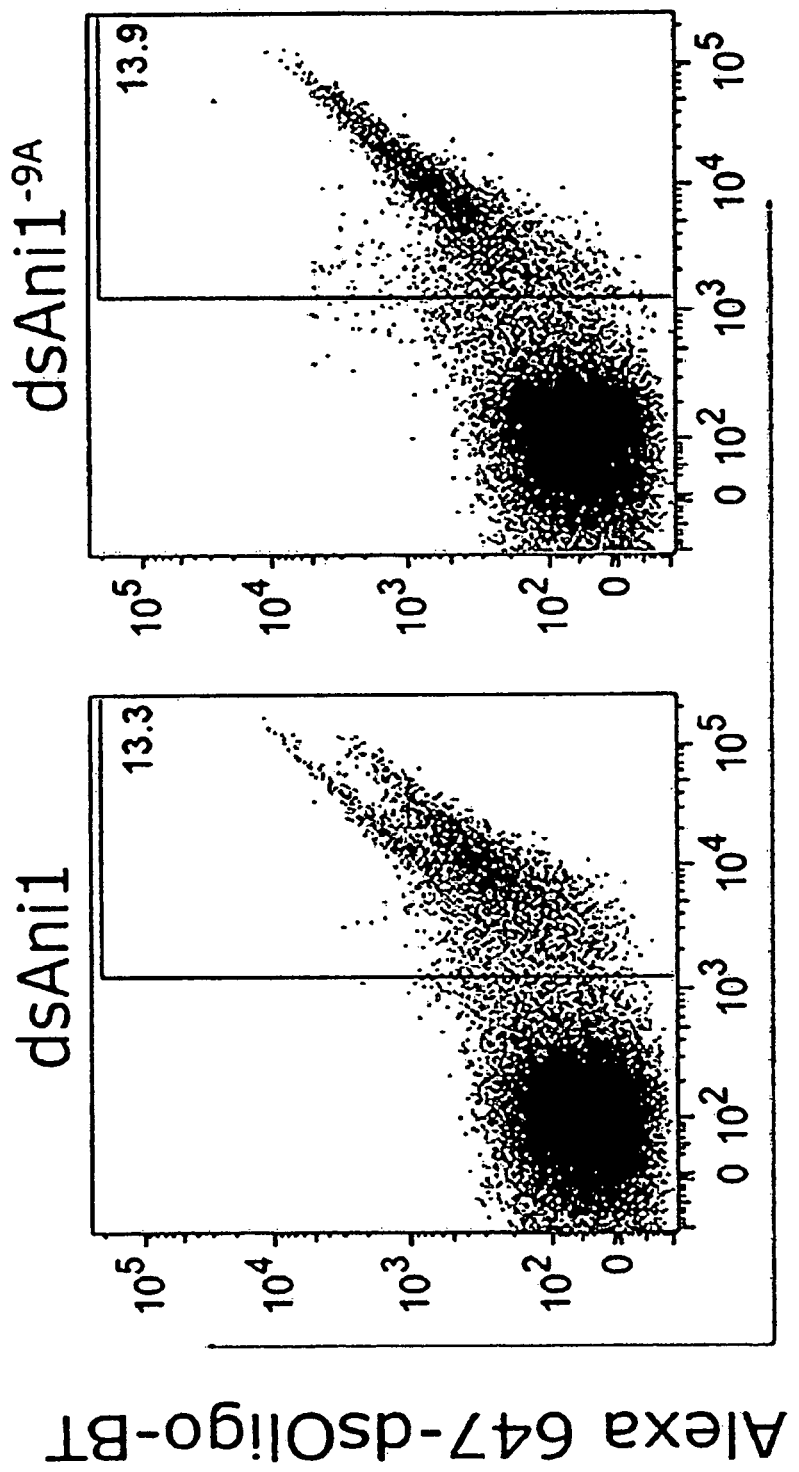

An experiment was additionally performed to confirm that the tethered dsOligos were being cleaved by LHEs on the very cells to which they were tethered. This is an important validation because cleavage caused by LHEs from adjacent cells might confound future attempts at FACS sorting by fluorescent signal loss following dsOligo cleavage. Using a mixed population of DT40 cells and I-AniI expressing (B3) cells at a 10:1 ratio where contacts between individual I-AniI expressing cells are decreased, sequence specific reduction of Alexa Fluor 647 fluorescence was observed to continue to a similar extent as in a pure I-AniI-positive population (FIG. 5e). FIG. 5(e) shows FACS data from DT40 cells and I-AniI expressing cells (B3) that were mixed at 10:1 ratio, labeled as described in FIG. 5(b) and incubated at 42° C. for 20 min with (blue) or without (17) Mg$^{2+}$ followed by flow cytometry analysis.

Therefore, the data indicate that individual dsOligos are primarily bound and digested by LHEs autonomously on the cell surface, and that under suitable or optimal reaction conditions the surface expressed LHEs are catalytically active and functionally recapitulate their highly sequence specific nuclease activity.

Example 7

Particular Aspects Provide Methods for Introducing a DSB into a Target Cell, Comprising Use of an HE or LHE Isolated Using at Least One of the Novel Compositions or Methods Disclosed Herein Particular aspects provide a method for introducing a double strand break in the genome of a virus or of a living cell, comprising: isolating an HE or LHE using at least one of the novel compositions or methods disclosed herein to provide for a specific, desired DNA cleavage specificity within the target viral or cellular genome; and introducing the cognate HE or LHE into DNA containing subcellular compartments of a respective living cell or population of living cells by any suitable art recognized method. In embodiments where the desired target genome is a virus genome, a fraction of the cell population to which the cognate HE or LHE is introduced would present a DNA intermediate of said target virus genome. In embodiments where the target genome is the genome of a cell or cell population to which the HE or LHE is delivered, each said living cell may comprise an entire living organism (e.g., a unicellular organism), or each said cell population may be all or a subset of cells of a living organism (e.g., a multicellular organism).

For said applications, the HE or LHE to be introduced would be linked to any of a number of forms of subcellular localization peptides necessary or sufficient to target the HE or LHE to an appropriate DNA containing cell organellar compartment (e.g., the cell nucleus, cell mitochondria, etc), and said targeting peptides could for example be, respectively, nuclear localization signals or mitochondrial targeting signals, of which many forms of each type of targeting peptide are known to those skilled in the art. Said subcellular localization peptide/LHE polypeptide combinations are hereafter referred to as "targeting HEs" or "targeting LHEs."

Said introducing the cognate targeting HE or LHE could, for example involve administration alone or in association with an appropriate vehicle or carrier peptide and/or with a polynucleotide fragment. Exemplary appropriate vehicles may be selected from the group consisting of liposomes, polyethyleneimine, membrane translocating peptides, and combinations thereof. In embodiments involving use of membrane translocating peptides, such peptides could be appended to the targeting HE or LHE polypeptide through a peptide or other chemical bond, or in alternative embodiments, could be a separate component of the vehicle.

Alternatively, said targeting HE or LHE polypeptide could be introduced in the context of a suitable, expression vector; that is, in the form of a polynucleotide encoding said targeting HE or LHE polypeptide under the control of appropriate transcriptional regulatory elements including a promoter (e.g., a tissue specific and/or inducible promoter). Such polynucleotide could be in purified form, or could be in the form of a viral particle, of which many forms are known in the art (e.g. retroviral particles including lentiviral particles, adenoviral particles, adenoassociated (AAV) viral particles, among many others).

In particular embodiments, usage would be made of the well known capacity of HE or LHE-directed DNA cleavage to induce homologous recombination ( ). In such embodiments, a polynucleotide fragment would be cointroduced with the targeting HE or LHE polypeptide for the purpose of directly (or indirectly, by direction of the production of new DNA fragments of identical sequence via templated DNA synthesis) participating in homologous recombination with sequences surrounding the HE or LHE cleavage site. Said polynucleotide fragment comprises a "site of interest" flanked by flanking sequences sharing homologies to sequences on either side of the HE or LHE cleavage site. A "site of interest" as referred to herein is any DNA sequence, preferably smaller than 4000 base pairs, and more preferably smaller than 2000 base pairs. In particular aspects, the flanking sequences comprise at least 50 bp, preferably more than 200 bp, and most preferably more than 1500 bp of homology with regions on either side of LHE or HE cleavage site.

Alternatively, a targeting HE or LHE polypeptide is incorporated into viral particles, preferably viral particles derived from viruses which do not integrate their genomes into their host cell genome, and more preferably lentiviral (e.g. HIV-1) particles containing an activity-deficient integrase and/or mutated integrase recognition sites to prevent viral particle genome integration (see., e.g., Nightingale et al, Mol. Therapy, 2006, 13(6):1121-1132). In such embodiments, incorporation of the HE or LHE into the non-integrating lentiviral particle may occur through a fusion of the C-terminus of an accessory protein (e.g. VPR) to a lentiviral protease cleavage site fused to the N-terminus of the LHE, as in previously described fusion protein approaches (see., e.g., Wu, X et al, J. Virol. 1995; 69(6): 3389-98, Sato A et al, Microbiol Immunol. 1995; 39(12): 1015-9). Such an approach is also described for incorporation of I-SceI LHE into lentiviral particles in US patent application 20050266565).

In embodiments in which the HE or LHE polypeptide is incorporated into viral particles, the viral particle genome optionally includes a polynucleotide fragment designed to participate in homologous recombination with sequences surrounding the HE or LHE cleavage site. In some embodiments, said viral particles possess a DNA genome (e.g. members of the foamy virus family). In such embodiments, said polynucleotide fragment is a DNA fragment encoding a "site of interest" flanked by flanking sequences sharing homologies to sequences on either side of the HE or LHE cleavage site. A "site of interest" as referred to herein is any DNA sequence of a size packageable in said viral particle, preferably smaller than 4000 base pairs, and more preferably smaller than 2000 base pairs. In particular aspects, the flanking sequences comprise at least 50 bp, preferably more than 200 bp, and most preferably more than 1500 bp of homology with regions on either side of HE or LHE cleavage site.

In other embodiments, said viral particles possess an RNA genome which is converted to DNA via reverse transcription after viral particle transduction of target cells (e.g. lentiviral particles, including HIV-1, HIV-2 and related members of the lentiviral family). In such embodiments, said polynucleotide fragment is an RNA fragment, which after reverse transcription into a double stranded DNA in the target cell, encodes a "site of interest" flanked by flanking sequences sharing homologies to sequences on either side of the HE or LHE cleavage site. A "site of interest" as referred to herein is any nucleotide sequence of a size packageable in said viral particle, preferably smaller than 4000 base pairs, and more preferably smaller than 2000 base pairs. In particular aspects, the flanking sequences comprise at least 50 bp, preferably more than 200 bp, and most preferably more than 1500 bp of homology with regions on either side of HE or LHE cleavage site.

Example 8

Particular Aspects Provide Methods for Chromatin Immunoprecipitation (CHIP)

The chromatin immunoprecipitation (CHIP) method is a widely used method for isolating genomic DNA fragments bound to various types of DNA binding and regulatory proteins (reviewed in Weinmann, Nature Reviews Immunol, 2004, 4(5):381-6), Elnitski L et al, Genome Res. 2006 December; 16(12):1455-64). Briefly, prior art CHIP methods involve attempts to isolate DNA sequences which are bound by specific proteins of interest (e.g., endogenous transcription factors or other regulatory proteins) by chemically 'crosslinking' of the totality of genomic DNA in its intact context with its interacting proteins, shearing the DNA/protein complexes to reduce the DNA polymer length and provide DNA fragments of tractable size, and precipitating DNA fragments bound to the specific protein of interest using antibodies to the protein of interest.

The precise complement of proteins interacting with a given locus under different conditions (e.g., cell growth, differentiation stage, tumor stage, etc.) is a factor of fundamental importance in understanding the role/regulation of the locus. However, prior art CHIP methods are significantly limited in this respect, because a particular endogenous regulatory protein may bind at many sites that will be co-immunoprecipitated using prior art methods, and thereby precluding specific (e.g., individual/separate) analysis of the particular protein interaction at a specific target locus. Therefore, because typical endogenous regulatory proteins bind to multiple genomic DNA sites, there is presently no way to isolate a specific DNA fragment/regulatory protein complex from among the co-immunoprecipitated complexes using conventional CHIP methods and technology.

According to additional aspects of the present invention, the novel methods disclosed herein provide for the generation, selection and isolation of highly specific DNA binding proteins. Therefore, particular inventive aspects comprise use of the presently disclosed methods and compositions for isolating specific genomic loci along with their bound regulatory protein components.

Particular embodiments provide methods for isolating a specific genomic DNA:protein complex (e.g., specific genomic DNA fragment with bound regulatory proteins) of a virus or of a living cell of interest, comprising introduction into said cell an inactive form of an HE or LHE, or a cognate epitope-tagged version of said inactive LHE, isolated using at least one of the novel compositions or methods disclosed herein to provide for a specific, desired DNA binding specificity, and to provide for specific LHE/DNA complexes within the target viral or cellular genome. In particular embodiments, the methods further comprise: crosslinking of the genomes and associated proteins according to the art-recognized CHIP chromatin immunoprecipitation techniques to provide for crosslinking of the inactive LHE to its bound target site; shearing (e.g., by sonication); and immunoprecipitating the inactive LHE and its bound DNA fragment using antibodies to the inactive LHE, or to the epitope tag on the inactive LHE. Additional embodiments further comprise reversing the crosslinking process (as is standard in art-recognized CHIP methods), to provide for dissociation of the DNA/protein complexes. Therefore, because the inactive LHE or their cognate epitope-tagged versions bind to one or a limited number of genomic target sites, particular aspects of the present invention provide improved CHIP methods for identifying components of specific genomic DNA:protein complexes of a given specific locus utilizing standard protein microanalysis methods, such as mass spectrometry.

Said inactive forms of LHEs are easily constructed by those of ordinary skill in the art via mutation of residues critical for LHE endonuclease activity (e.g. see Chevalier B et al, Biochemistry. 2004 Nov. 9; 43(44):14015-26; Chevalier, Nucleic Acids Res. 2001 Sep. 15; 29(18):3757-74), but which leave intact or largely intact residues required for sequence specific DNA binding.

In embodiments where the desired target genome is a virus genome, a fraction of the cell population to which the inactive LHE is introduced would present a DNA intermediate of said target virus genome. In embodiments where the target genome is the genome of a cell or a cell population to which the inactive LHE is delivered, each said living cell may comprise an entire living organism (e.g., a unicellular organism) or may be part of a cell population, which is all or a subset of cells of a living organism (e.g., a multicellular organism).

For said applications, the inactive LHE to be introduced would be linked to any of a number of forms of subcellular localization peptides necessary or sufficient to target the LHE to an appropriate cell organellar compartment (e.g., the cell nucleus, cell mitochondria, etc), and said targeting peptides could for example be, respectively, nuclear localization signals or mitochondrial targeting signals, of which many forms of each type of targeting peptide are known to those of ordinary skill in the art. Said inactive subcellular localization peptide/LHE polypeptide combinations are hereafter referred to as "inactive targeting LHEs".

Said introducing the cognate inactive targeting LHE could, for example involve administration alone or in association with an appropriate vehicle or carrier peptide and/or with a nucleotide fragment. Exemplary appropriate vehicles may be selected from the group consisting of liposomes, polyethyleneimine, membrane translocating peptides, and combinations thereof. In embodiments involving use of membrane translocating peptides, such peptides could be appended to the inactive targeting LHE polypeptide through a peptide bond, or in alternative embodiments, could be a separate component of the vehicle.

Alternatively, said inactive targeting LHE polypeptide could be introduced in the context of a suitable, expression vector; that is, in the form of a polynucleotide encoding said inactive targeting LHE polypeptide under the control of appropriate transcriptional regulatory elements including a promoter (e.g., a tissue specific and/or inducible promoter). Such polynucleotide could be in purified form, or could be in the form of a viral particle, of which many forms are known in the art (e.g. retroviral particles including lentiviral particles, adenoviral particles, adenoassociated (AAV) viral particles).

Alternatively, an inactive targeting LHE polypeptide is incorporated into viral particles, preferably viral particles derived from viruses which do not integrate their genomes into their host cell genome, and more preferably lentiviral (e.g. HIV-1) particles containing an activity-deficient integrase and/or mutated integrase recognition sites to prevent viral particle genome integration (see., e.g., Nightingale et al, Mol. Therapy, 2006, 13(6):1121-1132). In such embodiments, incorporation of the inactive targeting HE or LHE into the non-integrating lentiviral particle occurs through a fusion of the C-terminus of an accessory protein (e.g. VPR) to a lentiviral protease cleavage site fused to the N-terminus of the interactive targeting HE or LHE, as described (see., e.g., Wu, X et al, J. Virol. 1995; 69(6):3389-98).

The invention claimed is:

1. A method of identifying a eukaryotic homing endonuclease with a desired target specificity, comprising:

expressing, utilizing a recombinant expression system, at least one monomeric eukaryotic homing endonuclease-fusion protein (HE-fusion) comprising a HE and an epitope tag, in one or more eukaryotic cells, the recombinant expression system and the one or more eukaryotic cells suitable to provide for cell-surface presentation or display of the at least one HE-fusion protein;

contacting the one or more eukaryotic cells expressing the at least one HE-fusion protein with at least one labeled target nucleic acid sequence under suitable conditions to tether the at least one labeled target nucleic acid sequence to the eukaryotic cell surface independent of any specific interaction between the HE of the at least one HE-fusion protein and the at least one labeled target nucleic acid sequence, wherein the suitable conditions comprise the at least one labeled target nucleic acid sequence bound by biotin-streptavidin to a conjugated antibody that specifically binds the epitope tag of the HE-fusion protein, thereby tethering the at least one labeled target nucleic acid sequence; and selecting, based on detection of cleavage of the tethered labeled target nucleic acid sequence, one or more eukaryotic cells expressing at least one cell surface HE having a desired target sequence cleavage activity.

2. The method of identifying a eukaryotic homing endonuclease with a desired target specificity of claim 1, further comprising, after contacting to allow for tethering of the at least one labeled target nucleic acid sequence:

adjusting the conditions to allow for homing endonuclease-mediated cleavage of the at least one labeled target nucleic acid sequence; and selecting, based on detection of cleavage of the tethered labeled target nucleic acid sequence, one or more eukaryotic cells expressing at least one cell surface HE having a desired target sequence cleaving activity.

3. The method of claim 2, wherein the conditions that allow for homing endonuclease-mediated cleavage of the at least one labeled target nucleic acid sequence comprise a concentration of at least one of magnesium, cobalt, manganese, nickel and/or zinc ions sufficient to allow for target sequence cleavage, and a concentration of calcium and/or copper ions that does not completely inhibit target sequence cleavage.

4. The method of claim 1, wherein the HE-fusion protein comprises at least one selected from the group consisting of a signal peptide, a membrane-anchoring moiety, a membrane-anchoring polypeptide, and combinations thereof.

5. The method of claim 1, wherein the recombinant expression system comprises expression from at least one recombinant HE-fusion protein expression vector or from at least one recombinant genomic locus.

6. The method of claim 1, wherein the one or more eukaryotic cells comprise vertebrate cells, mammalian cells, metazoan cells, yeast cells, and unicellular eukaryotic cells.

7. The method of claim 1, wherein selecting comprises magnetic activated cell sorting, fluorescence activated cell sorting, or combinations thereof.

8. The method of claim 1, wherein the at least one labeled target nucleic acid sequence comprises at least one of a known or putative homing endonuclease (HE) binding sequence and a known or putative homing endonuclease cleavage sequence.

9. The method of claim 1, wherein each one of the one or more eukaryotic cells expresses a single homing endonuclease (HE) sequence.

10. The method of claim 1, wherein the homing endonuclease (HE) comprises at least one selected from the group consisting of LHE, HNH, His-Cys Box, GIY, and I-SspI-type having the same or altered target nucleic acid sequence binding and/or cleavage activity.

11. The method of claim 10, wherein the homing endonuclease (HE) comprises at least one LHE HE selected from the group consisting of I-AniI, H-DreI, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I, wherein the LHE LE has the same or altered target nucleic acid sequence binding and/or cleavage activity.

12. The method of claim 1, wherein the epitope tag is selected from the group consisting of: a histidine tag (His) tag, a FLAG tag, an influenza hemagluttinin (HA) tag, a Myc tag, a VSV-G tag, and a thioredoxin (Trx) tag.

* * * * *

UNITED STATES PATENT AND TRADEMARK OFFICE
CERTIFICATE OF CORRECTION

PATENT NO. : 10,407,672 B2  
APPLICATION NO. : 12/295201  
DATED : September 10, 2019  
INVENTOR(S) : Andrew M. Scharenberg Page 1 of 1

It is certified that error appears in the above-identified patent and that said Letters Patent is hereby corrected as shown below:

In the Specification

In the Statement Regarding Federally-Sponsored Research section, Column 1, Lines 18-21, please replace:
"This work was funded at least in part under grant number R21AI064581 from the
National Institutes of Health, and the United States Government may therefore have certain rights."
With:
--This invention was made with government support under AI064581 awarded by the National
Institutes of Health. The government has certain rights in the invention.--

Signed and Sealed this
Fourth Day of May, 2021

Drew Hirshfeld
*Performing the Functions and Duties of the
Under Secretary of Commerce for Intellectual Property and
Director of the United States Patent and Trademark Office*